US008129514B2

(12) United States Patent
Ronen et al.

(10) Patent No.: US 8,129,514 B2
(45) Date of Patent: Mar. 6, 2012

(54) NUCLEOTIDE SEQUENCES FOR REGULATING GENE EXPRESSION IN PLANT TRICHOMES AND CONSTRUCTS AND METHODS UTILIZING SAME

(75) Inventors: Gil Ronen, Moshav Ometz Emek Hefer (IL); Larisa Rabinovich, Rishon-LeZion (IL); Rafael Meissner, Rechovot (IL); Hagai Karchi, Moshav Sitriya Doar-Na Emek Soreq (IL)

(73) Assignee: Evogene Ltd., Rechovot (IL)

( * ) Notice: Subject to any disclaimer, the term of this patent is extended or adjusted under 35 U.S.C. 154(b) by 331 days.

(21) Appl. No.: 12/320,937

(22) Filed: Feb. 9, 2009

(65) Prior Publication Data
US 2009/0253170 A1 Oct. 8, 2009

Related U.S. Application Data

(63) Continuation-in-part of application No. 10/561,220, filed as application No. PCT/IL2004/000549 on Jun. 20, 2004, now Pat. No. 7,498,428.

(60) Provisional application No. 60/479,467, filed on Jun. 19, 2003.

(51) Int. Cl.
C07H 21/04 (2006.01)
C12N 15/82 (2006.01)
A01H 5/00 (2006.01)

(52) U.S. Cl. ....... 536/24.1; 800/295; 800/298; 800/287; 435/320.1; 435/419

(58) Field of Classification Search .................. None
See application file for complete search history.

(56) References Cited

U.S. PATENT DOCUMENTS

| | | | |
|---|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,666,828 A | 5/1987 | Gusella |
| 4,683,202 A | 7/1987 | Mullis |
| 4,801,531 A | 1/1989 | Frossard |
| 4,879,219 A | 11/1989 | Wands et al. |
| 5,004,863 A | 4/1991 | Umbeck |
| 5,011,771 A | 4/1991 | Bellet et al. |
| 5,097,025 A | 3/1992 | Benfey et al. |
| 5,110,732 A | 5/1992 | Benfey et al. |
| 5,159,135 A | 10/1992 | Umbeck |
| 5,192,659 A | 3/1993 | Simons |
| 5,272,057 A | 12/1993 | Smulson et al. |
| 5,281,521 A | 1/1994 | Trojanowski et al. |
| 5,416,011 A | 5/1995 | Hinchee et al. |
| 5,518,908 A | 5/1996 | Corbin et al. |
| 5,569,834 A | 10/1996 | Hinchee et al. |
| 5,721,138 A | 2/1998 | Lawn |
| 6,326,174 B1 | 12/2001 | Joyce et al. |
| 6,730,826 B2 | 5/2004 | Wagner et al. |
| 2002/0128218 A1 | 9/2002 | Emanuele et al. |
| 2003/0017068 A1 | 1/2003 | Larrain et al. |
| 2003/0096980 A1 | 5/2003 | Froehler et al. |
| 2003/0100050 A1 | 5/2003 | Wagner et al. |
| 2006/0260002 A1 | 11/2006 | Ronen et al. |

FOREIGN PATENT DOCUMENTS

| | | |
|---|---|---|
| EP | 375408 | 2/1995 |
| WO | WO 97/43430 | 11/1997 |
| WO | WO 2004/111183 | 12/2004 |
| WO | WO 2005/121364 | 12/2005 |

OTHER PUBLICATIONS

Szymanski et al. Control of GL2 expression in *Arabidopsis* leaves and trichomes. (1998) Development; vol. 125; pp. 1161-1171.*
Peres et al. Shoot regeneration capacity from roots and transgenic hairy roots of tomato cultivars and wild related species. (2001) Plant Cell, Tissue and Organ Culture; vol. 65; pp. 37-44.*
International Preliminary Report on Patentability Dated Mar. 9, 2006 From the International Bureau of WIPO Re.: Application No. PCT/IL2004/000549.
Official Action Dated Jan. 30, 2008 From the US Patent and Trademark Office Re.: U.S. Appl. No. 10/561,220.
Supplementary Partial European Search Report Dated Jul. 9, 2007 From the European Patent Office Re.: Application No. 04744889.9.
"EST296838 L. Hirsutum Trichome, Cornell University Lycopersicon Hirsutum cDNA Clone cLHT1G135', mRNA Sequence", Database EMBL [Online], Retrieved From, EBI Accession No. EMBL: AW61079. Abstract, (2001).
Notice of Allowance Dated Sep. 8, 2008 From the US Patent Office Re.: U.S. Appl. No. 10/561,220.
Official Action Dated Sep. 17, 2007 From the US Patent Office Re.: U.S. Appl. No. 10/561,220.
Official Action Dated Jan. 30, 2008 From the US Patent Office Re. : U.S. Appl. No. 10/561,220.
Official Communication Dated Sep. 1, 2008 From the European Patent Office Re.: Application No. 04744889.9.
Supplementary European Search Report Dated Sep. 24, 2007 From the European Patent Office Re.: Application No. 04744889.9.
Supplementary Partial European Search Report Dated Jul. 9, 2007 From the European Patent Office Re.: EP 04744889.9.

(Continued)

Primary Examiner — Cathy Kingdon Worley

(57) ABSTRACT

Provided is a novel plant regulatory sequence active in trichomes which is derived from the TR4 gene of wild tomato (*L. hirsutum*) and which comprises a nucleic acid at least 80% identical to SEQ ID NO:26. Also provided are nucleic acid constructs and methods of using same for directing expression of an exogenous polynucleotide sequences in trichomes and transgenic plant cells and transgenic plants which comprise the nucleic acid constructs.

10 Claims, 17 Drawing Sheets
(16 of 17 Drawing Sheet(s) Filed in Color)

OTHER PUBLICATIONS

Hedtke et al. "Green Fluorescent Protein as A Marker to Investigate Targeting of Organellar RNA Polymerases of Higher Plants In Vivo", The Plant Journal, 17(5): 557-561, 1999.

Imajuku et al. "An Upstream Region of the *Arabidopsis thaliana* CDKA;1 (CDC2aAt) Gene Directs Transcription During Trichome Development", Plant Molecular Biology, 46(2): 205-213, 2001. Abstract, p. 208, 1-h col., § 3—r-h col., Last §.

Kulbokaite "SP6 Promoter Sequencing Primer, 18-Mer", Catalog Page From Fermentas Life Sciences, 1P., 2000.

Lai et al. "Effects of Glandular Trichomes on the Development of Phytophthora Infestans Infection in Potato (*S. tuberosum*)", Euphytica, Kluwer Academic Press, 114(3): 165-174, 2000. Abstract.

Larkin et al. "*Arabidopsis* GLABROUS1 Gene Requires Downstream Sequences for Function", The Plant Cell, 5: 1739-1748, 1993.

Liu et al. "Cloning and Promoter Analysis of the Cotton Lipid Transfer Protein Gene Ltp3", Biochimica et Biophysica Acta, 1487: 106-111, 2000.

Mahmoud et al. "Metabolic Engineering of Essential Oil Yield and Composition in Mint by Altering Expression of Deoxyxylulose Phosphate Reductoisomerase and Menthofuran Synthase", Proc. Natl. Acad. Sci. USA, 98(15): 8915-8920, 2001. Abstract, p. 8915, r-h col., Last §.

Menzel et al. "Expression of Bacterial Poly(3-Hydroxybutyrate) Synthesis Genes in Hairy Roots of Sugar Beet (Beta Vulgaris L.)", Applied Microbiological Biotechnology, 60: 571-576, 2003.

Newman et al. "Organisation of the Tomato Polyphenol Oxidase Gene Family", Plant Molecular Biology, 21: 1035-1051, 1993.

Wan et al. "Transit Peptides Play a Major Role in the Preferential Import of Proteins Into Leucoplasts and Chloroplasts", The Journal of Biological Chemistry, 271(49): 31227-31233, 1996.

Wang et al. "Elucidation of the Functions of Genes Central to Diterpene Metabolism in Tobacco Trichomes Using Post-transcriptional Gene Silencing", Planta, 216(4): 686-691, 2003. Results and Discussion.

Antonious "Production and Quantification of Methyl Ketones in Wild Tomato Accessions", Journal of Environmental Science and Health, Part B, 36(6): 835-848, 2001.

Clough et al. "Floral Dip: a Simplified Method for Agrobacterium-Mediated Transformation of *Arabidopsis thaliana*", The Plant Journal, 16(6): 735-743, Dec. 1998.

Desfeux et al. "Female Reproductive Tissues Are the Primary Target of Agrobacterium-Mediated Transformation by the *Arabidopsis* Floral-Dip Method," Plant Physiology, 123: 895-904, Jul. 2000.

Dominguez et al. "Gene Walking by Unpredictably Primed PCR," Nucleic Acids Research, 22(15): 3247-3248, 1994.

Fillatti et al. "Efficient Transfer of a Glyphosate Tolerance Gene into Tomato Using a Binary Agrobacterium Tumefaciens Vector," Nature Biotechnology 5: 726-730, 1987.

Hareven et al. "The Making of a Compound Leaf: Genetic Manipulation of Leaf Architecture in Tomato," Cell, 84: 735-44, Mar. 8, 1996.

Hsu et al. "Analysis of Promoter Activity of Cotton Lipid Transfer Protein Gene LTP6 in Transgenic Tobacco Plants", Plant Science, 143(1): 63-70, May 7, 1999.

Hu et al. "The *Arabidopsis* Auxin-Inducible Gene ARGOS Controls Lateral Organ Size," The Plant Cell, 15(9): 1951-61, Sep. 2003.

Jefferson et al. "GUS Fusions: Beta-Glucuronidase as a Sensitive and Versatile Gene Fusion Marker in Higher Plants", The EMBO Journal, 6(13): 3901-3907, Dec. 20, 1987.

Kennedy "Tomato, Pests, Parasitoids, and Predators: Tritrophic Interactions Involving the Genus Lycopersicon", Annual Review of Entomology, 48: 51-72, Jan. 2003.

Kim et al. "The AtGRF Family of Putative Transcription Factors Is Involved in Leaf and Cotyledon Growth in *Arabidopsis*," Plant Journal, 36(1): 94-104, Oct. 2003.

Kowalski et al. "Purification and Characterization of a Polyphenol Oxidase From the Type A Glandular Trichomes of Solanum Berthaultii", Plant Physiology, 100: 677-684, 1992.

Morello et al. "A Long Leader Intron of the Ostub16 Rice Beta-Tubulin Gene is Required for High-Level Gene Expression and Can Autonomously Promote Transcription Both In Vivo and In Vitro", The Plant Journal, 29(1): 33-44, Jan. 2002.

Perez-Estrada et al. "Variation in Leaf Trichomes of Wigandia Urens: Environmental Factors and Physiological Consequences", Tree Physiology, 20(9): 629-632, May 9, 2000.

Philiips et al. "Resin-Based Defenses in Conifers", Trends in Plant Sciense, 4(5): 184-190, May 1, 1999.

Rose et al. "Introns Act Post-Transcriptionally to Increase Expression of the *Arabidopsis thaliana* Tryptophan Pathway Gene PAT1", The Plant Journal, 11(3): 455-464, 1997.

Smith et al. "The Interaction of Two Homeobox Genes, BREVIPEDICELLUS and PENNYWISE, Regulates Internode Patterning in the *Arabidopsis* Inflorescence," The Plant Cell, 15: 1717-27, Aug. 2003.

Sommer et al. "Import, Targeting and Processing of a Plant Polyphenol Oxidase", Plant Physiology, 105: 1301-1311, Aug. 1994.

Sorefan et al. "MAX4 and RMS1 Are Orthologous Dioxygenase-Like Genes that Regulate Shoot Branching in *Arabidopsis* and Pea," Genes and Development, 17: 1469-74, 2003.

Thipyapong et al. "Differential Expression and Turnover of the Tomato Polyphenol Oxidase Gene Family during Vegetative and Reproductive Development", 113(3): 707-718, Mar. 1997.

Wagner "Secreting Glandular Trichomes: More Than Just Hairs", Plant Physiology, 96: 675-679, 1991.

Wang et al. "Isolation and Characterization of the CYP71D16 Trichome-Specific Promoter From *Nicotiana tabacum* L.", Journal of Experimental Botany, 53(376): 1891-1897, Sep. 1, 2002.

Wang et al. "Suppression of a P450 Hydroxylase Gene in Plant Trichome Glands Enhances Natural-Product-Based Aphid Resistance", Nature Biotechnology, 19: 371-374, Apr. 1, 2001.

Yu et al. "Comparison of Polyphenol Oxidase Expression in Glandular Trichomes of Solanum and Lycopersicon Species", Plant Physiology, 100(4): 1885-1890, Dec. 1992.

* cited by examiner

W.T.

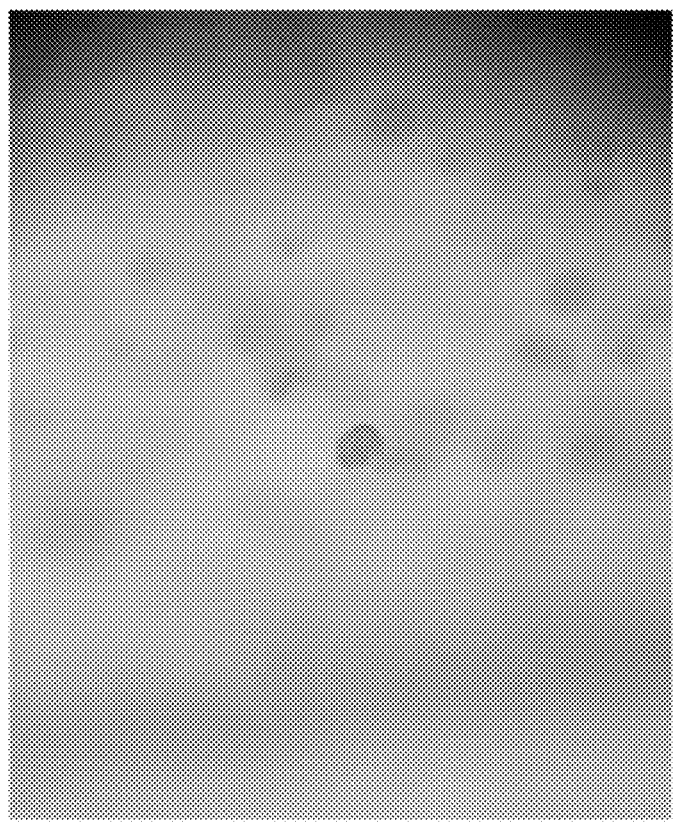
Fig. 1h  TR27P

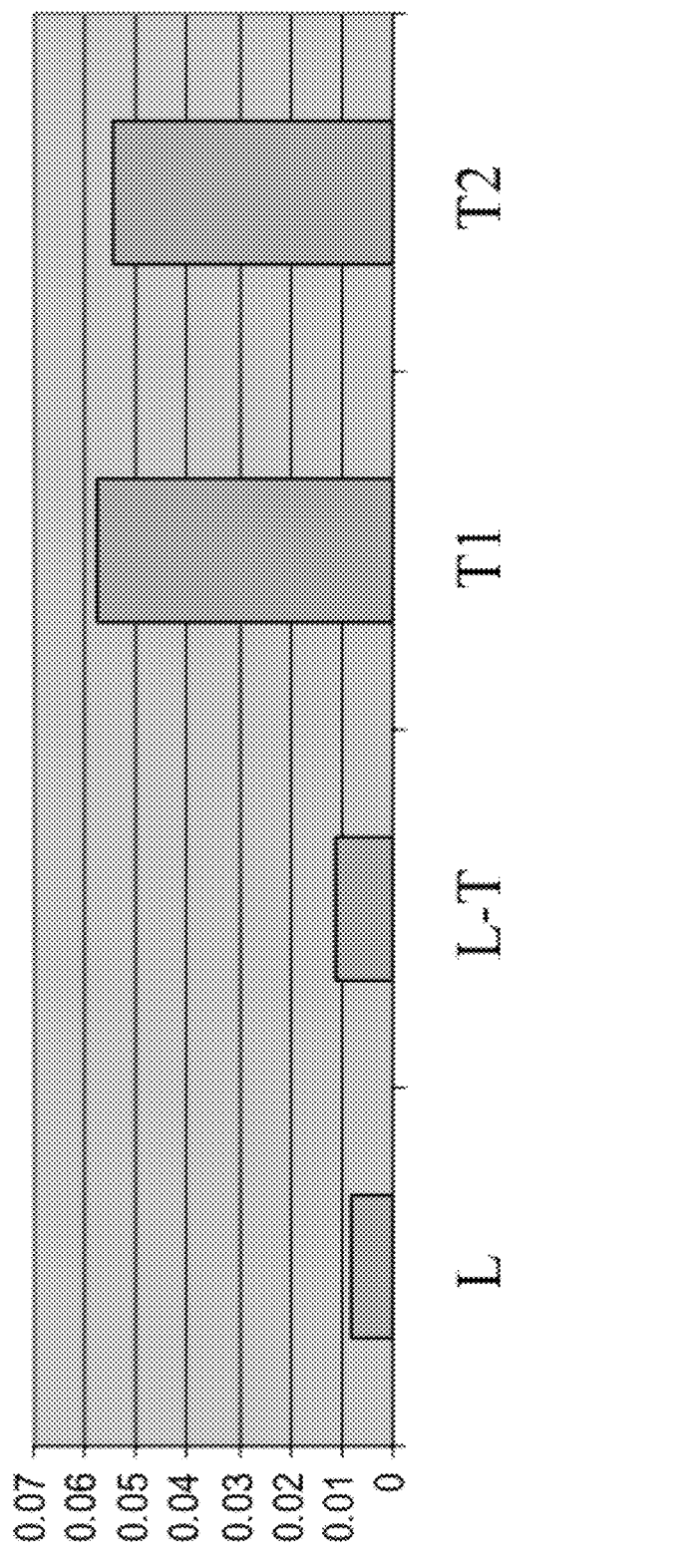

```
                        SEQUENCE LISTING

<160> NUMBER OF SEQ ID NOS: 88

<210> SEQ ID NO 1
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 1
atggaagtaa ctttgttgta tagtac                                          26

<210> SEQ ID NO 2
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 2
gccagtgatc accataagga g                                               21

<210> SEQ ID NO 3
<211> LENGTH: 376
<212> TYPE: DNA
<213> ORGANISM: Lycopersicon hirsutum

<400> SEQUENCE: 3
atggaagtaa ctttgttgta tagtacttca ctctctattt tgtttgtgct tctacttgtt     60
```

```
aaacttgttt catcaaaacg aagaaaacag aatctaccac caagcccact acttaaactt      120
ccaatattag gccatctcta tctccttaaa ccacmtctat atcgcactct tgctaatctc      180
tcaactaaat atggccctgt tttctctctt caattaggta cccgtcttgt tgtagcaatt      240
tcctcaccat ctgctgccga agaatgtttc acaaaaaatg atatcgtttt tgctaatcgc      300
cctcggacaa tgacggcaaa attcataggc tataactcta ctacagtcat tggttctcct      360
tatggtgatc actggc                                                      376

<210> SEQ ID NO 4
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 4
ttctttggtt cttcaatgtt gg                                                22

<210> SEQ ID NO 5
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 5
tttgtaatgt cattgggagg tc                                                22

<210> SEQ ID NO 6
<211> LENGTH: 410
<212> TYPE: DNA
<213> ORGANISM: Gossypium hirsutum

<400> SEQUENCE: 6
ttctttggtt cttcaatgtt ggaaattatc atctccatct ctgattttac aacaaaatac       60
atcaatatcc atgggtgcat tcaaaggtta attacttatg gaattatttt aattttgttc      120
ataccttata tacgtacaca tgaaaaaatt gactattaat tttgtaggta ttcataaact      180
tcaaatccca aattcgcctc tgacagtgtc tgctcgtgga ctcaacaaga tttcatgctc      240
actcaactta caaaccgaaa agctttgtta tgaggataat gataatgatc ttgatgaaga      300
acttatgcct aaacacattg ctttgataat ggatggtaat aggagatggg caaaggataa      360
gggtttagaa gtatatgaag gtcacaaaca tattattcca aaattaaaag                 410

<210> SEQ ID NO 7
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 7
gggtaatatt catttgatttt tcc                                              23

<210> SEQ ID NO 8
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 8
```

```
aacctgctttt acatgtttca ag                                              22
```

<210> SEQ ID NO 9
<211> LENGTH: 431
<212> TYPE: DNA
<213> ORGANISM: Gossypium hirsutum

<400> SEQUENCE: 9

```
gggtaatatt catttgattt tcccactttt atttatatct tgtttcattt tcccatccac      60
aacaaatggc tactccaacg caatcataaa agcttggtgc acccaaacac ctcatccaca     120
accttgtgaa tacttcttat cacaaaatcc caaaattaca tctcctatca taaaaaaatc     180
agattttcta aaagtgtcac tagacttagt gttagaccgt gcgttacgtg cccaactgaa     240
cacatattca ctaggtccaa aatgtcgtaa cgagcgcgaa aaaaacgcat gggctgattg     300
cattgaactc tatgaaaact caatcaacaa aatcaaaagc acagttgatc caaacacaaa     360
atgctcagct actgatgctc aaacatggtt aagtacatcc ttaacaaatc ttgaaacatg     420
taaagcaggt t                                                          431
```

<210> SEQ ID NO 10
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 10

```
tttttttttt tgtttgttgt gggggtgt                                         28
```

<210> SEQ ID NO 11
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 11

```
ggaagtttaa gtagtgggct tg                                               22
```

<210> SEQ ID NO 12
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 12

```
tttttgtttg ttgtggg                                                     17
```

<210> SEQ ID NO 13
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 13

```
gtgggcttgg tggtagattc                                                  20
```

<210> SEQ ID NO 14
<211> LENGTH: 3284
<212> TYPE: DNA
<213> ORGANISM: Lycopersicon hirsutum

<400> SEQUENCE: 14

```
ttttgtttg ttgtgggggt gtcgctcagc ccctactcat ccaagggtta ttcaaaaaat      60
aaaataaaaa taattgcatc aattttaaaa aaaaaagat ggcaaattga caatcatatt     120
aaagatggta ggtgtaactt cactacatta tttattgtgt cctttaagag ctcaaatcct    180
ttgctttctt aaataaaaat aaaaaagca agaaaattat actaactcct atttcacagg    240
gcctccattg aagtcttttg atttggtagt tgataaagtt ataaccgaat gactaagagc    300
ctgtttggat cagtttaaaa gctggtcaaa ctgacttaca agctgatttt tgacttattt    360
agctgtttga caatactgaa ataacttat tttaagttaa aaaaaaata ttattttaag     420
ccaaaagtta aaagttgggg gagaggtgct tttctttttt agcttataag ttgttttaag    480
ttgaccacat ttttatgttt ttgcccttaa tattttata caatctccaa attagaacat    540
aaccctaaca tctctttctt ccattttcc cttttcacgt ttgacatagc aacttcagca    600
cttttatcca aacacataac tgctatattt taaaaataag tttcagcact ttcaaaagta   660
cttttttaaa gttgctttta ttaagcccat ccaaacgcgc cctaataaat ctctttaact    720
ttgtcgtata ttagctctat atttcaacaa atatagttta tctttattct taacgtattc    780
atgttctttt caatttgtct tatttattac tattatatga ttatagtttt ttatacatat    840
gatatgtttc gtctagagta agtcatgttt tatctagaat aagtctattt taaacaaaat    900
gtaattcaat tagtatgaaa atattttct ctatatattt taatgtaatg tcttttttt     960
ggatgccatg tctttattta cttctttttt cgatttgaaa ttgtaatttt ttttataaat   1020
ttgatggtat accgctcaaa cattttgtaa tattttatt tatacgtatc tttttttata   1080
gacaatttat ttttgatta ttaaaattta tgtttagtaa ttaaaatatg ttaattcctc    1140
tgataaaata aatgtttata tttcatgaag tattcaatat atcagacctc caacatctaa    1200
cacaagattt tcatgttata ttttgtgtaa agttatattc ttatgttaaa cttacatacg    1260
aaaggattta gatttaaact tagctatata aattaaaatt ttctaatatc aattagggga    1320
taaacgtgtg atgcacgcac gttccgagaa ttagttatta ttattaatat atgaagtctt    1380
attgatcaaa atcacgcac gttccgagaa ttagttatta ttattaatat atgaagtctt     1440
attgatcaaa agaaaaaaa ctcacaaaat acgccaacgc atactttcta ttttaatacg    1500
ctttgcatag ataaaaatat ttgtaggatt ttgtgttact actattagtc cattactatg    1560
acctattgtg aaaagtgaaa acatgatttt tacaaaagaa tctcttaata aaatttattg    1620
attattattt cttctaggc ggggaaaat aagtagtttg ataaatattt ttttaagaat      1680
ttgtgatttt taattgttcg aaagttaaaa ccttatagtt agcttacatc tcatattaat    1740
tttaccacta ttgcaatatt ttcatatcta aactatgctt ttctatgaat ttcttttaatt   1800
cttttaaatt ttcttaaaat cttaatatat tttctacata ttttgtatta tattataaat    1860
ttaaaaatat aggggtcat ggcttacgtt gcttttcttg gtcatcactt gattggttct     1920
agaagatgta gatgtatcta tcttggcata caaggctaca aagcagccag agagtcctcg    1980
gaatttttat ttttttact tttcatttt gaaaaagta agaaagtaca tatattttt      2040
ttcttattac actttttgac atatttgtat tgcattaagg tcaagtaaaa aagtgataac    2100
taaatccaaa gagagagtag taatcataca gaaaaattt attacctacg ggatataatt    2160
attatcagtt gtatgaggct tatttagctg ccacatatta aaaagactca cctttcactt    2220
tcatttcatt tccttatctc tttttatttta accttttct tctgtacttt tactctcttc    2280
ccaactcttt cttgtctttt tctatttgtt attaacattt aatataattt tatttttttc    2340
```

```
aatccgacat tgcattaaa attagaatat tttaaattta aaattgtgta aggctttatt    2400
caaagaaata tataatctat caaaaaagaa tttcatattc aaaatttgaa ctcgagactt    2460
ctaattaagt aagaaataaa tatcatcctg tactccatca tatatttgag gaaaaaccaa    2520
aataggtgtg tagaaatatt taaaattaat ttttttggat gagttttaag gaattgaaga    2580
aagtgcaaca acaaaaaata ataattgtga aattaatttt tgttttttgc atttattttc    2640
taatttgatt tttttgaata atatcaaaag tgcactttat atatataaaa ctcattaaac    2700
aattaaattt gaatttttaa ctattcatca aacaattgat ggggttcttg cttaactaga    2760
ggttttaagt ttcaaatttt aaatacaaaa aattcttgtt gacaacatat aatcgaattt    2820
taacacaaat attgaatata aaataaaata taagaagagt taataagtag gggaaaaaat    2880
gaagaacagt tgggaggaaa aagacggtaa aaaaaagggt taaaaatgaa agaaaaagga    2940
aatgtaatga aatgaagtga aatatggatc ccattaacac gttgcagcca acaaggcct     3000 tatacaaccg acaataatta tatctcgctt aaaataaaat ttttgtatc acgcgtaata     3060 aatttgaacc aatattttct tgagtggacc cataagttga aaagtctagg ctggttcaac    3120
agccccatca tctatactat tatatataaa ccaattcagt gcaacaagtt gagatatgga    3180
agtaactttg ttgtatagta cttcactctc tattttgttt gtgcttctac ttgttaaact    3240
tgtttcatca aaacgaagaa aacagaatct accaccaagc ccac                     3284

<210> SEQ ID NO 15
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 15
gttgagtcca cgagcagaca c                                               21

<210> SEQ ID NO 16
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 16
cgagcagaca ctgtcagagg                                                 20

<210> SEQ ID NO 17
<211> LENGTH: 1337
<212> TYPE: DNA
<213> ORGANISM: Lycopersicon hirsutum

<400> SEQUENCE: 17
tttttgtttg ttgtgggggt gttaaatggt gggttgggtt gaaattggaa atattacaat     60
gggtttgaat agaaattggg ttgggttaga cccgcccaaa tttactttga actcaaatga    120
gctaaaaata ggttgggcct tgacccgccc aatttgatcc gattaatctt agttatttaa    180
catattgata tttaactttt ataatcacat tttgaagttc cgttcaagaa ttttttgtta    240
aaaaaagtaa caaatggata gataaatcat aaaaaaggca acaaatcgat aataattttat   300 attgtaaata taggaacata tcttaatact aagttctaaa acgggttgaa attggagatt    360
gaattaggct taattgagaa ttctcttcaa ataggttaag cttgaatggg tcgagattga    420
acccaattca aattatcttg agcccaaccc ttaaaattct gggcgaattg ggcatgttac    480
```

```
catgtttggg ttcattttta acgccccctag cgtagtcgaa agaagtcaat ccatgaggtt    540
tgtaaaacaa atgcgaataa tttaccctac cattgagctt gttagtcata tggtgtagca    600
aaatggtaga ttatcgaaaa aatatcttaa ttatgcttca tagttataat ttgttaatta    660
caattagtag ctacatgtta tatggaggag agtggtgagc gagattggga gaggaaagag    720
agaagtgagt gagacaaggt agagagtggg agagaggcga actgcatatg catatttgtc    780
aaaataattg tatatatgta actggtatac atacgtattc gtatatctgg tgagtgagga    840
gagaaaagag agaagcgagc gagattggaa gaggaaagag agagccgagc gagagaggac    900
aataatttat gtaattcgca tctcatttgt ataattaatt ttgttcgaaa tgcggttcaa    960
tataatttt taaccataag cataaacaac cctatataga actattgatc aatatagaac    1020
tattgatcta ttgatcaaaa gagtcatacc ataattctat ttaaacacca cctcccttgt    1080
ttcacttcac aataaaataa atttgagtaa taaagcatga gttctttggt tcttcaatgt    1140
tggaaattat catctccatc tctgatttta caacaaaata catcaatatc catgggtgca    1200
ttcaaaggtt aattacttat gggaattatt taattttgtt cataccttat atacgtacac    1260
atgaaaaaat tgactattaa ttttgtaggt attcataaac ttcaaatccc aaattcgcct    1320
ctgacagtgt ctgctcg                                                   1337
```

<210> SEQ ID NO 18
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 18
attcacaagg ttgtggatga gg                                              22

<210> SEQ ID NO 19
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 19
gatgaggtgt ttgggtgcac                                                 20

<210> SEQ ID NO 20
<211> LENGTH: 1906
<212> TYPE: DNA
<213> ORGANISM: Gossypium hirsutum

<400> SEQUENCE: 20

```
ttttttgtttg ttgtgggggt gtcattgagt cttttcaagg tgtgaatctt ttaacgaaaa    60
gacctgctct gataccaatt gaagaaacct taccccagaa cacgaaccag gttcgtgtaa   120
gttgctttta agtaaagaca gagtaaagac acaaacactt attgaattaa aaaccttcct   180
cgctcaagga aggaaaaacc tcgttttatt aattcaacta taagatttg tgattacaac    240
tcaataatca aaaagtctta tctctactac tccctcgatt gactccaatc gatctctcca   300
aaaggtcaaa cccacctttt gttacaattc tcacagaaac tcaaccctac aaagagccaa   360
acccactcct tgtacaactc tcacagaaac acaaccctac aagaagtcaa acccactcct   420
tgtacaactc tcacagaaac tcaaccctac aagaagccaa acccactcct tgtacaataa   480
ctcgtaactt acaatcaaga acgaaacaag aagatagttt tacacgttga aaaccttctc   540
```

-continued

```
actcaagaat gttttaaacg tagtaatcct atcaaccttg aagacttcaa tttgataaat      600
aattctccct tgttctctgc gtgaagtcgt cgttttcttc ctctgcctcg tgctcttctt      660
atagagtttg ttttgccttg tgcaatcctt tttgataagg taaggaagtt atgtttaaac      720
aagaattccc ttttaaagta caatccttat tatatacaac ttccttcctt aataatatat      780
ttaaggtttt ccttatttgt atcaacttat acctttaata tattattttt ggctttgaca      840
aataactcta ttttcttgat tacttggctg acccacttta ctcgatcttg gactcgagct      900
tggcttcttt tgctgcgtac atttgctact gattatttgc gcttcttgtc tatcatcaaa      960
acatgaatta tcgattcaat catattctat cagctactat ttagttggaa tgtttgagaa     1020
cacacaaaag ttttcaaaa cttgaactga aatgtctaat aaaaacactc tatctatcat       1080 attttagat ctcaattgaa ataacatatt atgattcgat tctctaaaaa taaaaatttc       1140
gtagctttaa gagattatta atatattaag tgataattta atgttagtta attagttaaa     1200
atctaacgtg tggtaggtaa tacatatagg aatacgccct ctctagcttc ctgttttcca     1260 cttttttaaag ttggttcctt gtttcatcag tttaatttcc ttatcaagtc atcaaacaca    1320
cataattacc cgcagaattt taatttttt ttaattatta catttatgat tagattattt       1380
tcttccaaaa cctaagaaat agccacacac gtatggttct cactattcat gccttaagga     1440 aaaaaataa aaagaggat ggtgcatccc catcacttag tttttgacat tccgttgtac        1500
ctcttatatt cctatatcta tataaagaac ccaaaagaca ccaaatacaa tcacagtctc     1560
tctcaaaaaa aaaaaacata ttacaaactc cttacgatgg gtaatattca tttgattttc     1620
ccacttttat ttatatcttg tttcattttc ccatccacaa caaatggcta ctccaacgca     1680
atcataaaag cttggtgcac ccaaacacct catccacaac cttgtgaata cttcttatca     1740
caaaatccca aaattcatc tcctatcata aaaaaatcag attttctaaa agtgtcacta      1800
gacttagtgt tagaccgtgc gttacgtgcc caactgaaca catattcact aggtccaaaa     1860
tgtcgtaacg agcgcgaaaa aaacgcatgg gctgattgca ttgaac                    1906

<210> SEQ ID NO 21
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 21
aatttaagct tgtgtcgctc agcccctact c                                      31

<210> SEQ ID NO 22
<211> LENGTH: 35
<212> TYPE: DNA
<213> ORGANISM: Artificial sequence
<220> FEATURE:
<223> OTHER INFORMATION: Single strand DNA oligonucleotide

<400> SEQUENCE: 22
aaattgtcga catctcaact tgttgcactg aattg                                  35

<210> SEQ ID NO 23
<211> LENGTH: 3157
<212> TYPE: DNA
<213> ORGANISM: Lycopersicon hirsutum

<400> SEQUENCE: 23
gtgtcgctca gcccctactc atccaagggt tattcaaaaa ataaaataaa ataattgca        60
```

```
tcaattttaa aaaaaaaaag atggcaaatt gacaatcata ttaaagatgg taggtgtaac    120
ttcactacat tatttattgt gtcctttaag agctcaaatc ctttgctttc ttaaataaaa    180
ataaaaaaag caagaaaatt atactaactc ctatttcaca gggcctccat tgaagtcttt    240
tgatttggta gttgataaag ttataaccga atgactaaga gcctgtttgg atcagtttaa    300
aagctggtca aactgactta caagctgatt tttgacttat ttagctgttt gacaatactg    360
aaaataactt attttaagtt aaaaaaaaaa tattattttta agccaaaagt taaaagttgg    420
gggagaggtg cttttctttt ttagcttata agttgtttta agttgaccac attttttatgt    480 ttttgccctt aatattttta tacaatctcc aaattagaac ataaccctaa catctctttc    540
ttccattttt cccttttcac gtttgacata gcaacttcag cacttttatc caaacacata    600
actgctatat tttaaaaata agtttcagca ctttcaaaag tactttttta aagttgcttt    660
tattaagccc atccaaacgc gccctaataa atctctttaa ctttgtcgta tattagctct    720
atatttcaac aaatatagtt tatcttatt cttaacgtat tcatgttctt ttcaatttgt    780
cttatttatt actattatat gattatagtt ttttatacat atgatatgtt tcgtctagag    840
taagtcatgt tttatctaga ataagtctat tttaaacaaa atgtaattca attagtatga    900
aaatattttt ctctatatat tttaatgtaa tgtcttttttt ttggatgcca tgtctttatt    960
tacttctttt ttcgatttga aattgtaatt ttttttataa atttgatggt ataccgctca   1020
aacattttgt aatattttta tttatacgta tctttttta tagacaattt attttttgat   1080
tattaaaatt tatgtttagt aattaaaata tgttaattcc tctgataaaa taaatgttta   1140
tatttcatga agtattcaat atatcagacc tccaacatct aacacaagat tttcatgtta   1200
tattttgtgt aaagttatat tcttatgtta aacttacata cgaaaggatt tagatttaaa   1260
cttagctata taaattaaaa ttttctaata tcaattaggg gataaacgtg tgatgcacgc   1320
acgttccgag aattagttat tattattaat atatgaagtc ttattgatca aaaatcacgc   1380
acgttccgag aattagttat tattattaat atatgaagtc ttattgatca aaaagaaaaa   1440
aactcacaaa atacgccaac gcatactttc tattttaata cgctttgcat agataaaaat   1500
atttgtagga ttttgtgtta ctactattag tccattacta tgacctattg tgaaaagtga   1560
aaacatgatt tttacaaaag aatctcttaa taaaatttat tgattattat ttctttctag   1620
gcgggggaaa ataagtagtt tgataaatat tttttaaga atttgtgatt tttaattgtt   1680
cgaaagttaa aaccttatag ttagcttaca tctcatatta attttaccac tattgcaata   1740
ttttcatatc taaactatgc ttttctatga atttctttaa ttcttttaaa ttttcttaaa   1800
atcttaatat atttttctaca tattttgtat tatattataa atttaaaaat atagggggtc   1860
atggcttacg ttgcttttct tggtcatcac ttgattggtt ctagaagatg tagatgtatc   1920
tatcttggca tacaaggcta caaagcagcc agagagtcct cggaattttt attttttta   1980 cttttcattt ttgaaaaaag taagaaagta catatatttt ttttcttatt acactttttg   2040
acatatttgt attgcattaa ggtcaagtaa aaaagtgata actaaatcca aagagagagt   2100
agtaatcata cagaaaaaat ttattaccta cgggatataa ttattatcag ttgtatgagg   2160
cttatttagc tgccacatat taaaaagact caccttcac tttcatttca tttccttatc   2220
tcttttattt taacctttt cttctgtact tttactctct tcccaactct tcttgtctt   2280 tttctatttg ttattaacat ttaatataat tttatttttt tcaatccgac atttgcatta   2340
aaattagaat attttaaatt taaaattgtg taaggcttta ttcaaagaaa tatataatct   2400
atcaaaaaag aatttcatat tcaaaatttg aactcgagac ttctaattaa gtaagaaata   2460
```

-continued

| aatatcatcc tgtactccat catatatttg aggaaaaacc aaaataggtg tgtagaaata | 2520 |
| --- | --- |
| tttaaaatta attttttttgg atgagtttta aggaattgaa gaaagtgcaa caacaaaaaa | 2580 |
| taataattgt gaaattaatt ttttgttttt gcatttattt tctaatttga ttttttttgaa | 2640 |
| taatatcaaa agtgcactt atatatataa aactcattaa acaattaaat ttgaatttt | 2700 |
| aactattcat caaacaattg atggggttct tgcttaacta gaggttttaa gtttcaaatt | 2760 |
| ttaaatacaa aaaattcttg ttgacaacat ataatcgaat tttaacacaa atattgaata | 2820 |
| taaaataaaa tataagaaga gttaataagt aggggaaaaa atgaagaaca gttgggagga | 2880 |
| aaaagacggt aaaaaaaagg gttaaaaatg aagaaaaag gaaatgtaat gaaatgaagt | 2940 |
| gaaatatgga tcccattaac acgttgcagc caaacaaggc cttatacaac cgacaataat | 3000 |
| tatatctcgc ttaaaataaa attttttgta tcacgcgtaa taaatttgaa ccaatatttt | 3060 |
| cttgagtgga cccataagtt gaaaagtcta ggctggttca acagcccat catctatact | 3120 |
| attatatata aaccaattca gtgcaacaag ttgagat | 3157 |

<210> SEQ ID NO 24
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 24

| cctagtcgac ggtgttaaat ggtgggttgg | 30 |
| --- | --- |

<210> SEQ ID NO 25
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 25

| ttggatccga gcagacactg tcagagg | 27 |
| --- | --- |

<210> SEQ ID NO 26
<211> LENGTH: 1320
<212> TYPE: DNA
<213> ORGANISM: Lycopersicon hirsutum

<400> SEQUENCE: 26

| ggtgttaaat ggtgggttgg gttgaaattg gaaatattac aatgggtttg aatagaaatt | 60 |
| --- | --- |
| gggttgggtt agacccgccc aaatttactt tgaactcaaa tgagctaaaa ataggttggg | 120 |
| ccttgacccg cccaatttga tccgattaat cttagttatt taacatattg atatttaact | 180 |
| tttataatca cattttgaag ttccgttcaa gattttttg ttaaaaaaag taacaaatgg | 240 |
| atagataaat cataaaaaag gcaacaaatc gataataatt tatattgtaa atataggaac | 300 |
| atatcttaat actaagttct aaaacgggtt gaaattggag attgaattag cttaattga | 360 |
| gaattctctt caaataggtt aagcttgaat gggtcgagat tgaacccaat tcaaattatc | 420 |
| ttgagcccaa cccttaaaat tctgggcgaa ttgggcatgt taccatgttt gggttcattt | 480 |
| ttaacgcccc tagcgtagtc gaaagaagtc aatccatgag gtttgtaaaa caaatgcgaa | 540 |
| taatttaccc taccattgag cttgttagtc atatggtgta gcaaaatggt agattatcga | 600 |
| aaaaatatct taattatgct tcatagttat aatttgttaa ttacaattag tagctacatg | 660 |
| ttatatggag gagagtggtg agcgagattg ggagaggaaa gagagaagtg agtgagacaa | 720 |

| | |
|---|---|
| ggtagagagt gggagagagg cgaactgcat atgcatattt gtcaaaataa ttgtatatat | 780 |
| gtaactggta tacatacgta ttcgtatatc tggtgagtga ggagagaaaa gagagaagcg | 840 |
| agcgagattg gaagaggaaa gagagagccg agcgagagag gacaataatt tatgtaattc | 900 |
| gcatctcatt tgtataatta attttgttcg aaatgcggtt caatataatt ttttaaccat | 960 |
| aagcataaac aaccctatat agaactattg atcaatatag aactattgat ctattgatca | 1020 |
| aaagagtcat accataattc tatttaaaca ccacctccct tgtttcactt cacaataaaa | 1080 |
| taaatttgag taataaagca tgagttcttt ggttcttcaa tgttggaaat tatcatctcc | 1140 |
| atctctgatt ttacaacaaa atacatcaat atccatgggt gcattcaaag gttaattact | 1200 |
| tatgggaatt atttaatttt gttcatacct tatatacgta cacatgaaaa aattgactat | 1260 |
| taattttgta ggtattcata aacttcaaat cccaaattcg cctctgacag tgtctgctcg | 1320 |

<210> SEQ ID NO 27
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 27

| | |
|---|---|
| tttccaagct tgacctgctc tgataccaat tg | 32 |

<210> SEQ ID NO 28
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 28

| | |
|---|---|
| ccggatcctc gtaaggagtt tgtaatatg | 29 |

<210> SEQ ID NO 29
<211> LENGTH: 1537
<212> TYPE: DNA
<213> ORGANISM: Lycopersicon hirsutum

<400> SEQUENCE: 29

| | |
|---|---|
| gacctgctct gataccaatt gaagaaacct taccccagaa cacgaaccag gttcgtgtaa | 60 |
| gttgctttta agtaaagaca gagtaaagac acaaacactt attgaattaa aaaccttcct | 120 |
| cgctcaagga aggaaaaacc tcgttttatt aattcaacta taagattttg tgattacaac | 180 |
| tcaataatca aaaagtctta tctctactac tccctcgatt gactccaatc gatctctcca | 240 |
| aaaggtcaaa cccacctttt gttacaattc tcacagaaac tcaaccctac aaagagccaa | 300 |
| acccactcct tgtacaactc tcacagaaac acaaccctac aagaagtcaa acccactcct | 360 |
| tgtacaactc tcacagaaac tcaaccctac aagaagccaa acccactcct tgtacaataa | 420 |
| ctcgtaactt acaatcaaga acgaaacaag aagatagttt tacacgttga aaaccttctc | 480 |
| actcaagaat gttttaaacg tagtaatcct atcaaccttg aagacttcaa tttgataaat | 540 |
| aattctccct tgttctctgc gtgaagtcgt cgttttcttc ctctgcctcg tgctcttctt | 600 |
| atagagtttg ttttgccttg tgcaatcctt tttgataagg taaggaagtt atgtttaaac | 660 |
| aagaattccc ttttaaagta caatccttat tatatacaac ttccttcctt aataatatat | 720 |
| ttaaggtttt ccttatttgt atcaacttat accttttaata tattattttt ggctttgaca | 780 |
| aataactcta ttttcttgat tacttggctg acccactttta ctcgatcttg gactcgagct | 840 |

```
tggcttcttt tgctgcgtac atttgctact gattatttgc gcttcttgtc tatcatcaaa      900
acatgaatta tcgattcaat catattctat cagctactat ttagttggaa tgtttgagaa      960
cacacaaaag ttttcaaaa cttgaactga aatgtctaat aaaaacactc tatctatcat     1020 attttagat ctcaattgaa ataacatatt atgattcgat tctctaaaaa taaaaatttc     1080
gtagctttaa gagattatta atatattaag tgataattta atgttagtta attagttaaa     1140
atctaacgtg tggtaggtaa tacatatagg aatacgccct ctctagcttc ctgttttcca     1200 cttttaaag ttggttcctt gtttcatcag tttaatttcc ttatcaagtc atcaaacaca     1260
cataattacc cgcagaattt taatttttt ttaattatta catttatgat tagattattt     1320
tcttccaaaa cctaagaaat agccacacac gtatggttct cactattcat gccttaagga     1380 aaaaaataa aaagaggat ggtgcatccc catcacttag tttttgacat tccgttgtac     1440
ctcttatatt cctatatcta tataaagaac ccaaaagaca ccaaatacaa tcacagtctc     1500
tctcaaaaaa aaaaaacata ttacaaactc cttacga                              1537

<210> SEQ ID NO 30
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 30
aaatctagac taccatcgct agtaatcgtg                                        30

<210> SEQ ID NO 31
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 31
gttgaagaac tgcatcccgg gagg                                              24

<210> SEQ ID NO 32
<211> LENGTH: 1834
<212> TYPE: DNA
<213> ORGANISM: Nicotiana tabacum

<400> SEQUENCE: 32
tctagactac catcgctagt aatcgtggca ataactaccc taactatagc atttattgct       60
accaaataaa atttggcagc taatcataat tttttgtcat gaatcaatag ttattgtagc      120
aatagttatc tcttagccac aataaattat ttaaataaaa atattatagc taaataaata      180
tttttgcttt aagttctaaa agcttgtggc aatagttaaa tgatatagtc acagatttat      240
tggtataatt gaattatgtt gctaatttct tagttttttg ccacgagtta aaaattacca      300
atagctatag taactttta atcacaataa aatatttgaa agaaatatt gtagctaaat      360 gaatattttt tccttcaagt tattaaaagt tgtggcaata taggtaaat tagccacatg      420 tttcttgctt taatagaatt ttgtagctaa tcattaactt ttaccacgag ttgaacttaa      480
tataacaaca ataaccttt aaccataata aagcgattta aatcaaatat tactaaataa      540
ataactttgc tttcaagttt ctataaaatc atggcaatag tcattacgat aaaatgatat      600
aaccacgaat atattgcaac gataaattct gtaactaatc attagttttt gcgacgaggt      660 aaatttccg tcacagtagc aatcttctag gcacattaaa aatttgaaac aaaattttgt      720
```

```
agtcaaataa atatttatct tcttatttta agaaaataaa aatagttaga taatagttac      780
tactatttgt catgaaaata tcaatagata caaatttaaa gtgactataa atttacgagt      840
ttactatact ttagtcgtac agtttgcaat aatagtattt taaccacaat tagttatatg      900
tacaaaataa cataagtgaa taactttttt tcatgagaaa aataagagtt gctcaaacaa      960
tatcaagtta caaaattta attttaactg taaaagttat attttccaa aataacataa      1020 actatagtaa ttatatatag tttgaagtat taataaaatt taaatatgca aaagttaatt     1080
ttaataaacc atttgtatgc ctaacttgta gcctctaaac tattttattt gctttattta     1140
tcaaactcat attttatttt attgcacctt gttagttttg gacgttaatt atatatattt     1200
ggtgtaaaat ttaaatata ttaacatttg tggagaattt atgtatgcct ggttcttaac     1260
tatttttttt tatataactg gttagagtaa tttcttatat ttcagtattt attttttaaat     1320 aagtcctcat aaattgaaga ctttaaaagt ttttgtgtca ttcctctttt tatttaagaa     1380
attgaagaat tccgctaaat ttcatatttc cgctgttatt taactgttta tttcccttgt     1440
taatataatt ggtaagaagt tttaaaataa aggagttaat gatttctag gttcatggct      1500 tgcctagctt ctacgagtaa gcgccatcac gactcccgag gataaggaaa tccgggtcgt     1560
agcattcact cacaaaaatt actaaaaaca aagtttaccc ttctcccaaa agtaaatttc     1620
atatttggct ccacataatg tgttcaatga gtcaagtgaa gtacttttca tgacaaaaaa     1680
aagttgctga aaaatgcata tctcatattt ttttttaga gaaatccat ttcttgccta      1740 aacgaaagcc tataaaagag catatattgc aacaacagtt tgcagaaact atcaagtcaa     1800
ataatccccc ctttaattcc ctcccaaacc cggg                                1834

<210> SEQ ID NO 33
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 33
aaatctagat aagttgataa agctaatttc tc                                    32

<210> SEQ ID NO 34
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 34
tttcccggga cctggaggca atc                                              23

<210> SEQ ID NO 35
<211> LENGTH: 1969
<212> TYPE: DNA
<213> ORGANISM: Nicotiana tabacum

<400> SEQUENCE: 35
tctagataag ttgataaagc taatttctca ttttagctac catcgctagt aatcgtggca      60
ataactaccc taactatagc atttattgct accaaataaa atttggcagc taatcataat     120
tttttgtcat gaatcaatag ttattgtagc aatagttatc tcttagccac aataaattat     180
ttaaaataaa atattatagc taaataaata ttttgctttt aagttctaaa agcttgtggc     240
aatagttaaa tgatatagtc acagatttat tggtataatt gaattatgtt gctaatttct     300
```

```
tagtttttg ccacgagtta aaaattacca atagctatag taacttttta atcacaataa    360
aatatttgaa agaaaatatt gtagctaaat gaatatttt tccttcaagt tattaaaagt     420
tgtggcaata taggttaaat tagccacatg tttcttgctt aatagaatt ttgtagctaa    480
tcattaactt ttaccacgag ttgaacttaa ataacaaca ataaccttt aaccataata    540
aagcgattta atcaaatat tactaaataa ataactttgc tttcaagttt ctataaaatc    600
atggcaatag tcattacgat aaaatgatat aaccacgaat atattgcaac gataaattct    660
gtaactaatc attagttttt gcgacgaggt aaattttccg tcacagtagc aatcttctag    720
gcacattaaa aatttgaaac aaaattttgt agtcaaataa atatttatct tcttatttta    780
agaaaataaa aatagttaga taatagttac tactatttgt catgaaaata tcaatagata    840
caaatttaaa gtgactataa atttacgagt ttactatact ttagtcgtac agtttgcaat    900
aatagtattt taaccacaat tagttatatg tacaaaataa cataagtgaa taactttttt    960
tcaatgagaa aataagagtt gctcaaacaa tatcaagtta caaaaattta atttttaactg  1020
taaaagttat attttttccaa aataacataa actatagtaa ttatatatag tttgaagtat  1080
taataaaatt taaatatgca aaagttaatt ttaataaacc atttgtatgc ctaacttgta   1140
gcctctaaac tattttatttt gctttatttta tcaaactcat attttatttt attgcacctt  1200
gttagttttg gacgttaatt atatatattt ggtgtaaaat ttaaatatata ttaacatttg   1260
tggagaattt atgtatgcct ggttcttaac tattttttttt tatataactg gttagagtaa  1320
tttcttatat ttcagtattt atttttaaat aagtcctcat aaattgaaga ctttaaaagt  1380
ttttgtgtca ttcctctttt tatttaagaa attgaagaat tccgctaaat ttcatatttc   1440
cgctgttatt taactgttta tttcccttgt taatataatt ggtaagaagt tttaaaataa   1500
aggagttaat gatttctag gttcatggct tgcctagctt ctacgagtaa gcgccatcac   1560
gactcccgag gataaggaaa tccgggtcgt agcattcact cacaaaaatt actaaaaaca   1620
aagtttaccc ttctcccaaa agtaaatttc atatttggct ccacataatg tgttcaatga   1680
gtcaagtgaa gtacttttca tgacaaaaaa aagttgctga aaaatgcata tctcatattt   1740
ttttttaga gaaatcccat ttcttgccta aacgaaagcc tataaaagag catatattgc    1800
aacaacagtt tgcagaaact atcaagtcaa ataatccccc ctttaattcc ctcccaaaat   1860
gcagttcttc aacttctttt cccttttcct ttttgtgtca tttctctttt tatttaagaa   1920
atggaagaat tccaatagcc aaaccaaaag attgcctcca ggtcccggg                1969

<210> SEQ ID NO 36
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 36
tataagcttt aagtttaaat cctattgtag tg                                    32

<210> SEQ ID NO 37
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 37
cggatccatt aatcacaaga aaaac                                            25
```

<210> SEQ ID NO 38
<211> LENGTH: 625
<212> TYPE: DNA
<213> ORGANISM: Gossypium hirsutum

<400> SEQUENCE: 38

```
aagctttaag tttaaatcct attgtagtgt tatttataaa aaaatgaga aagataaaa        60
atacctttat attaatattt gttatattgt aaaataagga tatttttaac aaattttcaa     120
ttgaatagat gtttgggtga atcctaatac caattaaagt atatatacac aaacaattat    180
aaatcaaatt acctttaata aaatggtatc attcaattca atgacaataa atgcatttat    240
aaatacatca aatgtaaatc tcatgtttat aagaaaacac gtagaaaaaa gttaaaccaa    300
tatttgagtc ctagctgtgg aggcatgatt gagtgaaatc aaatggacgc tggttttaat    360
tgtattgaaa gaaaccaata atcacgtagg ttggcagttg aacataattg aatggtctca    420
acttttaatg tggtgttaat gtttggatcg gataatctca acttacctaa tagctaggaa    480
agtaaaattc aaacatcacc cgctactact tttggctata aaaaccctcc taccctcaag    540
ccctaaccac gacaatcacc aatagtacta ctactccaag caagtatttt ccttacacgt    600
ttgttttcct tgtgataatg gatcc                                           625
```

<210> SEQ ID NO 39
<211> LENGTH: 627
<212> TYPE: DNA
<213> ORGANISM: Gossypium barbadense

<400> SEQUENCE: 39

```
aagctttaag tttaaatcct attgtagtgt tatttataaa aaaatgaga aagataaaa        60
atacctttat attaatattt gttatattat aaaataagga tatttttaac aaattttcaa    120
ttgaatagat gtttgggtga atcctaatac caattaaagt atatatacag caaacaatta    180
taaatcaaat tacttttaat aaaatgctat cattcaattc aatgacaata aatgcattta    240
taaatacatc aaatgtaaat ctcatgttta agaaaaca cgtagaaaaa aagttaaacc     300
aatatttgag tcctagctgt ggaggcatga ttgagtgaaa tcaaatggac gctggtttta    360
attctattga agaaaccaa taatcacgta ggttggcagt tgaacataat tgaatggtct    420
caactttta tgtggtgtta atgtttggat cggataatct caacttacct aatagctagg    480
aaagtaaaat tcaaacatca cccgctacta cttttggcta taaaaaccct cctaccctca    540
agccctaacc acgacaatca ccaatagtac tactactcca agcaagtatt ttccttacac    600
gtttgttttt cttgtgataa tggatcc                                         627
```

<210> SEQ ID NO 40
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 40

```
aaaatttggg atctagaagg tgagg                                            25
```

<210> SEQ ID NO 41
<211> LENGTH: 29
<212> TYPE: DNA
<213> ORGANISM: Artificial sequence
<220> FEATURE:
<223> OTHER INFORMATION: Single strand DNA oligonucleotide -continued

```
<400> SEQUENCE: 41
ctggatccta ttgctagctt tggatgaag                                        29

<210> SEQ ID NO 42
<211> LENGTH: 622
<212> TYPE: DNA
<213> ORGANISM: Lycopersicon pennellii

<400> SEQUENCE: 42
tctagaaggt gaggaacttt ttttaacaat atataagtaa gcattggtta taatttcaca      60
acaacattac ggtaaaacct ctataaatta atacccgata aattaataat ccctctaaaa     120 taatatttttt ctaggatttt cgattagggc aatgaaaaaa atcaccattt tcaataaaat    180
aatgagataa tatattttca gaagacccct atataaatac atgggtccta ttaatatcat    240
aaattgatta ttattcaaaa gcataaatat atctaagata atttagtaaa aaaatgattc    300
tattctgttt ttttttttgtt aaaatttaaa tgtagttgaa gttcatttct aacatttcat    360
attgcttcca agagctccaa ttttgtcttt tcgaacttca ccatagaaga gttccagatg    420
cgataagtgt ttccttacgc gtaattggtt ccaaagttat agtatcatat tcaacttcat    480
catcgacatt gcttttttccg atggtatcca taaattcttc taagcttatt tgaaatggag    540
taatatttta tttggcccca acacattata taaggcaatg tatagcccta tgaatcttca    600
tccaaagcta gcaataggat cc                                              622

<210> SEQ ID NO 43
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 43
atggaaaagc ttatggacag actaaaacac                                      30

<210> SEQ ID NO 44
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 44
ctggatcctg ttgctagctt ttgaatgaaa                                      30

<210> SEQ ID NO 45
<211> LENGTH: 1050
<212> TYPE: DNA
<213> ORGANISM: Lycopersicon esculentum

<400> SEQUENCE: 45
aagcttatgg acagactaaa acactttttt tttttaataa tattgtttgc aagtgtacac      60
cgaaagatct acgttattat aacataatat tacgggtaaa gctagaagtc taattacgaa    120
tttcatgaga tttaataact tttatttttta ttatatttat atttaaaaag tattaaatat    180
atacaaattt aaactcttaa aaccattgtt acaaaattta gaatccaaaa tgttaatatt    240
atggtttcgc ctctgctaaa cattactaat caaaattatc ttttttgttta gagcattact    300 actgtacaaa tctaccaagt ataaaatataa aagctgttaa agaatttccc cacacttatt    360
attcttaatc ttccacctac ccaatcacaa atatattaaa tgagcctcta aatttgccct    420
```

-continued

```
attgcgggta atatgatcta cctatcaatt atttgtaatc tagtcaaaaa gatgccaaaa      480
aaatataata ctccatctag attgaaaatt tttgtcaata gaaaagaaga gaaacatgat      540
aactttataa atattttac ctctggtata gttttgatat agcgtataat aataatatat       600
taatattaat aaatgatgag attagttatc tttagaatgc attctatctt atgtctggtt      660
tgatgtatta atgacaattt tgtttctaca accatgcatt attactgatc aatgtattgt      720
taaatgctaa tacgttgatt tgttatgtat tagttacata tacctatatg ttttgtaata      780
agaaaaatga tgtataacta attaataagt agtattatca tgagtaaagt tattttttctg    840 gtcagtagag agcttctaag aacaaaaact aaataattgt attgtatggc tgctattcaa      900
aattccccac ctaacgcgtc ctggaataat tgatatgact tgaagccgcc tctaaaatta      960
aataatattt ggtgcttata atgttttaca tattatataa agcaaggtat agcccaatga      1020
attttcattc aaaagctagc aacaggatcc                                       1050

<210> SEQ ID NO 46
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 46
aaaatttggg atctagaagg tgagg                                             25

<210> SEQ ID NO 47
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 47 acatgaaaact ttgaatgctt tg                                               22

<210> SEQ ID NO 48
<211> LENGTH: 754
<212> TYPE: DNA
<213> ORGANISM: Lycopersicon pennellii

<400> SEQUENCE: 48
tctagaaggt gaggaacttt ttttaacaat atataagtaa gcattggtta taatttcaca      60
acaacattac ggtaaaacct ctataaatta atacccgata aattaataat ccctctaaaa      120
taatattttt ctaggatttt cgattagggc aatgaaaaaa atcaccattt tcaataaaat      180
aatgagataa tatattttca gaagacccct atataaatac atgggtccta ttaatatcat      240
aaattgatta ttattcaaaa gcataaatat atctaagata atttagtaaa aaaatgattc      300
tattctgttt ttttttttgtt aaatttaaa tgtagttgaa gttcatttct aacatttcat      360
attgcttcca agagctccaa ttttgtcttt tcgaacttca ccatagaaga gttccagatg      420
cgataagtgt ttccttacgc gtaactggtt ccaaagttat agtatcatat tcaacttcat      480
catcgacatt gcttttccg atggtatcca taaattcttc taagcttatt tgaaatggag       540
taatatttta tttggcccca acacattata taaggcaatg tatagcccta tgaatcttcg      600
tccaaagcta gcaataatgs caagtttgtg taatagtagt agtacatctc tcaaaactcc      660
ttttacttct tccaccactt gtttatcttc cactcctaag ccctctcaac ttttcctaca      720
tggaaaacgt aacaaagcat tcaaagtttc atgt                                  754
```

<210> SEQ ID NO 49
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 49
atggaaaagc ttatggacag actaaaacac                              30

<210> SEQ ID NO 50
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 50
ttcccgggac atgaaacttt gaatgctttg                              30

<210> SEQ ID NO 51
<211> LENGTH: 1179
<212> TYPE: DNA
<213> ORGANISM: Lycopersicon esculentum

<400> SEQUENCE: 51
aagcttatgg acagactaaa acactttttt tttttaataa tattgtttgc aagtgtacac    60
cgaaagatct acgttattat aacataatat tacgggtaaa gctagaagtc taattacgaa   120
tttcatgaga tttaataact tttatttttta ttatatttat atttaaaaag tattaaatat   180
atacaaattt aaactcttaa aaccattgtt acaaaattta gaatccaaaa tgttaatatt   240
atggtttcgc ctctgctaaa cattactaat caaaattatc ttttttgttta gagcattact   300 actgtacaaa tctaccaagt ataaatataa aagctgttaa agaatttccc cacacttatt   360
attcttaatc ttccacctac ccaatcacaa atatattaaa tgagcctcta aatttgccct   420
attgcgggta atatgatcta cctatcaatt atttgtaatc tagtcaaaaa gatgccaaaa   480
aaatataata ctccatctag attgaaaatt tttgtcaata gaaagaaga gaaacatgat   540 aactttataa atatttttac ctctggtata gttttgatat agcgtataat aataatatat   600
taatattaat aaatgatgag attagttatc tttagaatgc attctatctt atgtctggtt   660
tgatgtatta atgacaattt tgtttctaca accatgcatt attactgatc aatgtattgt   720
taaatgctaa tacgttgatt tgttatgtat tagttcacata tacctatatg tttttgtaata   780 agaaaaatga tgtataacta attaataagt agtattatca tgagtaaagt tattttttctg   840 gtcagtagag agcttctaag aacaaaaact aaataattgt attgtatggc tgctattcaa   900
aattccccac ctaacgcgtc ctggaataat tgatatgact tgaagccgcc tctaaaatta   960
aataatattt ggtgcttata atgttttaca tattatataa agcaaggtat agcccaatga  1020
attttcattc aaaagctagc aacaatggca agtttgtgta gtaatagtag tactacttct  1080
ctcaaaactc ctttcacttc tttaggttcc actccaaagc cttgtcaact tttcctacat  1140
ggaaaacgta acaaagcatt caaagtttca tgtcccggg                          1179

<210> SEQ ID NO 52
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 52

```
atggaaaagc ttatggacag actaaaacac                                30
```

<210> SEQ ID NO 53
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 53

```
aacccgggag ccgatgcagc taatgg                                    26
```

<210> SEQ ID NO 54
<211> LENGTH: 1299
<212> TYPE: DNA
<213> ORGANISM: Lycopersicon esculentum

<400> SEQUENCE: 54

```
aagcttatgg acagactaaa acactttttt tttttaataa tattgtttgc aagtgtacac    60
cgaaagatct acgttattat aacataatat tacgggtaaa gctagaagtc taattacgaa   120
tttcatgaga tttaataact tttattttta ttatatttat atttaaaaag tattaaatat   180
atacaaattt aaactcttaa aaccattgtt acaaaattta gaatccaaaa tgttaatatt   240
atggtttcgc ctctgctaaa cattactaat caaaattatc ttttgtttta gagcattact   300
actgtacaaa tctaccaagt ataaatataa aagctgttaa agaatttccc cacacttatt   360
attcttaatc ttccacctac ccaatcacaa atatattaaa tgagcctcta aatttgccct   420
attgcgggta atatgatcta cctatcaatt atttgtaatc tagtcaaaaa gatgccaaaa   480
aaatataata ctccatctag attgaaaatt tttgtcaata gaaaagaaga gaaacatgat   540
aactttataa aatattttac ctctggtata gttttgatat agcgtataat aataatatat   600
taatattaat aaatgatgag attagttatc tttagaatgc attctatctt atgtctggtt   660
tgatgtatta atgacaattt tgtttctaca accatgcatt attactgatc aatgtattgt   720
taaatgctaa tacgttgatt tgttatgtat tagttacata tacctatatg ttttgtaata   780
agaaaaatga tgtataacta attaataagt agtattatca tgagtaaagt tattttttctg   840
gtcagtagag agcttctaag aacaaaaact aaataattgt attgtatggc tgctattcaa   900
aattccccac ctaacgcgtc ctggaataat tgatatgact tgaagccgcc tctaaaatta   960
aataatattt ggtgcttata atgttttaca tattatataa agcaaggtat agcccaatga  1020
attttcattc aaaagctagc aacaatggca agtttgtgta gtaatagtag tactacttct  1080
ctcaaaactc ctttcacttc tttaggttcc actccaaagc cttgtcaact tttcctacat  1140
ggaaaacgta acaaagcatt caaagtttca tgcaaggtta ccaatactaa cggtaaccaa  1200
gatgaaacga attctgtaga tcgaaggaat gttcttcttg gcttaggagg tctttatggt  1260
gttgctaatg ctataccatt agctgcatcg gctcccggg                         1299
```

<210> SEQ ID NO 55
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 55

```
gggatgagct acaacttgct tggat                                     25
```

```
<210> SEQ ID NO 56
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 56
ctaggagctc ttcagtttcg gag                                              23

<210> SEQ ID NO 57
<211> LENGTH: 511
<212> TYPE: DNA
<213> ORGANISM: Homo sapiens

<400> SEQUENCE: 57
gggatgagct acaacttgct tggattccta caaagaagca gcaatttcca gtgtcagaag       60
ctcctgtggc aattgaatgg gaggcttgaa tattgcctca aggacaggat gaactttgac      120
atccctgagg agattaagca gctgcagcag ttccagaagg aggacgccgc attgaccatc      180
tatgagatgc tccagaacat ctttgctatt ttcagacaag attcatctag cactggctgg      240
aatgagacta ttgttgagaa cctcctggct aatgtctatc atcagataaa ccatctgaag      300
acagtcctgg aagaaaaact ggagaaagaa gattttacca ggggaaaaact catgagcagt      360 ctgcacctga aagatatta tgggaggatt ctgcattacc tgaaggccaa ggagtacagt       420
cactgtgcct ggaccatagt cagagtggaa atcctaagga acttttactt cattaacaga      480
cttacaggtt acctccgaaa ctgaagagct c                                     511

<210> SEQ ID NO 58
<211> LENGTH: 592
<212> TYPE: DNA
<213> ORGANISM: Artificial sequence
<220> FEATURE:
<223> OTHER INFORMATION: Synthetic human growth hormone gene

<400> SEQUENCE: 58
cccgggatgt tcccaactat tccattgtct aggcttttcg ataatgctat gttgagggct       60
cataggttgc atcagttggc tttcgatact taccaggagt tcgaggaggc ttacattcca      120
aaggagcaga gtactcatt ccttcagaat ccacagactt ctttgtgctt ctctgagtct       180
attccaactc catcaaatag ggaggagact cagcagaagt caaatcttga gttgttgagg      240
atttctttgt tgcttattca gtcttggttg gagccagttc agttcttgag gagtgttttc      300
gcaaattctt tggtttacgg agcttcagat tcaaatgttt acgatttgtt gaaggatttg      360
gaggagggaa ttcagactct tatgggaagg ttggaggatg gatctccaag gactggacag      420
attttcaagc agacttactc taagttcgat acaaactctc ataacgatga tgctttgttg      480
aagaattacg gattgttgta ctgcttcagg aaggatatgg ataaggttga gacttttcttg     540 aggattgttc agtgcaggag tgttgaggga tcttgcggat tctgatgagc tc              592

<210> SEQ ID NO 59
<211> LENGTH: 252
<212> TYPE: DNA
<213> ORGANISM: Artificial sequence
<220> FEATURE:
<223> OTHER INFORMATION: PPOD lumen signal peptide coding sequence

<400> SEQUENCE: 59
atggcaagtt tgtgtagtaa tagtagtact acttctctca aaactccttt cacttcttta       60
```

```
ggttccactc caaagccttg tcaactttc ctacatggaa acgtaacaa agcattcaaa    120 gtttcatgca aggttaccaa tactaacggt aaccaagatg aaacgaattc tgtagatcga    180
aggaatgttc ttcttggctt aggaggtctt tatggtgttg ctaatgctat accattagct    240
gcatcggctc cc                                                         252
```

```
<210> SEQ ID NO 60
<211> LENGTH: 84
<212> TYPE: PRT
<213> ORGANISM: Artificial sequence
<220> FEATURE:
<223> OTHER INFORMATION: PPOD lumen signal peptide sequence

<400> SEQUENCE: 60
```

```
Met Ala Ser Leu Cys Ser Asn Ser Ser Thr Thr Ser Leu Lys Thr Pro
1               5                   10                  15

Phe Thr Ser Leu Gly Ser Thr Pro Lys Pro Cys Gln Leu Phe Leu His
            20                  25                  30

Gly Lys Arg Asn Lys Ala Phe Lys Val Ser Cys Lys Val Thr Asn Thr
        35                  40                  45

Asn Gly Asn Gln Asp Glu Thr Asn Ser Val Asp Arg Arg Asn Val Leu
    50                  55                  60

Leu Gly Leu Gly Gly Leu Tyr Gly Val Ala Asn Ala Ile Pro Leu Ala
65                  70                  75                  80

Ala Ser Ala Pro
```

```
<210> SEQ ID NO 61
<211> LENGTH: 141
<212> TYPE: DNA
<213> ORGANISM: Artificial sequence
<220> FEATURE:
<223> OTHER INFORMATION: PPOA stromal signal peptide coding sequence

<400> SEQUENCE: 61
```

```
atggcaagtt tgtgtaatag tagtagtaca tctctcaaaa ctcctttac ttcttccacc     60 acttgtttat cttccactcc taagccctct caacttttcc tacatggaaa acgtaacaaa    120
gcattcaaag tttcatgtgg g                                              141
```

```
<210> SEQ ID NO 62
<211> LENGTH: 47
<212> TYPE: PRT
<213> ORGANISM: Artificial sequence
<220> FEATURE:
<223> OTHER INFORMATION: PPOA stromal signal peptide sequence

<400> SEQUENCE: 62
```

```
Met Ala Ser Leu Cys Asn Ser Ser Ser Thr Ser Leu Lys Thr Pro Phe
1               5                   10                  15

Thr Ser Ser Thr Thr Cys Leu Ser Ser Thr Pro Lys Pro Ser Gln Leu
            20                  25                  30

Phe Leu His Gly Lys Arg Asn Lys Ala Phe Lys Val Ser Cys Gly
        35                  40                  45
```

```
<210> SEQ ID NO 63
<211> LENGTH: 261
<212> TYPE: DNA
<213> ORGANISM: Artificial sequence
<220> FEATURE:
<223> OTHER INFORMATION: PPOA lumen signal peptide coding sequence

<400> SEQUENCE: 63
```

```
atggcaagtt tgtgtaatag tagtagtaca tctctcaaaa ctccttttac ttcttccacc    60
acttgtttat cttccactcc taagccctct caacttttcc tacatggaaa acgtaacaaa   120
gcattcaaag tttcatgtgg gaaggttacc aatactaacg gtaaccaaga tgaaacgaat   180
tctgttgatc gaagaaatgt tcttcttggc ttaggtggtc tttatggtgt tgctaatgct   240
ataccattag ctgcatccgc t                                             261
```

<210> SEQ ID NO 64
<211> LENGTH: 87
<212> TYPE: PRT
<213> ORGANISM: Artificial sequence
<220> FEATURE:
<223> OTHER INFORMATION: PPOA lumen signal peptide sequence

<400> SEQUENCE: 64

```
Met Ala Ser Leu Cys Asn Ser Ser Thr Ser Leu Lys Thr Pro Phe
1               5                   10                  15

Thr Ser Ser Thr Thr Cys Leu Ser Ser Thr Pro Lys Pro Ser Gln Leu
            20                  25                  30

Phe Leu His Gly Lys Arg Asn Lys Ala Phe Lys Val Ser Cys Gly Lys
        35                  40                  45

Val Thr Asn Thr Asn Gly Asn Gln Asp Glu Thr Asn Ser Val Asp Arg
    50                  55                  60

Arg Asn Val Leu Leu Gly Leu Gly Gly Leu Tyr Gly Val Ala Asn Ala
65                  70                  75                  80

Ile Pro Leu Ala Ala Ser Ala
                85
```

<210> SEQ ID NO 65
<211> LENGTH: 111
<212> TYPE: DNA
<213> ORGANISM: Artificial sequence
<220> FEATURE:
<223> OTHER INFORMATION: Plastid signal peptide, predicted to direct
      protein to the stroma

<400> SEQUENCE: 65

```
gacccctcca ctcccaaaaa caacacacaa tattcaagga tgatagttgg ctatagaagc    60
acaatcatta ccctttctca tcctaagcta ggcaatggga aaacaatttc a            111
```

<210> SEQ ID NO 66
<211> LENGTH: 138
<212> TYPE: DNA
<213> ORGANISM: Artificial sequence
<220> FEATURE:
<223> OTHER INFORMATION: Plastid signal peptide, predicted to direct
      protein to the stroma

<400> SEQUENCE: 66

```
atgagttctt tggttcttca atgttggaaa ttatcatctc catctctgat tttacaacaa    60
aatacatcaa tatccatggg tgcattcaaa ggtattcata aacttcaaat cccaaattca   120
cctctgacag tgtctgct                                                 138
```

<210> SEQ ID NO 67
<211> LENGTH: 1834
<212> TYPE: DNA
<213> ORGANISM: Nicotiana tabacum

<400> SEQUENCE: 67

```
tctagactac catcgctagt aatcgtggca ataactaccc taactatagc atttattgct    60
```

```
accaaataaa atttggcagc taatcataat tttttgtcat gaatcaatag ttattgtagc       120
aatagttatc tcttagccac aataaattat ttaaaataaa atattatagc taaataaata       180
tttttgcttt aagttctaaa agcttgtggc aatagttaaa tgatatagtc acagatttat       240
tggtataatt gaattatgtt gctaatttct tagttttttg ccacgagtta aaaattacca       300
atagctatag taacttttta atcacaataa aatatttgaa agaaaatatt gtagctaaat       360
gaatattttt tccttcaagt tattaaaagt tgtggcaata taggttaaat tagccacatg       420
tttcttgctt taatagaatt ttgtagctaa tcattaactt ttaccacgag ttgaacttaa       480
tataacaaca ataacctttt aaccataata aagcgattta aatcaaatat tactaaataa       540
ataactttgc tttcaagttt ctataaaatc atggcaatag tcattacgat aaaatgatat       600
aaccacgaat atattgcaac gataaaattct gtaactaatc attagttttt gcgacgaggt       660
aaattttccg tcacagtagc aatcttctag gcacattaaa aatttgaaac aaaattttgt       720
agtcaaataa atatttatct tcttatttta agaaaataaa aatagttaga taatagttac       780
tactatttgt catgaaaata tcaatagata caaatttaaa gtgactataa atttacgagt       840
ttactatact ttagtcgtac agtttgcaat aatagtattt taaccacaat tagttatatg       900
tacaaaataa cataagtgaa taactttttt tcaatgagaa aataagagtt gctcaaacaa       960
tatcaagtta caaaaattta attttaactg taaaagttat attttccaa aataacataa      1020 actatagtaa ttatatatag tttgaagtat taataaaatt taaatatgca aaagttaatt      1080
ttaataaacc atttgtatgc ctaacttgta gcctctaaac tattttattt gctttatta      1140 tcaaactcat attttatttt attgcacctt gttagttttg gacgttaatt atatatattt      1200
ggtgtaaaat ttaaaatata ttaacatttg tggagaattt atgtatgcct ggttcttaac      1260 tattttttt tatataactg gttagagtaa tttcttatat ttcagtattt atttttaaat      1320
aagtcctcat aaaattgaaga ctttaaaagt ttttgtgtca ttcctctttt tatttaagaa      1380
attgaagaat tccgctaaat ttcatatttc cgctgttatt taactgttta tttcccttgt      1440
taatataatt ggtaagaagt tttaaaataa aggagttaat gattttctag gttcatggct      1500
tgcctagctt ctacgagtaa gcgccatcac gactcccgag gataaggaaa tccgggtcgt      1560
agcattcact cacaaaaatt actaaaaaca aagtttaccc ttctcccaaa agtaaatttc      1620
atatttggct ccacataatg tgttcaatga gtcaagtgaa gtacttttca tgacaaaaaa      1680
aagttgctga aaaatgcata tctcatattt tttttttaga gaaatcccat ttcttgccta      1740
aacgaaagcc tataaaagag catatattgc aacaacagtt tgcagaaact atcaagtcaa      1800
ataatccccc ctttaattcc ctcccaaacc cggg                                  1834
```

<210> SEQ ID NO 68
<211> LENGTH: 1969
<212> TYPE: DNA
<213> ORGANISM: Nicotiana tabacum

<400> SEQUENCE: 68

```
tctagataag ttgataaagc taatttctca ttttagctac catcgctagt aatcgtggca        60
ataactaccc taactatagc atttattgct accaaataaa atttggcagc taatcataat       120
tttttgtcat gaatcaatag ttattgtagc aatagttatc tcttagccac aataaattat       180
ttaaaataaa atattatagc taaataaata tttttgcttt aagttctaaa agcttgtggc       240
aatagttaaa tgatatagtc acagatttat tggtataatt gaattatgtt gctaatttct       300
tagttttttg ccacgagtta aaaattacca atagctatag taacttttta atcacaataa       360
```

```
aatatttgaa agaaaatatt gtagctaaat gaatattttt tccttcaagt tattaaaagt      420
tgtggcaata taggttaaat tagccacatg tttcttgctt taatagaatt ttgtagctaa      480
tcattaactt ttaccacgag ttgaacttaa tataacaaca ataaccttt  aaccataata      540 aagcgattta aatcaaatat tactaaataa ataactttgc tttcaagttt ctataaaatc      600
atggcaatag tcattacgat aaaatgatat aaccacgaat atattgcaac gataaattct      660
gtaactaatc attagttttt gcgacgaggt aaattttccg tcacagtagc aatcttctag      720
gcacattaaa aatttgaaac aaaattttgt agtcaaataa atatttatct tcttatttta      780
agaaaataaa aatagttaga taatagttac tactatttgt catgaaaata tcaatagata      840
caaatttaaa gtgactataa atttacgagt ttactatact ttagtcgtac agtttgcaat      900
aatagtattt taaccacaat tagttatatg tacaaaataa cataagtgaa taactttttt      960
tcaatgagaa aataagagtt gctcaaacaa tatcaagtta caaaaattta attttaactg     1020
taaaagttat atttttccaa aataacataa actatagtaa ttatatatag tttgaagtat     1080
taataaaatt taaatatgca aaagttaatt ttaataaacc atttgtatgc ctaacttgta     1140
gcctctaaac tattttattt gctttattta tcaaactcat attttatttt attgcacctt     1200 gttagtttg dacgttaatt atatatattt ggtgtaaaat ttaaaatata ttaacatttg      1260
tggagaattt atgtatgcct ggttcttaac tattttttt  tatataactg gttagagtaa     1320
tttcttatat ttcagtattt atttttaaat aagtcctcat aaattgaaga ctttaaaagt     1380
ttttgtgtca ttcctctttt tatttaagaa attgaagaat tccgctaaat ttcatatttc     1440
cgctgttatt taactgttta tttcccttgt taatataatt ggtaagaagt tttaaaataa     1500
aggagttaat gatttttctag gttcatggct tgcctagctt ctacgagtaa gcgccatcac    1560
gactcccgag gataaggaaa tccgggtcgt agcattcact cacaaaaatt actaaaaaca    1620
aagtttaccc ttctcccaaa agtaaatttc atatttggct ccacataatg tgttcaatga    1680
gtcaagtgaa gtacttttca tgacaaaaaa aagttgctga aaaatgcata tctcatattt    1740
tttttttaga gaaatcccat ttcttgccta aacgaaagcc tataaaagag catatattgc    1800
aacaacagtt tgcagaaact atcaagtcaa ataatccccc ctttaattcc ctcccaaaat    1860
gcagttcttc aacttctttt ccctttttcct ttttgtgtca tttctctttt tatttaagaa   1920
atggaagaat tccaatagcc aaaccaaaag attgcctcca ggtcccggg                1969
```

<210> SEQ ID NO 69
<211> LENGTH: 806
<212> TYPE: DNA
<213> ORGANISM: Lycopersicon esculentum

<400> SEQUENCE: 69

```
atggaagtaa ctttgttgta tagtacttca ctctctattt tgtttgtgct tctacttgtt      60
aaacttgttt catcaaaacg aagaaaacag aatctaccac caagcccact acttaaactt     120
ccaatattag gccatctcta tctccttaaa ccacmtctat atcgcactct gctaatctc      180 tcaactaaat atggccctgt tttctctctt caattaggta cccgtcttgt tgtagcaatt     240
tcctcaccat ctgctgccga agaatgtttc acaaaaaatg atatcgtttt tgctaatcgc     300
cctcggacaa tgacggcaaa attcataggc tataactcta ctacagtcat tggttctcct    360
tatggtgatc actggcgcta ccttcgccgc ctctgcgcac ttgaaatatt ctccactaat    420
cgtctcaaca attttcagtc cattagacaa gatgaaatca aacttttagt tcgaagagtg    480
tttcacaaat ctggagacaa ttttgtgact cctgttgagc ttaagtccaa gcttttttcag   540
```

```
atgtcgtata atattatcat gagaatggta gctggaaaaa gatattacgg tgaagagata      600
gataacgagg aggcaaatca ttttcgggtg cttgtagaag argttatttc ktttgggggt      660
gtatcaaatg ccghggattt catgcctgca atatttctgk tgttttttcag gagtacggag    720 aaaaaaatag caaagcttgg taataagatg gacaagstct tgcaaggttt ggktgatgaa     780
catcgccgcg ataaaagcag gaatac                                           806
```

<210> SEQ ID NO 70
<211> LENGTH: 912
<212> TYPE: DNA
<213> ORGANISM: Lycopersicon esculentum

<400> SEQUENCE: 70

```
atgagttctt tggttcttca atgttggaaa ttatcatctc catctctgat tttacaacaa       60
aatacatcaa tatccatggg tgcattcaaa ggtattcata aacttcaaat cccaaattca      120
cctctgacag tgtctgctcg tggactcaac aagatttcat gctcactcag cttacaaacc      180
gaaaaacttt gttatgagga taatgataat gatcttgatg aagaacttat gcctaaacac      240
attgctttga taatggatgg taataggaga tgggcaaagg ataagggttt agacgtatcc      300
gaaggtcaca acatctctt ccaaaatta aaagagattt gtgacatttc ttctaaattg       360
ggaatacaag ttatcactgc ttttgcattc tctactgaaa attggaaacg agccaagggg     420
gaggttgatt tcttgatgca aatgttcgaa gaactctatg atgagttttc gaggtctgga    480
gtaagagtgt ctattattgg ttgtaaaacc gacctcccaa tgacattaca aaaatgcata    540
gcattaacag aagagactac aaagggaaac aaaggacttc accttgtgat tgcactaaac   600
tatggtggat attatgacat attgcaagca acaaaaagca ttgttaataa agcaatgaat     660
ggtttattag atgtagaaga tatcaacaag aatttatttg atcaagaact tgaaagcaag   720
tgtccaaatc ctgatttact tataaggaca ggaggtgatc aaagagttag taacttttg    780 ttgtggcaat tggcttayac tgaatttttac ttcaccaama cattgtttcc tgattttgga   840
gaggaagatc ttaaagaggc aataatraac tttcaacaaa ggcatagacg ttttggtgga   900
cacacatatt ga                                                           912
```

<210> SEQ ID NO 71
<211> LENGTH: 1269
<212> TYPE: DNA
<213> ORGANISM: Lycopersicon esculentum

<400> SEQUENCE: 71

```
atgggtaata ttcatttgat tttcccactt ttatttatat cttgtttcat tttcccatcc       60
acaacaaatg ctactccaa cgcaatcata aaagcttggt gcacccaaac acctcatcca      120
caaccttgtg aatacttctt atcacaaaat cccaaaatta catctcctat cataaaaaaa     180
tcagattttc taaaagtgtc actagactta gtgttagacc gtgcgttacg tgcccaactg    240
aacacatatt cactaggtcc aaaatgtcgt aacgagcgcg aaaaaaacgc atgggctgat   300
tgcattgaac tctatgaaaa ctcaatcaac aaaatcaaaa gcacagttga tccaaacaca   360
aaatgctcag ctactgatgc tcaaacatgg ttaagtacat ccttaacaaa tcttgaaaca   420
tgtaaagcag gtttcgaaga attaggcgtt acgattatg ttatgccact aatatcaaat     480
aataatgtgt catctttaat aagtaacgct ttagctttaa atcatggtta ttatactgaa    540
cctactaaaa gtagtactac tactcaagtt gatggatttc caacttgggt atctcctggt    600
gatagaaaat tgttgcaatc gtcgccgtcg tcgtcgtcaa cggcttctca ggcgaatgta    660
```

```
gtggtggcta ctgatggttc aggggatttt aagacagtga agaagctgt agatgctgct      720 gccaagaata aggaagtgg gaggtttgtg atatatgtga aagctgggac ttataatgaa      780
aatgtggaga ttggagaaaa ggtgaaaaat gttatgttga ttggagatgg cattggaaag    840
acaattatta ctggaagcaa aagtgttgga ggtggatcca ccacctttag atcagccaca    900
gttggtgctt ctggtgacgg atttattgct caaggcataa caattagaaa cactgctgga    960
ccccaaaagc accaagcagt agccctacga tctggctctg atctttcagt attttatcaa   1020
tgtagcttcg aagggtatca agacactttg tacgttcatt ccaataggca attttacaaa    1080
gagtgtgata tttatggtac ggtcgatttt atatttggtm acgcagcagt tgtattacaa    1140
aattgtaata ttttcgctag agaccctccg aataaaatca acactgtgac agcccaaggc    1200
cgaaccgacc cgaatcaaaa cactggaatt ccatacata attgtagaat cactggagct    1260
ggttcttcg                                                            1269

<210> SEQ ID NO 72
<211> LENGTH: 930
<212> TYPE: DNA
<213> ORGANISM: Lycopersicon esculentum

<400> SEQUENCE: 72
atggcagacg gagaggatat tcagccccct gtctgtgaca atggaactgg aatggtcaag     60
gctgggttcg caggagatga tgctccacga gctgtatttc ctagtattgt tggccgcccc    120
cgccatactg gtgtgatggt gggtatgggt caaaaagacg cctatgtggg agatgaagct    180
caatcaaaga gaggtatttt aactcttaaa tacccaattg agcacggaat tgtcagcaat    240
tgggatgata tggagaagat atggcatcat actttctaca atgagcttcg tgttgcccct    300
gaggagcatc ctgtcctcct aactgaagcc cctcttaacc caaaggctaa tcgtgaaaag    360
atgacccaga ttatgtttga dcttttcaat accccagcta tgtatgttgc tattcaggct    420
gtactctcac tgtatgccag tggtcgtacc accggtattg tgttggactc tggtgatggt    480
gtcagccaca ctgtcccaat ttatgaaggg tatgcccttc cacatgccat tctccgtctt    540
gacttggcag acgtgacct cactgatagt ttgatgaaga tcctgaccga gcgtggttac    600
tcgttcacca cctcagctga gcgagaaatt gtcagggacg tgaaagaaaa gctcgcttac    660
atagctcttg actatgaaca ggaactcgag acttcaaaga ccagctcttc tgttgagaag    720
agctatgagc tcccagatgg gcaggtgatc accattggtg ctgagcgttt ccggtgtcct    780
gaggtccttt tccaaccttc aatgattgga atggaagctc aggaatcca cgagactaca    840 tacaactcta tcatgaaatg tgacgtggat attaggaaag tctttatgg aaacattgtg    900 ctcagtggtg gtactaccat gtttgtatgc                                      930

<210> SEQ ID NO 73
<211> LENGTH: 1017
<212> TYPE: DNA
<213> ORGANISM: Lycopersicon esculentum

<400> SEQUENCE: 73
atggcaaacg gaaagatcaa aatcggaatc aacggattcg gtagaattgg tcgtttggtg     60
gctagagttg ctctacagag agatgatgtt gaactagttg cagtgaatga tccatttatt    120
tccactgatt acatgacata tatgtttaag tatgattcag tacatggaca atggaagcat    180
catgagctaa aggtcaagga tgagaagaca cttctctttg gagagaaggc tgttacagtt    240
tttggaatca ggaaccctga agatatccca tggggtgaag ctggtgctga cttcgttgtt    300
```

```
gaatcaaccg gtgtcttcac tgacaaggac aaggctgctg ctcacttgaa gggtggtgcc    360
aagaaggttg tgatctctgc tcctagcaaa gatgctccca tgtttgttgt gggtgtcaac    420
gagaatgaat acaagccaga gctggacatt gtctccaatg ctagttgcac aacgaactgc    480
cttgcacctt tggctaaggt tatcaatgat aggtttggca ttgttgaggg tctcatgacc    540
actgtccacg ccatgactgc cacccagaaa actgttgatg gtccatccat gaaggactgg    600
agaggtggaa gagctgcttc attcaacatc atccctagca gcactggtgc agccaaggct    660
gttggaaaag tgctcccaca acttaacggc aaattgactg gaatggcctt cagagtacca    720
actgctgatg tctccgttgt cgatcttact gtaagactcg agaaagaagc ctcctatgaa    780
gacattaagg ctgcaatcaa ggaggaatca gagggtaaat gaagggtat cttgggatac    840 actgaagatg atgtggtttc cacagacttt gttggtgaca gcaggtcaag cattttgat    900 gccaaggctg gaattgcttt gagcaagaat tttgtgaaag ttgtgtcatg gtatgacaac    960 gaatgggtt acagttcccg tgtgattgat ttgatctgcc atatggctaa ggcttga      1017

<210> SEQ ID NO 74
<211> LENGTH: 657
<212> TYPE: DNA
<213> ORGANISM: Lycopersicon esculentum

<400> SEQUENCE: 74
atggtgtcac tgaaacttca gaagcggctc gccgccagtg ttctaaagtg tgggagggga     60
aaagtatggc ttgaccctaa cgaaggcaat gaaatctcca tggctaactc aaggcaaaac    120
atcagaaagt tggtgaagga tggtttcatc atcaggaaac caaccaaaat tcactcacga    180
tctcgtgcac gcaggatgaa ggaagccaaa gaaagggcc gtcactctgg atatggtaag    240
cgtaagggta ccagggaggc taggttgccc acaaaggtgc tgtggatgag gagactcaga    300
gtcctcaggc gtttgcttcg taagtacagg gagtccaaga agattgacaa gcacatgtac    360
catgatatgt acatgaaggt gaagggtaat gtcttcaaga caagcgtgt tctcatggag    420 aacattcaca aaaccaaggc tgagaaggct agagagaaga ccttgtctga ccaatttgag    480
gccaggaggg caaagaacaa ggcaagcagg gaaagaaagt tcgctaggag ggaggaacgt    540
ttggcccagg gaccaggaga aagccagta caacctgcag cgccagcccc ggcaccagca    600
gcaacagcac ccccagccaa gactgctcag ggaggatcta agaagtcaaa gaagtga      657

<210> SEQ ID NO 75
<211> LENGTH: 132
<212> TYPE: DNA
<213> ORGANISM: Artificial sequence
<220> FEATURE:
<223> OTHER INFORMATION: PPOD stromal signal peptide coding sequence

<400> SEQUENCE: 75
atggcaagtt tgtgtagtaa tagtagtact acttctctca aaactccttt cacttcttta     60
ggttccactc caaagccttg tcaactttc ctacatggaa aacgtaacaa agcattcaaa    120
gtttcatgtc cc                                                       132

<210> SEQ ID NO 76
<211> LENGTH: 44
<212> TYPE: PRT
<213> ORGANISM: Artificial sequence
<220> FEATURE:
<223> OTHER INFORMATION: PPOD stromal signal peptide coding sequence

<400> SEQUENCE: 76
```

```
Met Ala Ser Leu Cys Ser Asn Ser Ser Thr Thr Ser Leu Lys Thr Pro
1               5                   10                  15

Phe Thr Ser Leu Gly Ser Thr Pro Lys Pro Cys Gln Leu Phe Leu His
            20                  25                  30

Gly Lys Arg Asn Lys Ala Phe Lys Val Ser Cys Pro
        35                  40
```

<210> SEQ ID NO 77
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 77
ccacatgcca ttctccgtct                                          20

<210> SEQ ID NO 78
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 78
gcttttcttt cacgtccctg a                                        21

<210> SEQ ID NO 79
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 79
ttgttgtggg tgtcaacgag a                                        21

<210> SEQ ID NO 80
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 80
atggcgtgga cagtggtca                                           19

<210> SEQ ID NO 81
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 81
cactctggat atggtaagcg taagg                                    25

<210> SEQ ID NO 82
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 82
ttcttggact ccctgtactt acga                                     24

<210> SEQ ID NO 83
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 83
tctcttcaat taggtacccg tcttg                                            25

<210> SEQ ID NO 84
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 84
tgaattttgc cgtcattgtc c                                                21

<210> SEQ ID NO 85
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 85
gggtttagac gtatccgaag gtc                                              23

<210> SEQ ID NO 86
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 86
gctcgtttcc aattttcagt agaga                                            25

<210> SEQ ID NO 87
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 87
ttacgtgccc aactgaacac a                                                21

<210> SEQ ID NO 88
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 88
caatgcaatc agcccatgc                                                   19

NUCLEOTIDE SEQUENCES FOR REGULATING GENE EXPRESSION IN PLANT TRICHOMES AND CONSTRUCTS AND METHODS UTILIZING SAME

RELATED APPLICATIONS

This application is a continuation-in-part of U.S. patent application Ser. No. 10/561,220, filed on Apr. 4, 2006, which is a National Phase of PCT Patent Application PCT/IL2004/000549, filed on Jun. 20, 2004, which claims the benefit of U.S. Provisional Patent Application No. 60/479,467, filed on Jun. 19, 2003.

FIELD AND BACKGROUND OF THE INVENTION

The present invention relates to nucleotide sequences for regulating gene expression in plant trichomes and, more particularly, to methods of utilizing such nucleotide sequences for synthesizing polypeptides and molecules of interest in plant trichomes.

Polypeptides can be expressed in a wide variety of cellular hosts. For economic reasons, genetically engineered unicellular microorganisms are most widely used for commercial production of polypeptides. However, in some cases, expression of mammalian proteins in unicellular organisms results in incorrect folding and processing of the expressed polypeptides leading to loss of biological or physiological activity of the obtained polypeptide. For these reasons, attempts have been made, with varying degrees of success, to express mammalian polypeptides in plants.

Transgenic plants are fast becoming a preferred system for the expression of many recombinant proteins, especially those intended for therapeutic purposes. One advantage of using plants is the potential for protein production on an agricultural scale at an extremely competitive cost. Among other advantages is that most plant transformation techniques result in a stable integration of the foreign DNA into the plant genome, so genetic recombination by crossing of transgenic plants is a simple method for introducing new genes, accumulating multiple genes into plants and avoiding the contamination of pathogens such as viruses and prions, which may affect human and animals. Furthermore, the processing and assembly of recombinant proteins in plants may also complement that in mammalian cells, which may be an advantage over the more commonly used microbial expression systems.

Although plants provide a suitable alternative to unicellular expression systems, several disadvantages characterize current approaches for production of protein in plants. First, the concentration of the produced protein is typically low (around 1% of total proteins) making purification extremely difficult. Second, other compounds may interfere with protein purification or even damage the proteins during purification. Third, expressing foreign proteins in propagated plants can lead to environmental contamination and health risks associated with unwanted production of those proteins in cross pollinated plants.

In efforts of overcoming the above described limitations and while reducing the present invention to practice, the present inventors have discovered that plant trichomes enable compartmentalized production of foreign proteins as well as enzymatic production of novel chemicals, since many types of chemicals are naturally produced and even secreted from trichomes.

The above ground surfaces of many plants are covered with trichomes or hairs. The morphology of these structures can vary greatly with tissue type and species. Indeed, the botanical literature contains more than 300 descriptions (uniseriate, capitate-sessile, etc.) of various morphological types of such hairs (3, and references therein). Functionally, trichomes may be simple hairs that deter herbivores, guide the path of pollinators, or affect photosynthesis, leaf temperature, or water loss through increased light reflectance as in desert species. Alternatively, they may be more specialized tissues (glandular secreting trichomes) whose principal function(s) may be to produce pest- or pollinator-interactive compounds that are stored or volatilized at the plant surface. It has been suggested that in some desert species the principal role of glandular secreting trichomes is to produce such high levels of exudate that it forms a continuous layer on the plant surface. This layer may increase light reflectance and thereby reduce leaf temperature (30).

Trichomes develop projections from protodermal cells. Their structures arise from a series of anticlinal and periclinal divisions to form supporting auxiliary cells and glands. The appearance of glands atop supporting cells and the occurrence of exudate around gland cells has suggested that secretions are produced in gland cells and not by other epidermal or subepidermal cells.

In several species, such as tomato and potato, a unique type of trichomes accumulates certain protein (polyphenol oxidase) and compound (polyphenol) in the associated glands on the top of the trichome. When an insect lands on a leaf surface and contacts these trichomes, they discharge their inner compounds thereby contacting the insect and smearing it with a brown sticky compound, which is the product of enzymatic oxidation of the polyphenols (reviewed in 4).

The mass production, accumulation, and secretion of such proteins and chemicals involve a specific genetic mechanism. This genetic mechanism includes genes (5, 6) and promoters (7, 8, 9) acting in trichome cells and cells organelles suited for accumulation and secretion of mass products. This genetic mechanism allows, for example, trichome exudates to reach 16% of total dry weight of leaves of a certain tobacco species (10) and a single protein to reach 60% of total proteins or a concentration of 14 mg/mL in the trichome content of a *solanum* species (11, 12). The use of this genetic mechanism was suggested for tissue specific production and accumulation of natural and heterologous proteins as well as chemicals (6). New compounds produced can be beneficial for the plant itself by increasing resistance against pests such as insects, bacteria, and fungi (6), or for Molecular Farming or Bio-Farming of human or mammalian proteins for the use as therapeutics. In the latter, harvesting the proteins produced in the trichomes can be mechanized.

Directing protein expression into trichome cells may involve the use of polynucleotides originated form different origins. A candidate source for such regulatory elements is cotton as its fiber tissue is structurally modified trichomes. The promoter sequences of cotton fiber specific genes were shown to direct β-glucuronidase (GUS) expression to the trichome cells of tobacco plants (7, 9). Alteration of trichomes structure or chemistry by, for example, increasing cotton trichome length or by producing pigments in the fiber could be beneficial for the cotton industry.

Natural chemicals of trichomes are already used as flavor, aroma, medicinals, pesticides, and cosmetic ingredients (13, 14). Natural chemicals content was altered using antisense and co-suppression methods (6). However, enzymatic modifications of trichomes compounds via genetic engineering of genes, designed to produce other useful compounds in trichomes, was never shown before.

Several limitations had narrowed so far the use of plant trichomes for commercially production of heterologous proteins and novel chemicals.

First, protein yield is very limited in trichome cells and to date there is no existing method that enables commercially significant production of proteins in these cells. Although there are known promoter sequences that are capable of directing protein synthesis in trichomes (7, 8, 9), proteins expressed therefrom accumulated at average levels of accumulation of a single trichome protein and thus these promoters cannot be considered commercially useful for protein production, as is. Second, trichomes usually produce a mix of several metabolites, some of which (e.g., phenols and alkaloids), can inhibit protein accumulation or substantially hinder purification of desired compounds produced in trichomes (See material and methods in 12). Thus, reducing the levels of such harmful metabolites is required in order to improve harvesting and collection of the desired products. Third, the production of novel compounds in plants always involves risks of escape of genetic material (pollen and seeds) to the environment with potential damage to other organisms (plants, insects animals, human). Hence, when producing novel compounds one should consider the elimination of the possible spread of the new genetic material.

There is thus a widely recognized need for and it would be highly advantageous to have nucleotide sequences for regulating gene expression in plant trichomes methods of utilizing such nucleotide sequences for generating molecules of interest in plant trichomes.

SUMMARY OF THE INVENTION

According to one aspect of the present invention there is provided an isolated polynucleotide comprising a nucleic acid sequence at least 80% identical to SEQ ID NO: 23, 26 or 29, wherein the nucleic acid sequence is capable of regulating expression of at least one polynucleotide sequence operably linked thereto in trichomes.

According to another aspect of the present invention there is provided a nucleic acid construct comprising the isolated polynucleotide.

According to further features in preferred embodiments of the invention described below, the nucleic acid construct further comprising at least one heterologous polynucleotide operably linked to the isolated polynucleotide.

According to still further features in the described preferred embodiments the nucleic acid construct further comprises, a nucleic acid sequence encoding a peptide capable of directing transport of a polypeptide fused thereto into a subcellular compartment of a trichome.

According to still further features in the described preferred embodiments the nucleic acid sequence is selected from the group consisting of SEQ ID NOs: 59, 61, 63, 65 and 75.

According to yet another aspect of the present invention there is provided a transgenic cell comprising the nucleic acid construct.

According to still another aspect of the present invention there is provided a transgenic plant comprising the nucleic acid construct.

According to an additional aspect of the present invention there is provided an isolated polynucleotide comprising a nucleic acid sequence encoding a peptide capable of directing transport of a polypeptide fused thereto into a subcellular compartment of a trichome, wherein the peptide is encoded by the polynucleotide sequence set forth in SEQ ID NOs: 59, 61, 63, 65 and 75.

According to yet an additional aspect of the present invention there is provided a nucleic acid construct comprising the isolated polynucleotide.

According to still further features in the described preferred embodiments the nucleic acid construct further comprising an expressible polynucleotide sequence translationally fused to the nucleic acid sequence encoding the peptide.

According to still an additional aspect of the present invention there is provided a method of producing a polypeptide of interest in plant trichomes, the method comprising:
(a) expressing the polypeptide of interest in the plant trichomes; and
(b) down-regulating a level of at least one molecule endogenous to the plant trichomes, the at least one molecule being capable of interfering with expression, accumulation or stability of the polypeptide of interest.

According to still further features in the described preferred embodiments step (b) is effected by gene silencing.

According to a further aspect of the present invention there is provided a method of producing a molecule of interest in plant trichomes, the method comprising: (a) expressing a polypeptide capable of directly or indirectly increasing a level of the molecule of interest in the plant trichomes; and (b) down-regulating a level of at least one molecule endogenous to the plant trichomes, the at least one molecule being capable of interfering with accumulation or stability of the molecule of interest, thereby producing the molecule in the plant trichomes.

According to still further features in the described preferred embodiments the polypeptide is endogenously expressed in the plant trichomes.

According to still further features in the described preferred embodiments the expressing the polypeptide in the plant trichomes is effected by introducing into the plant trichomes a nucleic acid sequence encoding the polypeptide positioned under a transcriptional control of a promoter functional in the plant trichomes.

According to still further features in the described preferred embodiments the promoter is as set forth in SEQ ID NO: 23, 26, 29, 35, 38, 39, 42, 48, 50 or 51.

According to still further features in the described preferred embodiments the nucleic acid sequence encoding the polypeptide of interest further encodes a peptide capable of directing transport of the polypeptide fused thereto into a subcellular compartment of the plant trichomes.

According to still further features in the described preferred embodiments the at least one molecule is an enzyme or a metabolite.

According to still further features in the described preferred embodiments the metabolite is selected from the group consisting of polyphenols, ketones, terpenoids, phenylpropanoids and alkaloids.

According to still further features in the described preferred embodiments the enzyme is PPO.

According to still further features in the described preferred embodiments step (b) is effected by gene silencing.

According to yet a further aspect of the present invention there is provided a plant genetically modified to express a molecule of interest in trichomes, wherein the plant is further modified or selected capable of accumulating less than 50% of average volume of undesired compounds in trichome cells of the plant species.

According to still further features in the described preferred embodiments at least a portion of cells of the plant are genetically modified to include an expression construct including a polynucleotide sequence of a trichome specific promoter.

According to still further features in the described preferred embodiments the expression construct further includes an additional polynucleotide sequence encoding a peptide capable of directing transport of a polypeptide fused thereto into a subcellular compartment of the trichome, whereas the additional polynucleotide is translationally fused to the polynucleotide sequence.

According to still further features in the described preferred embodiments at least a portion of cells of the plant are genetically modified to include an expression construct including a first polynucleotide sequence encoding the polypeptide translationally fused to a second polynucleotide sequence encoding a peptide capable of directing transport of a polypeptide fused thereto into a trichome.

According to still further features in the described preferred embodiments the expression or accumulation is in a subcellular compartment of trichomes.

According to still further features in the described preferred embodiments the subcellular compartment is a leucoplast.

According to still further features in the described preferred embodiments the trichome specific promoter is set forth by SEQ ID NO: 23, 26 or 29.

According to still further features in the described preferred embodiments the trichome specific promoter is set forth by SEQ ID NO: 23, 26, 29, 35, 38, 39, 42 or 45.

According to still further features in the described preferred embodiments the additional polynucleotide sequence is set forth by SEQ ID NO: 59, 61, 63, 65 and 75.

According to still further features in the described preferred embodiments the molecule of interest is not a reporter polypeptide.

According to still further features in the described preferred embodiments the plant is modified or selected capable of generating a trichome density above 50,000 trichomes/gram (gr) leaf tissue.

According to still further features in the described preferred embodiments the plant is modified or selected capable of generating a trichome size of 50% above average size of the plant species.

According to still further features in the described preferred embodiments the plant is modified or selected capable of generating leaf surface size at least 25% above average size of the plant species.

According to still further features in the described preferred embodiments the plant is modified or selected capable of generating total leaf number at least 50% above average leaf number of the plant species.

According to still further features in the described preferred embodiments the plant is sterile.

According to still further features in the described preferred embodiments the plant is further genetically modified capable of secreting the exogenous polypeptide from trichome cells.

According to still a further aspect of the present invention there is provided a method of harvesting trichomes and/or exudates and/or content thereof, the method comprising: (a) incubating a trichome-containing plant tissue in a liquid such that trichome exudates and content is released into the liquid, wherein incubating is effected while avoiding friction of the trichome-containing plant tissue with a solid phase; and (b) collecting the liquid, to thereby harvest the trichome exudates and content.

According to still further features in the described preferred embodiments the liquid includes an antioxidant.

According to still further features in the described preferred embodiments the antioxidant is selected from the group consisting of citric acid, ascorbic acid and sodium bisulfite According to still further features in the described preferred embodiments the liquid is water.

According to still further features in the described preferred embodiments the trichome-containing plant tissue is selected from the group consisting of a shoot, a flower and a leaf.

According to still a further aspect of the present invention there is provided an apparatus for mechanical harvesting of trichome exudates and content, the apparatus comprising a mechanism designed and configured for mechanically agitating a trichome-containing plant tissue in a fluid and collecting the fluid to containing the trichome exudates or content.

The present invention successfully addresses the shortcomings of the presently known configurations by providing nucleotide sequence for regulating gene expression in plant trichomes and methods of utilizing such nucleotide sequences for generating molecules in plant trichomes Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color photograph. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1A:
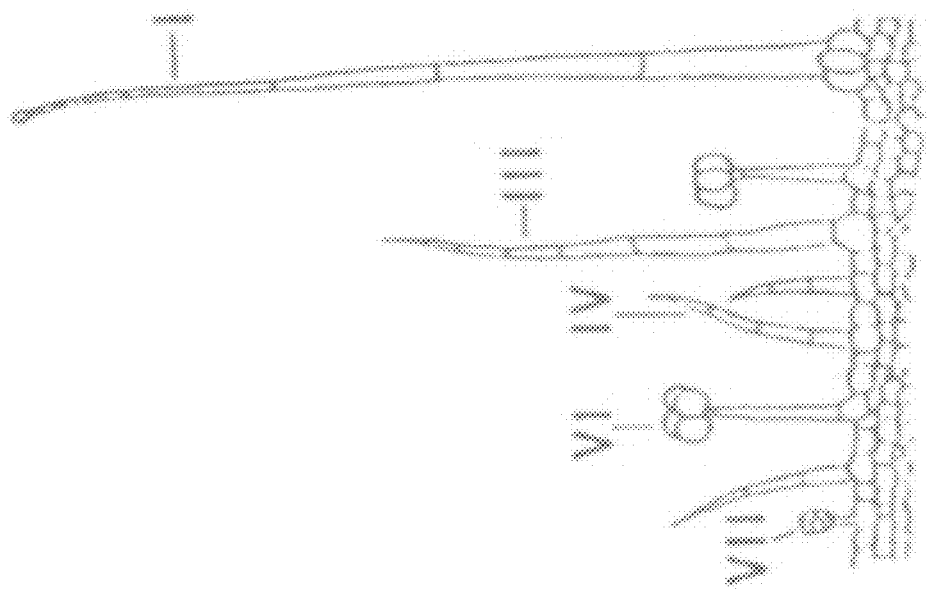

FIG. 1a is a prior art schematic illustration of various tomato trichomes. Type VI glandular trichomes naturally accumulate high levels of the PPO enzyme (Luckwill L C. 1943. The Aberden University Press, Aberden, Scotland).

Figure 1B:
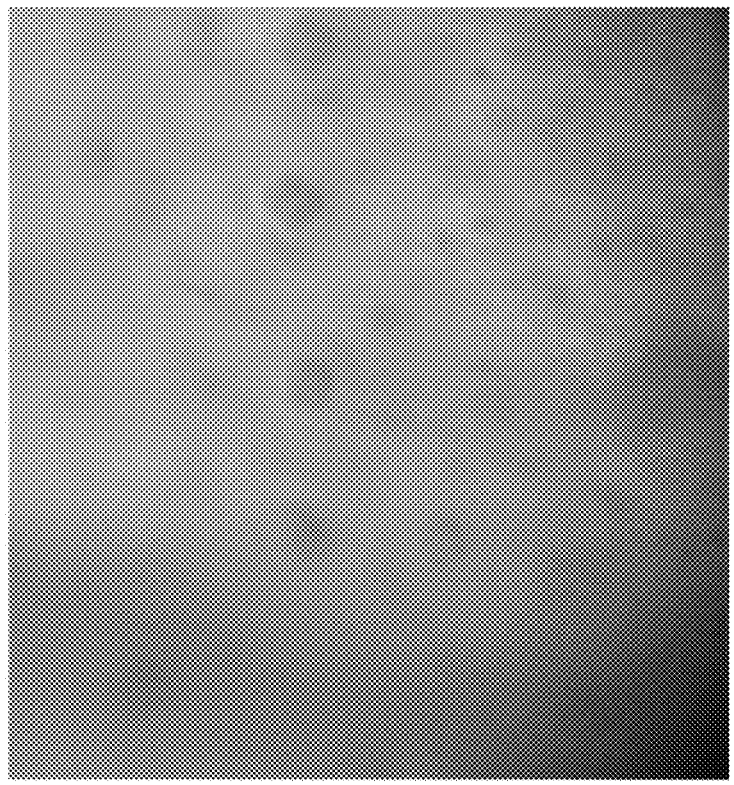
Figure 1C:
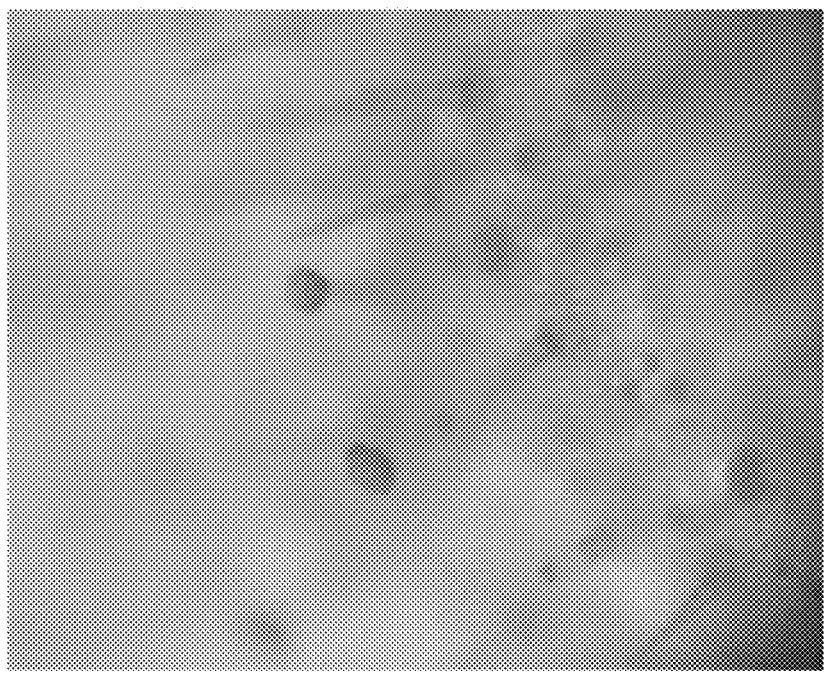
Figure 1D:
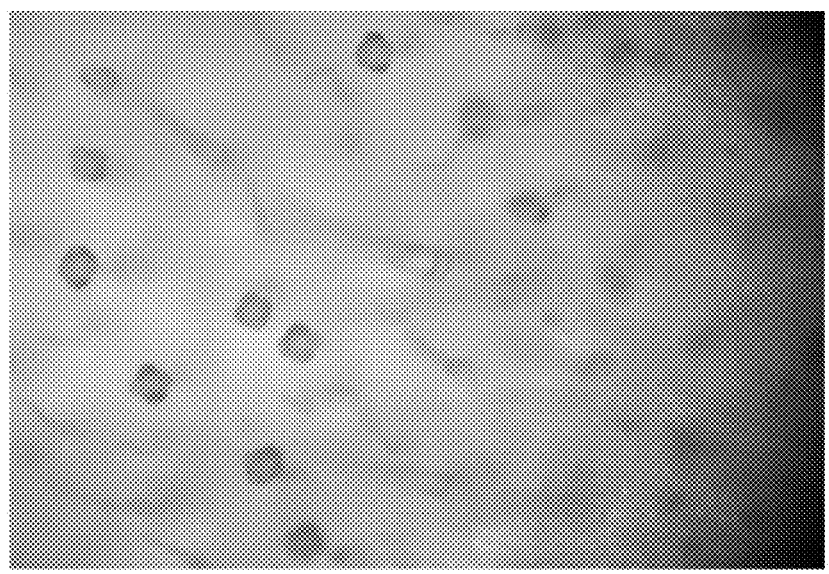
Figure 1E:
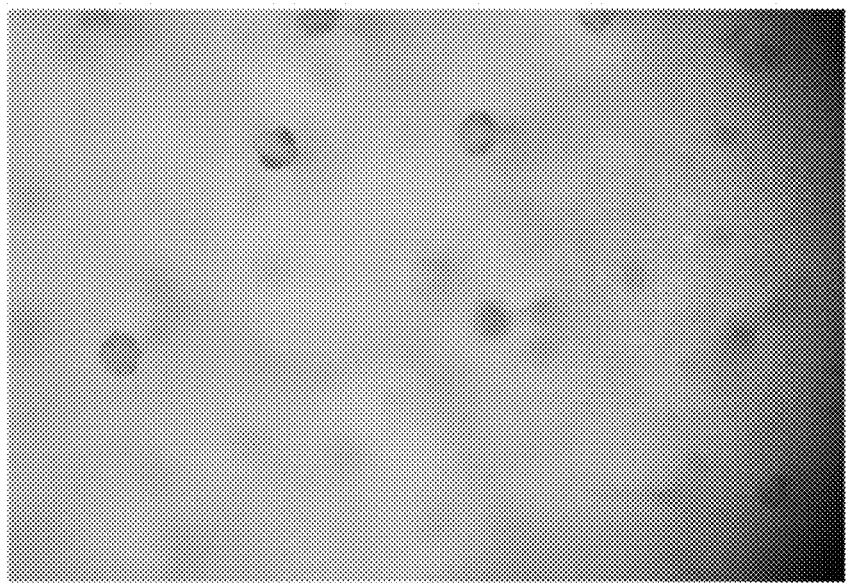

FIGS. 1b-h are photomicrographs depicting trichome specific expression of GUS under the regulation of the CaMV 35S, TR2, TR5, TR11, TR25 or TR27P promoters. The blue color corresponds to GUS expression. FIG. 1b—Trichomes of wild-type tomato plants. FIG. 1c—Trichomes of tomato plants overexpressing GUS under the constitutive CaMV 35S promoter. FIG. 1d—Trichomes of tomato plants overexpressing GUS under the TR2 promoter. FIG. 1e—Trichomes of tomato plants overexpressing GUS under the TR5 promoter.

Figure 1F:
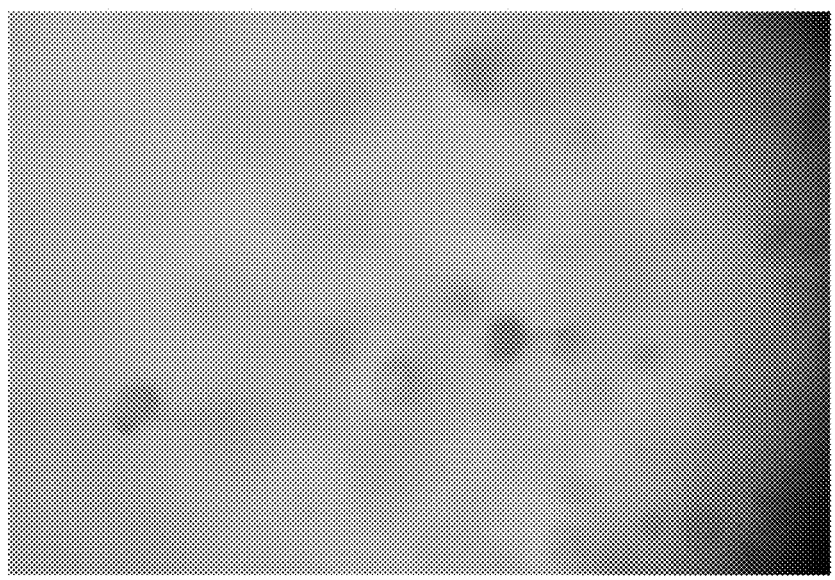
Figure 1G:

FIG. 1f—Trichomes of tomato plants overexpressing GUS under the TR11 promoter. FIG. 1g—Trichomes of tomato plants overexpressing GUS under the TR25 promoter. FIG. 1h—Trichomes of tomato plants overexpressing GUS under the TR27 promoter.

Figure 2:
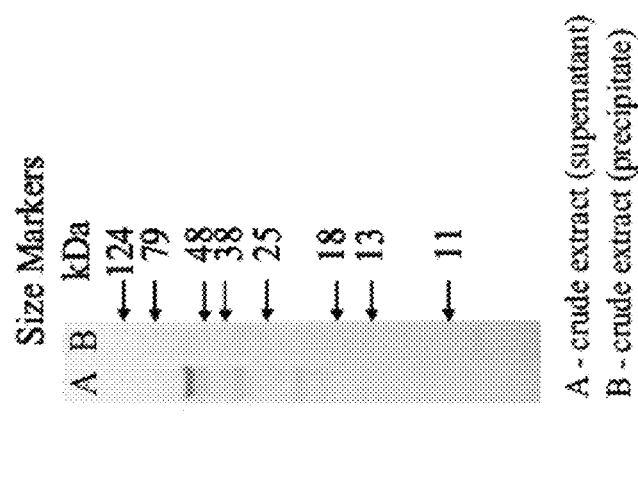

FIG. 2 is a photograph depicting total protein yield of chemically extracted trichome cells as determined by coomassie staining.

Figure 3:
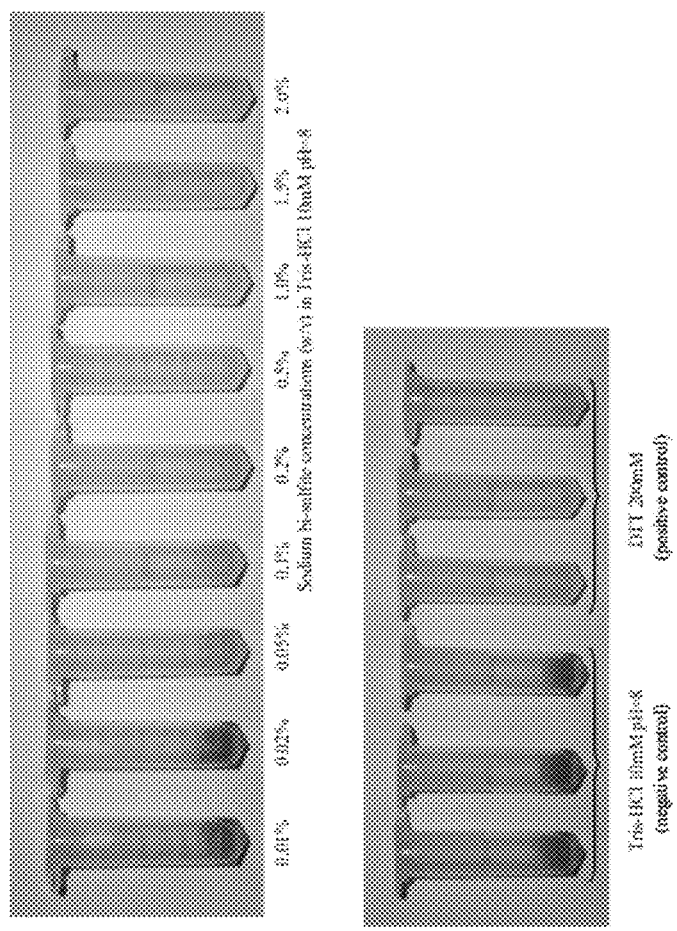

FIG. 3 is a photograph depicting decreased PPO activity in the presence of increasing concentrations of sodium bisulfite, as indicated by medium browning, which is indicative of PPO activity.

Figure 4A:
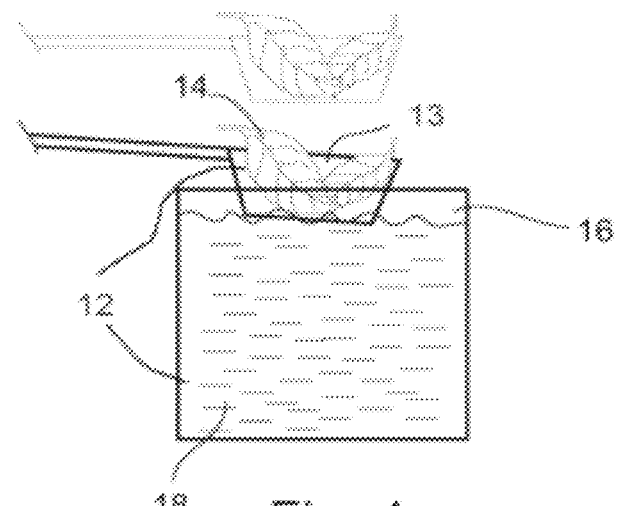

FIG. 4a schematically illustrates a trichome mechanical harvester constructed in accordance with some embodiments of the present invention.

Figure 4B:
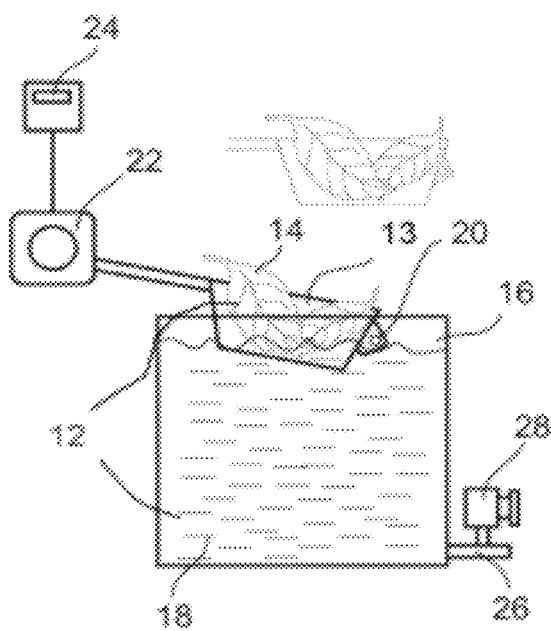

FIG. 4b schematically illustrates a trichome mechanical harvester constructed in accordance with some embodiments of the present invention.

Figure 4C:
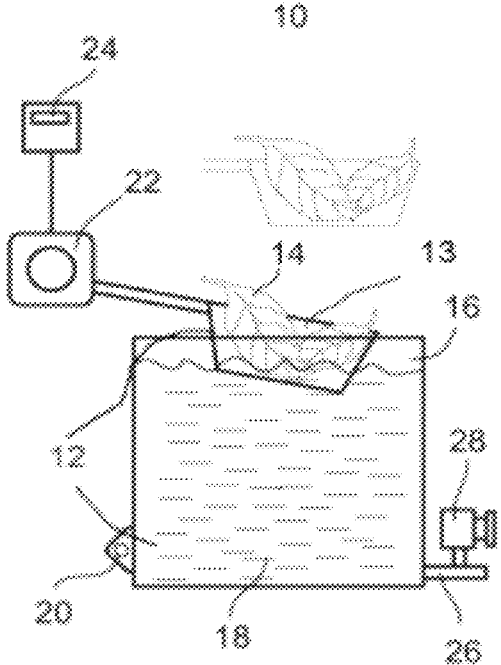

FIG. 4c schematically illustrates a trichome mechanical harvester constructed in accordance with some embodiments of the present invention.

Figure 5A:
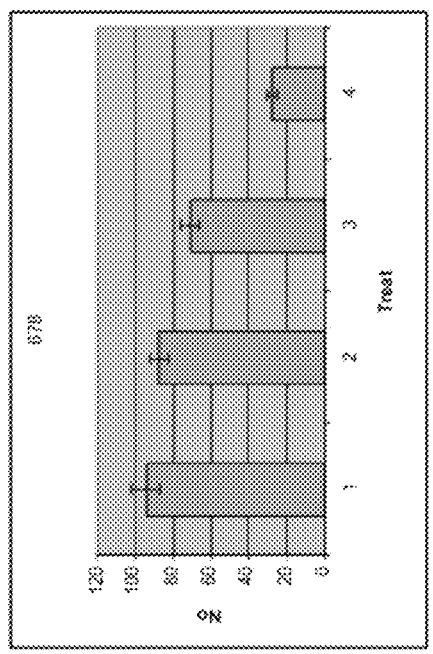
Figure 5B:
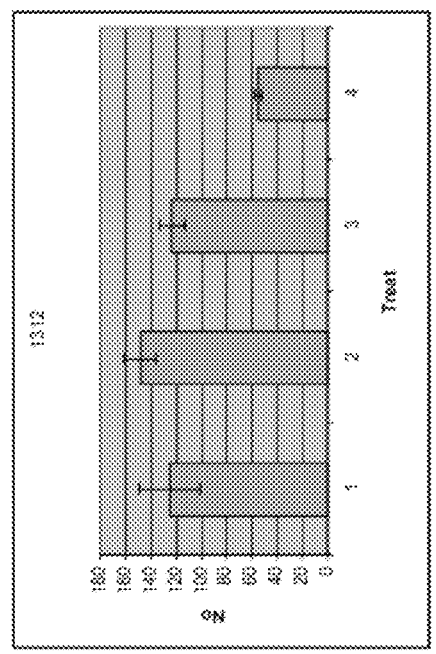
Figure 5C:
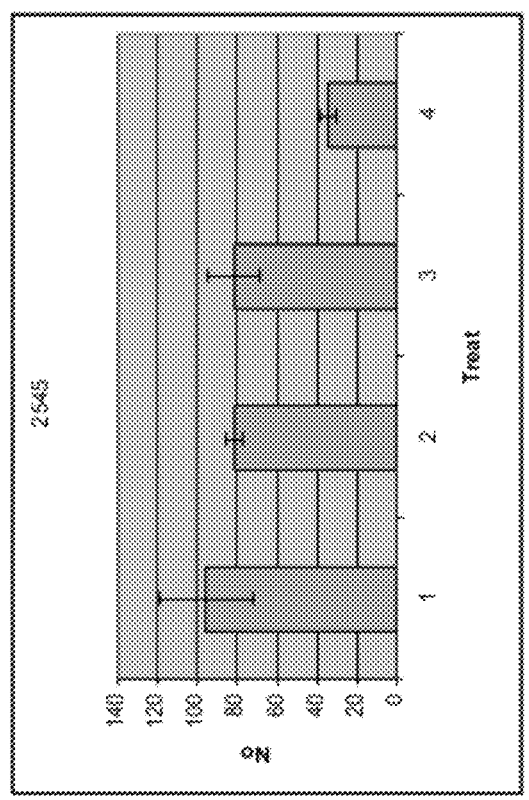

FIGS. 5a-c are graphs showing the effect of pruning on leaf number of 3 tomato cultivars. FIG. 5a cultivar 678; FIG. 5b cultivar 1312; FIG. 5c cultivar 2545. Treatment 1—Plant shoot number was not limited, plant height was limited to 1 m, flowers were cut-off before fruit set; Treatment 2—plant shoot number was not limited, plant height was limited to 2 m, flowers were cut-off before fruit set; Treatment 3—plant shoot number was not limited, leading apical meristem was cut (i.e. breaking apical dominance) when reached 0.5 m, flowers were cut-off before fruit set. Treatment 4—control plants were treated for tomato fruit set, such that each plant includes 2 shoots. Flowers and fruits were untouched.

Figure 6A:
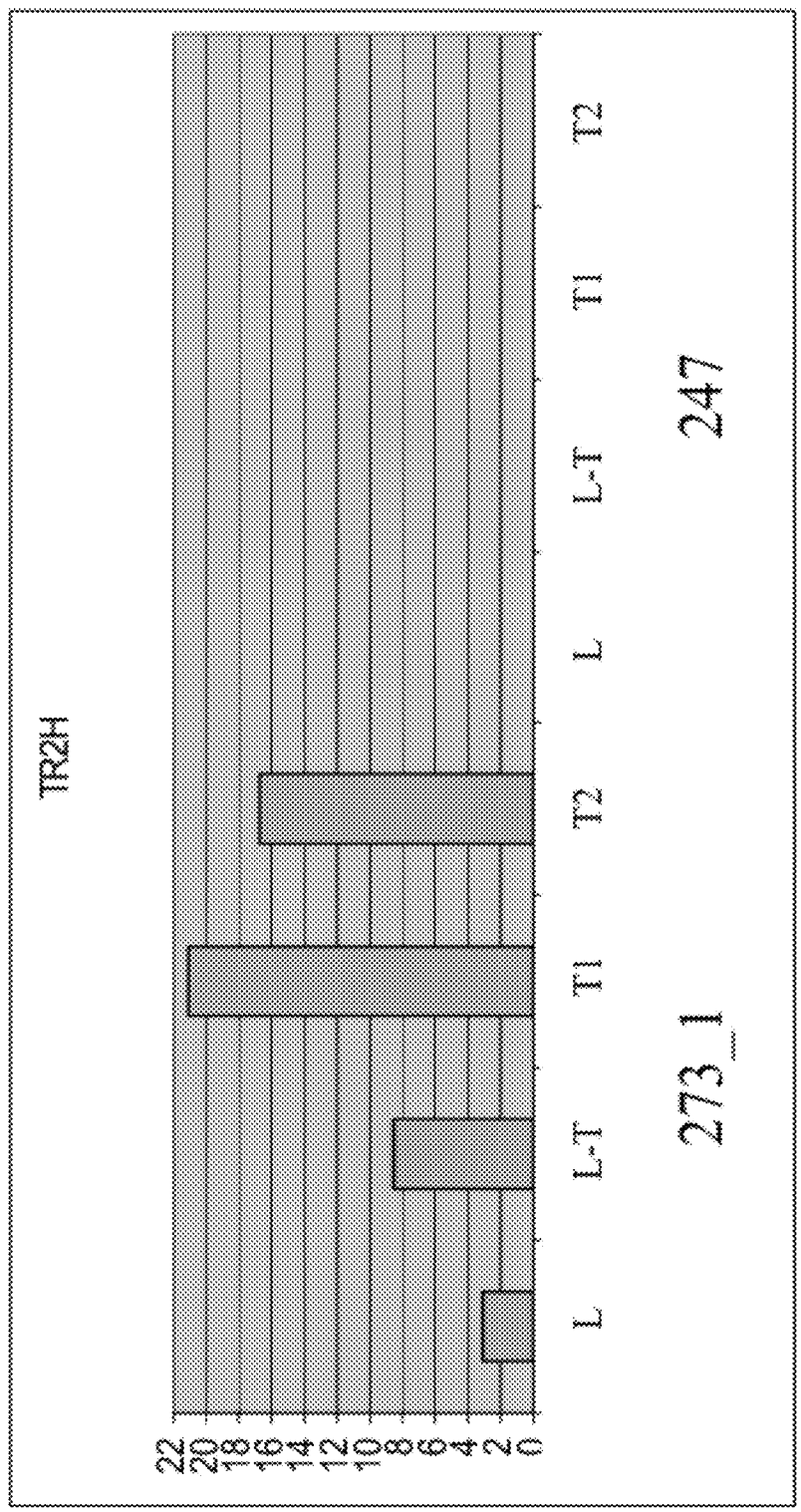
Figure 6C:
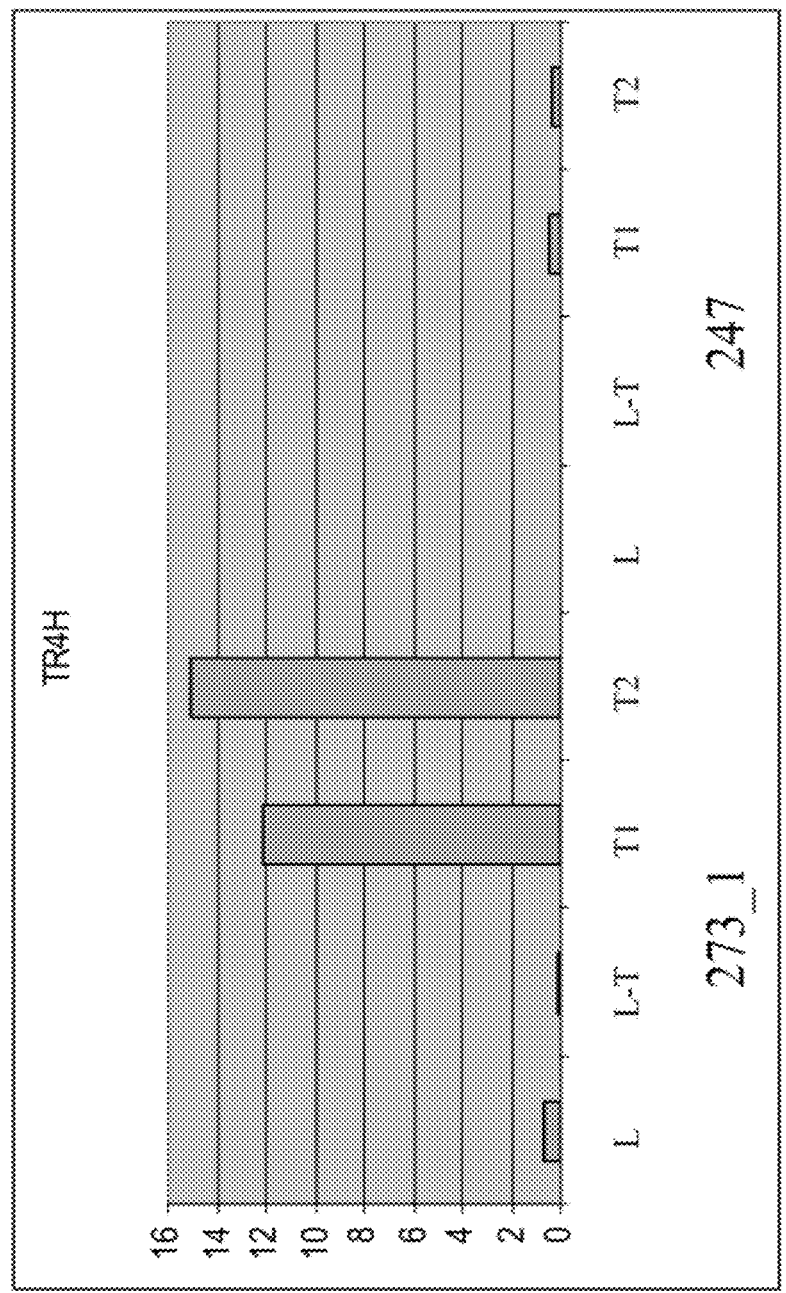
Figure 6D:
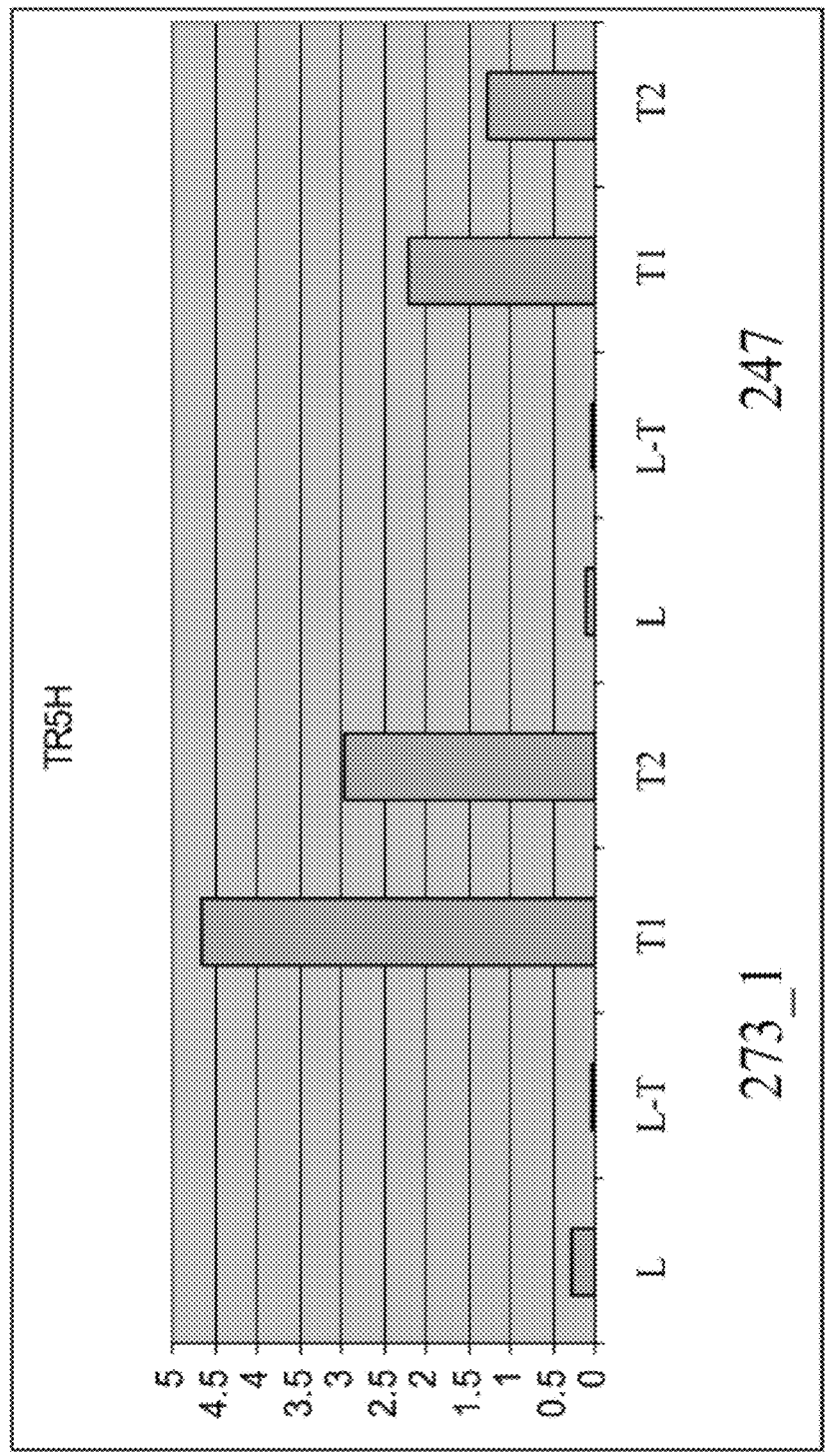

FIGS. 6a-d are graphs depicting expression levels of three trichome-expressed genes (TR2H, TR4H and TR5H) as determined by RT-PCR. Expression is shown as fold increase over house-keeping gene expression. 273_1 is *L. hirsutum* var *glabratum* cultivar; 247 is *L. esculentum* cultivar. FIG. 6a—a histogram depicting fold increase in the expression level of TR2H in 273_1 and 247 plants as compared to the expression level in house-keeping genes; FIG. 6b—a histogram depicting fold increase in the expression level of TR2H in 247 plants as compared to the expression level in house-keeping genes; FIG. 6c—a histogram depicting fold increase in the expression level of TR4H in 273_1 and 247 plants as compared to the expression level in house-keeping genes; FIG. 6d—a histogram depicting fold increase in the expression level of TR5H in 273_1 and 247 plants as compared to the expression level in house-keeping genes; Tissue key: L-Leaves; L-T-Leaves minus Trichomes; T1 and T2 are two independent RNA samples of Trichome cells.

DESCRIPTION OF THE PREFERRED EMBODIMENTS

The present invention is nucleotide sequence for regulating gene expression in plant trichomes which can be utilized for generating molecules in plant trichomes. Specifically the present invention is of plants which are modified for enhanced expression and accumulation of molecules in plant trichomes.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Trichomes are hairy-like epidermal multi-cell structures found on the outer surface of leaves, stems and flowers of about 20-30% of plant species. Their Main function is associated with plant protection against insects, microbes and herbivores due to their ability to massively accumulate and secrete pest-deterrent phytochemicals. Other functions include water absorption, seed dispersal and abrasion protection.

The high production capacity of trichomes prompted their utilization as "green-factories" for producing commercially useful compounds (e.g., U.S. Pat. No. 6,730,826). However, mass production of recombinant proteins in trichomes is limited by poor production efficiency and the presence of metabolites and enzymes, which may interfere with purification and activity of the desired compounds.

While reducing the present invention to practice the present inventors have devised a novel approach for increasing expression, accumulation and harvesting of molecules in plant trichomes, while reducing the chances of accidentally spreading the non-plant genetic material used to generate the molecules.

As is illustrated in the Examples section, the present inventors have uncovered that by reducing the concentration of undesired compounds in trichome exudates an enhanced level of expression, accumulation and/or purification of commercially valuable molecules within the trichomes can be achieved. Furthermore the present inventors uncovered through laborious experimentation and time consuming analysis a number of novel trichome active regulatory elements (see Example 1), which enable protein over-expression in trichomes (see Examples 2-4).

These findings allow, for the first time, improved molecular farming in trichome cells.

Thus, according to one aspect of the present invention there is provided a method of producing a molecule of interest in plant trichomes.

As used herein the term "trichome" refers to both a "simple" (also termed "non-glandular") trichome and a "glandular-secreting" (GST) trichome. Preferably, the term trichome refers to a GST trichome.

As used herein the term "molecule" refers to at least one small molecule chemical (e.g., nicotine, flavonoids). Such molecules can be naturally expressed or present in trichomes or can be direct or indirect expression products of heterologous polynucleotides. Examples of molecules which can be produced in trichome cells according to this aspect of the present invention include, but are not limited to, oils, dyes, flavors, biofuels, or industrial biopolymers, pharmaceuticals, nutraceuticals and cosmeceuticals.

As used herein the term "producing" refers to the process of expressing and/or accumulating the molecule in trichome cells. When appropriate, producing may also refer to subsequent steps of purifying the molecule from the trichome cells.

The method, according to this aspect of the present invention, is effected by upregulating expression of a polypeptide capable of directly or indirectly increasing a level of the molecule of interest; and down-regulating a level of at least one molecule endogenous to the plant trichome, which is capable of interfering with the production of the molecule in the plant trichomes, thereby producing the molecule in the plant trichomes.

Examples of polypeptides capable of directly or indirectly increasing the level of the molecule of interest include for example, trichome specific transcription factors which promote expression in trichome cells. Alternatively, the polypeptide can be an enzyme participating in a biochemical pathway, which produces the molecule in the trichome.

Expression of polypeptides in plant trichomes according to this aspect of the present invention, may be effected by placing a polynucleotide encoding the polypeptide of interest under the regulation of a cis-acting regulatory element capable of directing expression from the polynucleotide in trichome cells.

As used herein, the phrase "cis acting regulatory element" refers to a polynucleotide sequence, preferably a promoter, which binds a trans acting regulator and regulates the transcription of a coding sequence located downstream thereto in trichome cells.

It will be appreciated that a regulatory sequence is "operably linked" to a coding polynucleotide sequence if it is capable of exerting a regulatory effect on the coding sequence linked thereto. Preferably, the regulatory sequence is positioned 1-500 bp upstream of the ATG codon of the coding nucleic acid sequence, although it will be appreciated that regulatory sequences can also exert their effect when positioned elsewhere with respect to the coding nucleic acid sequence (e.g., within an intron).

A number of trichome active promoters are known in the art which can be used in accordance with the present invention. Examples include, but are not limited to, the CYP71D16 trichome-specific promoter [Wang E. J Exp Bot. (2002) 53(376):1891-7, see U.S. Pat. No. 6,730,826] and the cotton LTP3 and LTP6 promoters (7, 9).

Methods of identifying trichome active or specific promoters are well described in Examples 1-3 of the Examples section which follows.

As mentioned hereinabove, the present inventors have identified a number of cis-acting regulatory elements, which are capable of regulating transcription of coding nucleic acid sequences operably linked thereto in trichome cells.

Thus the present invention provides an isolated polynucleotide having a nucleic acid sequence at least 80% identical to SEQ ID NO: 23, 26 or 29, wherein the nucleic acid sequence is capable of regulating expression of at least one polynucleotide sequence operably linked thereto in trichomes.

According to other embodiments of this aspect of the present invention the nucleic acid sequence of the present invention is at least 80% identical to SEQ ID NO: 35, 38, 39, 42, 45, 48, 51 or 54.

Preferably, the polynucleotides (promoters) of the present invention are modified to create variations in the molecule sequences such as to enhance their promoting activities, using methods known in the art, such as PCR-based DNA modification, or standard DNA mutagenesis techniques, or by chemically synthesizing the modified polynucleotides.

Accordingly, the sequences set forth in SEQ ID NOs: 23, 26, 29, 35, 38, 39, 42, 45, 48, 51 and 54 may be truncated or deleted and still retain the capacity of directing the transcription of an operably linked DNA sequence in trichomes. The minimal length of a promoter region can be determined by systematically removing sequences from the 5' and 3'-ends of the isolated polynucleotide by standard techniques known in the art, including but not limited to removal of restriction enzyme fragments or digestion with nucleases.

In another approach, novel hybrid promoters can be designed or engineered by a number of methods. Many promoters contain upstream sequences which activate, enhance or define the strength and/or specificity of the promoter, such as described, for example, by Atchison [Ann. Rev. Cell Biol. 4:127 (1988)]. T-DNA genes, for example contain "TATA" boxes defining the site of transcription initiation and other upstream elements located upstream of the transcription initiation site modulate transcription levels [Gelvin In: Transgenic Plants (Kung, S.-D. and Us, R., eds, San Diego: Academic Press, pp. 49-87, (1988)]. Another chimeric promoter combined a trimer of the octopine synthase (ocs) activator to the mannopine synthase (mas) activator plus promoter and reported an increase in expression of a reporter gene [Min Ni et al., The Plant Journal 7:661 (1995)]. The upstream regulatory sequences of the present invention can be used for the construction of such chimeric or hybrid promoters. Methods for construction of variant promoters include, but are not limited to, combining control elements of different promoters or duplicating portions or regions of a promoter (see for example, U.S. Pat. Nos. 5,110,732 and 5,097,025). Those of skill in the art are familiar with the specific conditions and procedures for the construction, manipulation and isolation of macromolecules (e.g., DNA molecules, plasmids, etc.), generation of recombinant organisms and the screening and isolation of genes, [see for example Sambrook et al., Molecular Cloning: A Laboratory Manual, Cold Spring Harbor Press, (1989); Mailga et al., Methods in Plant Molecular Biology, Cold Spring Harbor Press, (1995); Birren et al., Genome Analysis: volume 1, Analyzing DNA, (1997); volume 2, Detecting Genes, (1998); volume 3, Cloning Systems, (1999); and volume 4, Mapping Genomes, (1999), Cold Spring Harbor, N.Y].

The above-described nucleic acid sequences (promoters) can be used to drive expression of a heterologous polynucleotide of interest in trichome cells. Preferably, the heterologous polynucleotide can encode any naturally occurring or man-made recombinant protein, such as pharmaceutical proteins [e.g., growth factors and antibodies Schillberg Naturwissenschaften. (2003) April; 90(4):145-55] and food additives. It will be appreciated that molecular farming is a well-proven way of producing a range of recombinant proteins, as described in details in Ma Nat Rev Genet. 2003 October; 4(10):794-805; Twyman Trends Biotechnol. 2003 December; 21(12):570-8.

To facilitate accumulation of the polypeptide of interest in trichome cells, it may be beneficial to translationally link the heterologous polynucleotide encoding the polypeptide to a signal peptide-encoding sequence which is capable of directing transport of the polypeptide into sub-cellular organelle of a the trichome. Examples of subcellular organelles of trichome cells include, but are not limited to, leucoplasts, chloroplasts, chromoplasts, mitochondria, nuclei, peroxisomes, endoplasmic reticulum and vacuoles. Preferably the signal peptide of this aspect of the present invention is a leucoplast localization signal. It is appreciated that since the protein is not accumulated in the cytoplasm, but rather in the subcellular organelle of the trichomes, it is expected to be stored in relatively high concentrations without being exposed to the degrading compounds present in the trichome vacuole. Examples of signal peptides which may be used in accordance with the present invention include, but are not limited to, the stroma or lumen directing signal peptides of PPOA and PPOD (SEQ ID NO: 60, 62, 64, 66 and 76, see Example 3). Polynucleotides encoding these signal peptides are set forth in SEQ ID NOs: 59, 61, 63, 65 and 75.

The polynucleotides (i.e., trichome active promoter sequence, signal peptide encoding polynucleotide) of the present invention, or fragments, variants or derivatives thereof, can be incorporated into nucleic acid constructs, preferably expression constructs (i.e., expression vectors), which can be introduced and replicate in a plant cell, such as a trichome. Such nucleic acid constructs may include the heterologous polynucleotide of interest such as described hereinabove, operably liked to any of the promoter sequences of the present invention.

The nucleic acid construct can be, for example, a plasmid, a bacmid, a phagemid, a cosmid, a phage, a virus or an artificial chromosome. Preferably, the nucleic acid construct of the present invention is a plasmid vector, more preferably a binary vector.

The phrase "binary vector" refers to an expression vector which carries a modified T-region from Ti plasmid, allowing multiplication both in E. coli and in Agrobacterium cells, and usually comprising selection gene(s). Such a binary vector suitable for the present invention is described in Example 1 of the Examples section which follows.

The nucleic acid construct of the present invention can be utilized to transform a host cell. Preferably a plant cell. Preferably, the nucleic acid construct of the present invention is used to transform at least a portion of cells of a plant.

Methods of introducing nucleic acid constructs into a cell or a plant are well known in the art. Accordingly, suitable methods for introducing nucleic acid sequences into plants include, but are not limited to, bacterial infection, direct delivery of DNA (e.g., via PEG-mediated transformation, desiccation/inhibition-mediated DNA uptake, electroporation, agitation with silicon carbide fibers, and acceleration of DNA coated particles, such as described by Potrykus Ann. Rev. Plant Physiol. Plant Mol. Biol. 42:205-225 (1991).

Methods for specifically transforming dicots primarily use *Agrobacterium tumefaciens*. For example, transgenic plants reported include but are not limited to cotton (U.S. Pat. Nos. 5,004,863, 5,159,135, 5,518,908; and WO 97/43430), soybean [U.S. Pat. Nos. 5,569,834, 5,416,011; McCabe et al., Bio/Technology, 6:923 (1988); and Christou et al., Plant Physiol., 87:671, (1988)]; *Brassica* (U.S. Pat. No. 5,463, 174), and peanut [Cheng et al., Plant Cell Rep., 15: 653, (1996)]. Similar methods have been reported in the transformation of monocots. Transformation and plant regeneration using these methods have been described for a number of crops including but not limited to asparagus [*Asparagus officinalis*; Bytebier et al., Proc. Natl. Acad. Sci. U.S.A., 84: 5345, (1987); barley (*Hordeum vulgarae*; Wan and Lemaux, Plant Physiol., 104: 37, (1994)]; maize [*Zea mays*; Rhodes, C. A., et al., Science, 240: 204, (1988); Gordon-Kamm, et al., Plant Cell, 2: 603, (1990); Fromm, et al., Bio/Technology, 8: 833, (1990); Koziel, et al., Bio/Technology, 11: 194, (1993)]; oats [*Avena sativa*; Somers, et al., Bio/Technology, 10: 1589, (1992)]; orchardgrass [*Dactylis glomerata*; Horn, et al., Plant Cell Rep., 7: 469, (1988); rice [*Oryza sativa*, including indica and japonica varieties, Toriyama, et al., Bio/Technology, 6: 10, (1988); Zhang, et al., Plant Cell Rep., 7: 379, (1988); Luo and Wu, Plant Mol. Biol. Rep., 6: 165, (1988); Zhang and Wu, Theor. Appl. Genet., 76: 835, (1988); Christou, et al., Bio/ Technology, 9: 957, (1991); sorghum [*Sorghum bicolor*, Casas, A. M., et al., Proc. Natl. Acad. Sci. U.S.A., 90: 11212, (1993)]; sugar cane [*Saccharum* spp.; Bower and Birch, Plant J., 2: 409, (1992)]; tall fescue [*Festuca arundinacea*; Wang, Z. Y. et al., Bio/Technology, 10: 691, (1992)]; turfgrass [*Agrostis palustris*; Zhong et al., Plant Cell Rep., 13: 1, (1993)]; wheat [*Triticum aestivum*; Vasil et al., Bio/Technology, 10: 667, (1992); Weeks T., et al., Plant Physiol., 102: 1077, (1993); Becker, et al., Plant, J. 5: 299, (1994)], and alfalfa [Masoud, S. A., et al., Transgen. Res., 5: 313, (1996)]. It is apparent to those of skill in the art that a number of transformation methodologies can be used and modified for production of stable transgenic plants from any number of target crops of interest.

The transformed plants can be analyzed for the expression features conferred by the polynucleotides of the present invention, using methods known in the art for the analysis of transformed plants (see Example 4 of the Examples section which follows). A variety of methods are used to assess gene expression and determine if the introduced gene(s) is integrated, functioning properly, and inherited as expected. Preferably, the promoters are evaluated by determining the expression levels and the expression features of genes to which the promoters are operatively linked. A preliminary assessment of promoter function can be determined by a transient assay method using reporter genes, but a more definitive promoter assessment can be determined from the analysis of stable plants. Methods for plant analysis include but are not limited to Southern blots or northern blots, PCR-based approaches, biochemical analyses, phenotypic screening methods, field evaluations, and immunodiagnostic assays. These methods may also be used to assess gene silencing, which is described hereinbelow.

As mentioned hereinabove, to enhance expression and/or accumulation of the molecule of interest in trichome cells and/or to facilitate purification of the molecule from trichome cells, down-regulation of at least one molecule endogenous to the plant trichomes and interfering with these processes is effected.

Trichomes are known to include a number of compounds (e.g., metabolites), which interfere with the production of molecules in these specialized cells. These metabolites include, for example polyphenols, ketones, terpenoids (e.g., monoterpenes, sesquiterpenes, diterpenes and triterpenes), mixed terpenes, phenylpropanoids and alkaloids. Other trichome components which may be preferably reduced to improve, expression, accumulation and purification of the molecules of this aspect of the present invention include proteases, and PPO (see Example 5 of the Examples section). For example downregulation PPO in trichome plastids would allow the recruitment of the protein translation machinery to a novel peptide and also to increase storage space in trichome plastids. Another example is reducing enzymatic activity of the polyphenols biosynthetic pathway to thereby decrease/ eliminate the production of polyphenols which make it difficult to harvest and purify proteins from trichomes (see above). Such enzymes include, but are not limited to, Phenylalanine ammonia-lyase (PAL, Acc. No. M90692, M83314), Cinnamate-4-hydroxylase (CA4H, GenBank Accession No. Z70216, A1490789), 4-Coumarate:coenzyme A ligase (4CL, GenBank Accession Nos. AWO34240, AF211800), chalcone and stilbene synthase (CHS, Acc. No. GenBank Accession No. X55195), Chalcone isomerase (CHI, Acc. No. GenBank Accession No. AY348871), F3H, flavanone 3-hydroxylase-naringenin 3-dioxygenase (F3OH), flavanone 3-hydroxylase-naringenin 3-dioxygenase (FDR), dihydroflavonol-4-reductase (DFR, GenBank Accession No. Z18277).

Down-regulation of such trichome components may be effected by down-regulating genes which are involved in the production or accumulation of these components. For example, gene products which are involved in exudate synthesis may be revealed by genome and EST mining and directed gene knock-out. Gene mining includes the identification in public databases (e.g., GenBank World Wide Web (dot) ncbi (dot) nlm (dot) nih (dot) gov/Genbank/index/html) of ortholohgous sequences deriving from the plant of interest which share homology with known genes in the pathway using sequence alignment software such as BLAST (World Wide Web (dot) ncbi (dot) nlm (dot) nih (dot) gov/BLAST). Alternatively, trichome EST libraries may be useful for identifying genes which are involved in metabolite synthesis [see for example Lange (2000) Proc. Natl. Acad. Sci. 97:2934-2939; Gang (2001) Plant Physiology 125:539-555].

Once genes associated directly or indirectly with metabolite synthesis are identified, they are down-regulated either at the nucleic acid level and/or at the protein level (e.g., antibodies).

An agent capable of downregulating gene expression is a small interfering RNA (siRNA) molecule. RNA interference is a two step process. the first step, which is termed as the initiation step, input dsRNA is digested into 21-23 nucleotide (nt) small interfering RNAs (siRNA), probably by the action of Dicer, a member of the RNase III family of dsRNA-specific ribonucleases, which processes (cleaves) dsRNA (introduced directly or via a transgene or a virus) in an ATP-dependent manner. Successive cleavage events degrade the RNA to 19-21 bp duplexes (siRNA), each with 2-nucleotide 3' overhangs [Hutvagner and Zamore Curr. Opin. Genetics and Development 12:225-232 (2002); and Bernstein Nature 409: 363-366 (2001)].

In the effector step, the siRNA duplexes bind to a nuclease complex to from the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA [Hutvagner and Zamore Curr. Opin. Genetics and Development 12:225-232 (2002); Hammond et al. (2001) Nat. Rev. Gen. 2:110-119 (2001); and Sharp Genes. Dev. 15:485-90 (2001)]. Although the mechanism of cleavage is still to be elucidated, research indicates that each RISC contains a single siRNA and an RNase [Hutvagner and Zamore Curr. Opin. Genetics and Development 12:225-232 (2002)].

Because of the remarkable potency of RNAi, an amplification step within the RNAi pathway has been suggested. Amplification could occur by copying of the input dsRNAs which would generate more siRNAs, or by replication of the siRNAs formed. Alternatively or additionally, amplification could be effected by multiple turnover events of the RISC [Hammond et al. Nat. Rev. Gen. 2:110-119 (2001), Sharp Genes. Dev. 15:485-90 (2001); Hutvagner and Zamore Curr. Opin. Genetics and Development 12:225-232 (2002)]. For more information on RNAi see the following reviews Tuschl ChemBiochem. 2:239-245 (2001); Cullen Nat. Immunol. 3:597-599 (2002); and Brantl Biochem. Biophys. Act. 1575: 15-25 (2002).

Synthesis of RNAi molecules suitable for use with the present invention can be effected as follows. First, the mRNA target sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (World Wide Web (dot) ambion (dot) com/techlib/tn/91/912 (dot) html).

Second, potential target sites are compared to an appropriate genomic database (e.g., human, mouse, rat etc.) using any sequence alignment software, such as the BLAST software available from the NCBI server (World Wide Web (dot) ncbi (dot) nlm (dot) nih (dot) gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

Antisense and siRNA technology has been used in selective downregulation of two tobacco trichome genes encoding different enzymes [Wang (2002); J. of Exp. Bot. 53:1891-1897; Wang (2003) Planta 216:686-691]. siRNA oligonucleotides for downregulating PPO for example, may be generated by inserting the cDNA sequence of PPO (GenBank Accession No: Z12833 for PPOA, GenBank Accession No. Z12836 for PPOD) to an siRNA selection software such as provided by World Wide Web (dot) ambion (dot) com.

Another agent capable of downregulating gene expression is a DNAzyme molecule capable of specifically cleaving an mRNA transcript or DNA sequence of the target. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al.

Downregulation of gene expression can also be effected by using an antisense polynucleotide capable of specifically hybridizing with an mRNA transcript encoding the target polypeptide of interest.

Design of antisense molecules which can be used to efficiently and specifically downregulate gene expression must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

Another agent capable of downregulating gene expression is a ribozyme molecule capable of specifically cleaving an mRNA transcript encoding the target polypeptide. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications.

An additional method of regulating the expression of a gene in cells is via triplex forming oligonucleotides (TFOs). Recent studies have shown that TFOs can be designed which can recognize and bind to polypurine/polypirimidine regions in double-stranded helical DNA in a sequence-specific manner. These recognition rules are outlined by Maher III, L. J., et al., Science, 1989; 245:725-730; Moser, H. E., et al., Science, 1987; 238:645-630; Beal, P. A., et al, Science, 1992; 251: 1360-1363; Cooney, M., et al., Science, 1988; 241:456-459; and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94).

In general, the triplex-forming oligonucleotide has the sequence correspondence:

```
oligo      3'--A      G    G    T duplex     5'--A      G    C    T duplex     3'--T      C    G    A
```

However, it has been shown that the A-AT and G-GC triplets have the greatest triple helical stability (Reither and Jeltsch, BMC Biochem, 2002, Sep. 12, Epub). The same authors have demonstrated that TFOs designed according to the A-AT and G-GC rule do not form non-specific triplexes, indicating that the triplex formation is indeed sequence specific.

Thus, for any given sequence in the regulatory region a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression. Examples of such suppression of gene expression in cells treated with TFOs include knockout of episomal supFG1 and endogenous HPRT genes in mammalian cells (Vasquez et al., Nucl Acids Res. 1999; 27:1176-81, and Puri, et al, J Biol Chem, 2001; 276:28991-98), and the sequence- and target specific down-regulation of expression of the Ets2 transcription factor, important in prostate cancer etiology (Carbone, et al, Nucl Acid Res. 2003; 31:833-43), and the pro-inflammatory ICAM-1 gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both downregulation and upregulation of expression of endogenous genes (Seidman and Glazer, J Clin Invest 2003; 112:487-94). Detailed description of the design, synthesis and administration of effective TFOs can be found in U.S. Patent Application Nos. 2003 017068 and 2003 0096980 to Froehler et al, and 2002 0128218 and 2002 0123476 to Emanuele et al, and U.S. Pat. No. 5,721,138 to Lawn.

Regardless of the methods described hereinabove, the present invention may also be effected by using mutant plants or plant variants, which do not accumulate these metabolites or compounds (1, 16). Such plants can be used for expressing and/or purifying the polypeptide of interest. Alternatively, such plants can be crossed with the transgenic plants expressing the polypeptide as described hereinabove. Next generations will include plants, which both express the polypeptide of interest and produce low levels of undesired compounds.

Plants generated or selected according to the above is preferably capable of accumulating less than 50% of average volume of undesired compounds in the trichome cells of the pant species.

The present invention also envisages a method of producing a polypeptide of interest in plant trichomes. Such polypeptides can be endogenous to the trichome or exogenous polypeptides, which can be used as pharmaceuticals (e.g., antibodies, antigens, ligands, growth factors, enzymes, structural proteins), industrial proteins and enzymes, therapeutics for veterinary use, proteins for molecular laboratories and diagnostics, nutraceuticals or cosmeceuticals.

The method is effected by expressing the polypeptide in the plant trichomes, as described above, and down-regulating a level of at least one molecule endogenous to the plant trichomes wherein such a molecule is capable of interfering with the expression accumulation or stability of the polypeptide of interest.

Plants which may be utilized for trichome specific expression in accordance with the present invention, are preferably selected or generated capable of generating (i) a trichome size of at least 10%, at least 20%, at least 30%, at least 40%, at least 50%, at least 80% above average size of the plant species; (ii) leaf surface size at least 5%, at least 10%, at least 15%, at least 25%, at least 30%, at least 40% above average size of the plant species; and/or (iii) total leaf number at least 10%, at least 20%, at least 30%, at least 40%, at least 50%, at least 80% above average leaf number of the plant species; (iv)

trichome density on the abaxial size of the leaf at least 10%, at least 20%, at least 30%, at least 40%, at least 50%, at least 80% above average trichome density of the plant species; (v) trichome density on the adaxial size of the leaf at least 100% above average trichome density of the plant species; (vi) shoot internode length of at least 5%, at least 10%, at least 15%, at least 25%, at least 30%, at least 40% above average length of the plant species; (vi) trichome density above 50,000 trichomes/gr leaf tissue; and/or (vii) trichome shape different than that of the plant species.

Plant architecture can be designed using genetic or non-genetic approaches [Weston (1989) J. Amer. Soc. Hort. Sci. 114:492-498; Antonious (2001) J. Environ. Sci. Health B. 36(6):835-48].

A number of genes which are associated with trichome development and morphogenesis were revealed through genetic studies. These genes may regulate trichome initiation, division rate of trichome cells and/or trichome cell ploidy number. A mutation in the TTG gene (GenBank Accession Nos. TTG1-AT5G24520, TTG2-AT2G37260) results in loss of leaf trichomes. Another example may be AGL16 (GenBank Accession No. NM_115583), a recently discovered MADS-box gene that is expressed in trichomes [Alvarez-Buylla (2000) Plant J. 24:457-466]. Yet another example is, KIC (GenBank Accession No. AY363866), a novel $Ca^{2+}$ binding protein with one EF-hand motif, which interacts with a microtubule motor protein and regulates trichome morphogenesis [Reddy Plant Cell. (2004) 16:185-200]. Other genes, which affect trichome size and/or distribution, include but are not limited to the UPL family of genes (e.g., UPL3, GenBank Accession No. AY265959), STICHEL [GenBank Accession No. AF264023, ligenfritz et. al. (2003) Plant Physiol. 131: 643-55], COT1 [Szymanski et. al. (1998) Genetics. 149:565-77], ZWICHEL (GenBank Accession No. AF002678, Oppenheimer et. al. (1997) Proc Natl Acad Sci USA. 10; 94:6261-6], GL1 (GenBank Accession No. AF263690), GL3 (GenBank Accession No. AT5G41315), GL2 (Acc. No. AT1G79840.1). It is conceivable that such genes when over-expressed may increase trichome size and/or distribution. For example, the GL-3 homologue R gene of maize causes trichome formation when over-expressed in *Arabidopsis* [Schellmann (2002) EMBO J. 21:5036-5046], indicating that such a manipulation is feasible. Overexpression of heterologous genes in plants is further detailed hereinbelow.

Non-transgenic approaches for modifying trichome size and/or distribution include chemical or physical mutagenesis [Szymanski et. al. (1998) Plant Cell. 10:2047-62], somaclonal variation [Saieed et. al. (1994) Tree Physiol. 14:17-26; Guo et. al. (2003) Shi Yan Sheng Wu Xue Bao. 36:202-8] and induction of polyploidy [Melaragno et. al. (1993) Plant Cell. 5:1661-1668].

Trichome density can be increased by exposure to differentiating factors (i.e., non-genetic approaches). For example, day length (16). Alternatively, physiological concentrations of ethylene have been shown to promote trichome formation [Kazama (2001) Plant Physiol. 117:375-83]. γ-radiation can be used to induce trichome formation [Negata (1999) Plant Physiol. 120:133-120].

Alternatively or additionally, trimming may be used to increase the number of leafs of the plant and as such increase the number of trichomes (see Example 7 of the Examples section).

Plants of the present invention are preferably sterile (i.e., having no viable pollen or seeds) to prevent spreading of genetic material to the surrounding environment. Sterilized plants can selected from mutant plants produced by for example chemical mutagenesis, physical mutagenesis or by somaclonal variation. Alternatively sterilized plants can be generated by silencing of fertility genes [Siaud et. al. (2004) EMBO J. 23:1392-401; Suzuki et. al. (2004) Plant J. 37:750-61; Li et. al. (2004) Plant Cell. 16:126-43; Krishnakumar and Oppenheimer (1999) Development. 126:3079-88].

Once plants are produced in accordance with the present invention, trichome content is purified to extract the molecules expressed therein or the products thereof.

Mechanical and chemical methods of isolating trichomes and trichomes exudates and content are known in the art. Such methods include the use of solvent containing microcapillary for dissolving the exudates. Measures are taken, though, to select a solvent which does not interfere with the activity or stability of molecules thus purified. Another method for removing trichomes include the use of forceps. A more efficient method for isolating exudates is by washing the surface with an organic solvent. Again, measures are taken to select a solvent which does not interfere with the activity or stability of molecules thus purified. Trichomes may also be produced by brushing surfaces, shaking in an aqueous solution with an abrasive or freezing the tissue and then brushing [see McCaskill (1992) Planta 187:445-454; Wang (2001) Nature Biotechnology 19:371-374].

In order to facilitate collection of the trichome-produced molecule, the present inventors have devised a novel approach for large-scale collection of trichome exudates and/or their content. This approach is simple to execute, does not require special technical skills, is cost effective and enables collection of large amounts of trichome exudates and content.

Trichome content collection according to the present invention is effected by incubating a trichome containing plant tissue in a liquid (e.g., water) such that trichome exudates and content is released into the liquid. To avoid leaching of tissue components other than trichome, liquid incubation is effected while avoiding friction between the trichome containing plant tissue and a solid surface. Thereafter, the liquid is collected, thereby harvesting the trichome exudates and content.

For example, trichome containing plant tissues, such as, shoots, leaves and flowers collected from plants can be incubated for 30-60 seconds under agitation (60 times per minute) in water or any other liquid, which allows release of trichome content and exudates, while avoiding leaching of other tissue components. Preferably avoided are non-polar solvents, such as chloroform and hexane.

The liquid is preferably supplemented with antioxidants such as citric acid, ascorbic acid and sodium bisulfite, which reduce the activity of trichome components (e.g., PPO, see Example 5 of the Examples section interfering with purification of the molecules.

Further purification of the molecules can be effected using any chemical or biochemical method known in the art depending on the chemical nature of the molecule and its intended use. Such methods include, but are not limited to, chromatography methods such as thin layer, affinity, gel filtration and ion-exchange.

Collection of trichome exudates and content can be effected manually or by employing a collection apparatus specifically designed for such a purpose.

Thus, the present invention also envisages an apparatus for mechanical harvesting of trichomes and/or trichome exudates and content (illustrated in FIG. 4a), which is referred to herein as apparatus 10.

Apparatus 10 includes a collector 12 (e.g., brush, forceps, arm) which is designed and configured for collecting trichomes and/or trichome exudates and content from a trichome containing plant tissue 14. Accordingly, collector 12 includes a collecting mechanism 13 for holding plant tissue 14 and a fluid filled reservoir 16 including fluid 18 in which plant tissue 14 is agitated by collecting mechanism 13.

Reservoir 16 also serves for storing collected trichomes and/or trichome exudates and content.

As is illustrated in FIGS. 4b-c, to enable agitation of plant material 14 within the fluid of reservoir 16, apparatus 10 (collector 12) includes a vibrating mechanism 20 which is fitted with a motor or servo and a power unit either to collecting mechanism 13 (FIG. 4b) or to reservoir 16 (FIG. 4c). Apparatus 10 may also include an actuating unit 22 and a timer 24 communicating with actuating unit 22. Reservoir 16 may also include at least one liquid channel 26 and pump 28 for transferring the liquid with the trichomes out of the reservoir and into collection containers or directly to a chromatography device for further separation and molecule isolation.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Cloning Promoter Regions of Trichome Expressed Genes and Identifying Trichome-Active Promoters Promoters suitable for expressing proteins in trichomes were identified by sequencing the genomic DNA upstream region of various cDNAs obtained from genes expressed in leaf tissues.

Materials and Methods

Isolation and Cloning of Trichome Promoter Sequences in a Binary Vector:

The NCBI database of 126,000 tomato expressed sequence tags (ESTs) (including 5,000 ESTs originated from cDNA libraries originated from the trichome tissues) and all transcribed nucleotide sequences described in literature or directly submitted to NCBI (cDNAs) were used for the identification of trichome active promoters. Keywords representing each sequence and expression pattern thereof were collected and stored in a database.

LEADS™ software (Compugen, Ill.) was used for clustering and assembling the tomato sequences and provided more than 20,000 clusters representing different genes. An expression profile annotative summary was designed for each cluster by pooling all keywords of each sequence represented in the cluster. Clusters were selected based on trichome EST number and percentage out of total ESTs present in each cluster. Clusters were analyzed for ORFs using Vector NTI suite (InforMax, U.K.) version 6. ORFs of each gene were compared to GenBank database, using Blast (Hypertext Transfer Protocol://World Wide Web (dot) ncbi (dot) nlm (dot) nih (dot) gov/BLAST/) and for the highest homologous ORF the position of the ATG start codon and stop codon was compared. Accordingly, most of the sequences described herein were predicted to posses the full length ORF. Clusters were classified as trichome-specific (i.e. more than 90% of ESTs in a cluster were originated from trichome cDNA libraries) or trichome expressed (i.e. at least one of the ESTs in a cluster was originated from trichome cDNA libraries).

RT-PCR—To verify the levels of expression and trichome specificity Reverse Transcription following quantitative (Real-Time) PCR (RT-qPCR) was performed on total RNA extracted from either leaves, trichome cells or leaves minus trichome cells.

mRNA levels were measured for three genes, previously predicted bioinformatically to express to high levels and specifically in trichome cells.

Trichome cells were harvested from tomato mature leaves by first freezing the leaves, just above liquid nitrogen and then brushing both sides of the leaves with paint brush, previously chilled in liquid nitrogen. Total RNA was extracted from leaves, trichome cells or leaves minus trichome cells of tomato using RNEASY plant mini kit (Qiagen, Germany) using the protocol provided by the manufacturer. Reverse transcription was performed using 1.5 μg total RNA, using 300 U Super Script II Reverse Transcriptase enzyme (Invitrogen), 225 ng random deoxynucleotide hexamers (Invitrogen), 500 μM dNTPs mix (Takara, Japan), 0.2 volume of ×5

RT buffer (Invitrogen), 0.01M DTT, 60U RNASIN (Promega), DEPC treated DDW was added up to 37.5 µl.

RT reactions were incubated for 50 min at 42° C., followed by 70° C. for 15 min. cDNA was diluted 1:20 in Tris EDTA, pH=8. 5 mL of the diluted cDNA was used for qPCR.

To normalize the expression level between the different tissues specific primers were designed for the following housekeeping genes: Actin (SEQ ID NO: 72), GAPDH (SEQ ID NO: 73), and RPL19 (SEQ ID NO: 74). The following primers were used for qPCR: Actin F primer: CCACATGC-CATTCTCCGTCT (SEQ ID NO: 77), R primer GCTTTTCTTTCACGTCCCTGA (SEQ ID NO: 78); GADPH F primer TTGTTGTGGGTGTCAACGAGA (SEQ ID NO: 79), R primer ATGGCGTGGACAGTGGTCA (SEQ ID NO: 80); RPL19 F primer CACTCTGGATATGG-TAAGCGTMGG (SEQ ID NO: 81), R primer TTCTTG-GACTCCCTGTACTTACGA (SEQ ID NO: 82); TR2 F primer tctcttcaattaggtacccgtcttg (SEQ ID NO: 83), R primer TGAATTTTGCCGTCATTGTCC (SEQ ID NO: 84); TR4 F primer GGGTTTAGACGTATCCGAAGGTC (SEQ ID NO: 85), R primer GCTCGTTTCCAATTTTCAGTAGAGA (SEQ ID NO: 86); TR5 F primer TTACGTGCCCAACT-GAACACA (SEQ ID NO: 87), R primer CAATGCAAT-CAGCCCATGC (SEQ ID NO: 88).

qPCR was performed on cDNA (5 µL), using ×1 iQ™ SYBR Green super mix (BioRad), forward and reverse primers 0.3 µM each, and DDW was added up to 20 µL.

qPCR reaction was performed in iCycler real-time PCR machine (BioRad) 95° C. for 3 min, 40 times of 95° C. for 15 sec and 1 min at 60° C., followed by 95° C. for 15 sec, 60° C. for 60 sec, and 70 times of 60° C. for 10 sec+0.5° C. increase in each cycle.

The levels of expression (Qty) measured in the qPCR were calculated using the efficiency (E) of the amplification reaction and the corresponding C.T. (the cycle at which the samples crossed the threshold) $Qty=E^{-C.T.}$. This calculation method assumes that the efficiencies of the reactions of the GOI (gene of interest) and of the housekeeping genes are similar. In general the efficiencies of the reactions were 100%+/−5%.

Results are summarized in FIGS. 6a-d.

FIGS. 6a-d show that all three selected genes (i.e. TR2, TR4, and TR5) were expressed at high levels, up to 21 times higher than the housekeeping genes, in trichome cells. In all cases expression was higher in trichomes compared to leaves, and in *L. hirsutum* compared to *L. esculentum* plants. Hence the promoter sequences, upstream to the gene sequences, were cloned from *L. hirsutum* gDNA.

In order to clone these promoter sequences and 5' untranslated region (5' UTR) upstream of the ATG starting codon, total genomic DNA was extracted from plant leaf tissues of 4 week old plants of the following species: cultivated tomato (*Lycopersicon esculentum*, var 870), wild tomato species (*Lycopersicon hirsutm*, var LA 1777 and *Lycopersicon pennellii*, var LA 716), tobacco (*Nicotiana tabaccum*, var NN) or cotton (*Gossypium hirsutum* var *Acala* 23). DNA extraction was effected using DNA extraction kit (DNEASY plant mini kit, Qiagen, Germany). Inverse PCR (IPCR), DNA digestion, self-ligation, and PCR reaction were performed on genomic DNA, following a well established protocol [Hypertext Transfer Protocol://World Wide Web (dot) pmci (dot) unimelb (dot) edu (dot) au/core facilities/manual/mb390.asp] with the following modifications. To avoid mistakes in the IPCR, first the genomic sequence of the 5' sequence of a relevant cDNA (i.e. including introns) was identified to produce Genomic Island (GI). The desired region from the genomic DNA was PCR-amplified using direct oligonucleotide primers designed based on the cDNA cluster sequence, as was predicted by the Leads software (Compugen, Ill.). PCR reaction was performed in a DNA thermal cycler, using common PCR conditions (for example: 92° C./3 min followed by 31 cycles×[94° C./30 sec; 56° C./30 sec; 72° C./3 min] followed by 72° C./10 min). PCR products were purified using PCR purification kit (Qiagen) and sequencing of the amplified PCR products was performed, using ABI 377 sequencer (Amersham Biosciences Inc).

Primer sequences of each plant and the resultant GI sequence (i.e. the genomic sequence which was amplified using the primers) are listed in Table 1, below.

TABLE 1

| ID/Plant | Forward primer/<br>SEQ ID NO: | Reverse primer/<br>SEQ ID NO: | Product size/<br>SEQ ID NO: |
|---|---|---|---|
| TR2 (*L. hirsutum*) | atggaagtaactttgttgtatagtac/<br>SEQ ID NO: 1 | GCCAGTGATCACCATAAGGAG/<br>SEQ ID NO: 2 | 376/SEQ ID NO: 3 |
| TR4 (*L. hirsutum*) | Ttctttggttcttcaatgttgg/<br>SEQ ID NO: 4 | TTTGTAATGTCATTGGGAGGTC/<br>SEQ ID NO: 5 | 410 bp of 5' prime region out of about 3500 bp of amplified PCR product SEQ ID NO: 6; Note ~3500 bp were amplified by PCR, out of which only 5' prime 410 bp were sequenced |
| TR5 (*L. hirsutum*) | Gggtaatattcatttgattttcc/<br>SEQ ID NO: 6 | AACCTGCTTTACATGTTTCAAG/<br>SEQ ID NO: 7 | 431 bp/SEQ ID NO: 9 |

To increase amplification efficiency as needed a different amplification technique [UP-PCR (20)] was employed. Briefly, UP-PCR technique was used in order to amplify unknown upstream region of a known cluster sequence. Generally, the procedure involved four oligonucleotide primers: two sequence specific primers (SPs, external and internal) (listed below), both having the same orientation of 3' end towards the unknown, yet desired, 5' region of the gene, and two universal walking primers (WP28 and sWP). Reaction mixtures were generated as follows: sample mixture (SM)— genomic DNA of appropriate plant (tomato or cotton) species (30-40 ng), WP28 primers (20 pmol), and DDW was added to a final volume of 10 μl; Polymerase mixture (PM)—dNTPs (Roche, Switzerland) (10 mM each), Expand Long Template Enzyme mix (Roche, Switzerland) (1U), 10× buffer supplied with the enzyme and DDW was added to a final volume of 8 μl. SM was placed in a thermocycler (Biometra, USA), where it was subjected to an amplification program of 1 minute at 90° C., held (pause) at 80° C. until PM was added, 30 seconds at 15° C., 10 minutes at 25° C., 3 minutes at 68° C., held at 90° C. until the external SP (2 μl of 10 μM concentration) was added. The process was followed by external PCR reaction of 30 seconds at 92° C., 10 seconds at 94° C., 30 seconds at 65.5° C., 3 minutes at 68° C., for 30 cycles followed by final extension of 10 minutes at 68° C.

External PCR products (diluted 5000-25000 fold) were used as template and subjected to amplification using specific internal sWP and SP (30 pmol each) primers, 1U Ex Taq (Takara), in 50 μl reaction volume. Internal PCR reactions were subjected to an amplification program of 2 minutes at 92° C., followed by 30 seconds at 94° C., 30 seconds at 58° C., and 3 minutes at 72° C. for 30 cycles and a final extension of 10 minutes at 72° C. IPCR/Up-PCR products were purified (PCR Purification Kit, Qiagen, Germany) and sequenced (ABI 377 sequencer, Amersham Biosciences Inc). Table 2, below, lists primers and products of IPCR/Up-PCR reactions.

For cloning the putative promoters and 5' UTRs, an additional PCR amplification was effected using a new set of primers (below) which included 8-12 bp extensions having one restriction site (HindIII, SalI, XbaI, BamHI, or SmaI) on the 5' prime end thereof. For each promoter, restriction sites that do not exist in the promoter sequence were selected. Moreover, the restriction sites in the primer sequences were design such that the resultant PCR products were cloned into the binary vector pPI in the right orientation, upstream of the GUS reporter gene.

The plasmid pPI was constructed by inserting a synthetic poly-(A) signal sequence, originating from pGL3 basic plasmid vector (Promega, Acc No U47295; bp 4658-4811) into the HindIII restriction site of the binary vector pBI101.3 (Clontech, Acc. No. U12640).

Table 3, below lists the restriction enzymes (enz.) containing primers, and the SEQ ID NO: of the resultant PCR prod-

TABLE 2

| ID/Plant | Amplification method | External primers sWP28/ SEQ ID NO: | SP (external)/ SEQ ID NO: | Internal primers sWP/ SEQ ID NO: | SP (internal)/ SEQ ID NO: | Product SEQ ID NO: |
|---|---|---|---|---|---|---|
| TR2/L. hirsutum | UP-PCR | TTTTTTTTT TGTTTGT TGTGGGG GTGT/SEQ ID NO: 10 | GGAAGTTT AAGTAGTG GGCTTG/SEQ ID NO: 11 | TTTTTG TTTGTT GTGGG/ SEQ ID NO: 12 | GTGGGCTT GGTGGTAG ATTC/SEQ ID NO: 13 | 14 |
| TR4/L. hirsutum | UP-PCR | TTTTTTTTT TGTTTGT TGTGGGG GTGT/SEQ ID NO: 10 | GTTGAGTC CACGAGCA GACAC/SEQ ID NO: 15 | TTTTTG TTTGTT GTGGG/ SEQ ID NO: 12 | CGAGCAGA CACTGTCA GAGG/SEQ ID NO: 16 | 17 |
| TR5/L. hirsutum | UP-PCR | TTTTTTTTT TGTTTGT TGTGGGG GTGT/SEQ ID NO: 10 | ATTCACAA GGTTGTGG ATGAGG/SEQ ID NO: 18 | TTTTTG TTTGTT GTGGG/ SEQ ID NO: 12 | GATGAGGT GTTTGGGT GCAC/SEQ ID NO: 19 | 20 | ucts. Restriction sites within each primer are indicated by bold letters.

TABLE 3

| ID/Plant | Forward primer- Restriction enz./ SEQ ID NO: | Reverse primer- Restriction enz./ SEQ ID NO: | Product SEQ ID NO: |
|---|---|---|---|
| TR2 (L. hirsutum) | (HindIII): 5'-AATTTAAGCTTGTGTCG CTCAGCCCCTACTC-3'/ SEQ ID NO: 21 | (SalI): 5'-AAATTGTCGACATCTCAA CTTGTTGCACTGAATTG-3'/ SEQ ID NO: 22 | 23 |
| TR4 (L. hirsutum) | (SalI): 5'-CCTAGTCGACGGTGTTA AATGGTGGGTTGG-3'/ SEQ ID NO: 24 | (BamHI): 5'-TTGGATCCGAGCAGAC ACTGTCAGAGG-3'/ SEQ ID NO: 25 | 26 |

TABLE 3-continued

| ID/Plant | Forward primer-<br>Restriction enz./<br>SEQ ID NO: | Reverse primer-<br>Restriction enz./<br>SEQ ID NO: | Product<br>SEQ ID<br>NO: |
|---|---|---|---|
| TR5<br>(L. hirsutum) | (HindIII):<br>5'-TTTCCAAGCTTGACCTG<br>CTCTGATACCAATTG-3'/<br>SEQ ID NO: 27 | (BamHI):<br>5'-CCGGATCCTCGTAAGG<br>AGTTTGTAATATG -3'/<br>SEQ ID NO: 28 | 29 |

PCR products were purified (PCR Purification Kit, Qiagen, Germany) and digested with the restriction sites according to the primers used (Roche, Switzerland). The digested PCR products were re-purified and cloned into the binary vector pPI, which was digested with the same restriction enzymes. PCR product and the linearized plasmid vector were ligated using T4 DNA ligase enzyme (Roche, Switzerland).

Example 2

Cloning of Trichome Active Promoter Sequences

Several genomic sequences were already described and validated in the literature as trichome-specific promoters. In most cases promoter validation was effected in tobacco plants. However, none of these sequences were analyzed in tomato plants. Hence there is no way to predict which of these promoters will be active in tomato.

Materials, Methods and Results

A previously described tobacco promoter, (8) was isolated from genomic DNA (gDNA) of *Nicotiana tabaccum*, var *Samsun* NN using two sets of overlapping primers: 1. Forward—5'-AAATCTAGACTACCATCGCTAGTAATCGTG-3' (SEQ ID NO: 30) and Reverse—5'-GTTGAAGAACTG-CATCCCGGGAGG-3' (SEQ ID NO: 31) to provide the sequence product set forth in SEQ ID NO: 32 (, TR25-2, SEQ ID NO: 67); 2. Forward—5'-AAATCTAGATAAGT-TGATAAAGCTAATTTCTC-3' (SEQ ID NO: 33) and Reverse—5'-TTTCCCGGGACCTGGAGGCAATC-3' (SEQ ID NO: 34) to provide the sequence product set forth in SEQ ID NO: 35 (TR25-3, SEQ ID NO: 68).

Primers sequences included additional restriction sites XbaI (Forward primers) and SmaI (Reverse primers), indicated in bold letters, to facilitate further cloning.

Each PCR product was digested with XbaI and SmaI (Roche) and introduced via ligation, using T4 DNA ligase (Roche), into pPI plasmid, digested with the same restriction enzymes.

A cotton promoter, previously described in (7), was isolated from gDNA of *Gossypium hirsutum*, var. *Acala* 23, and *Gossypium barbadense* var. *Pima* 15 using the primers: Forward—5'-TATAAGCTTTAAGTTTAAATCCTATTG-TAGTG-3' (SEQ ID NO: 36) and Reverse—5'-CGGATC-CATTAATCACAAGAAAAAC-3' (SEQ ID NO: 37) to provide a genomic amplified sequence of Acala as set forth in SEQ ID NO: 38 (27A) and a genomic amplified sequence of Pima as set forth in SEQ ID NO: 39 (27P).

Primer sequences included additional restriction sites HindIII (Forward primer) and BamHI (Reverse primer), indicated in bold letters, to facilitate further cloning. PCR products were digested with HindIII and BamHI (Roche) and introduced via ligation, using T4 DNA ligase (Roche), into pPI plasmid, digested with the same restriction enzymes.

Example 3

Cloning of Tomato PPO Promoters and Signal Peptide

Tomato polyphenol oxidase (PPO, GenBank Accession No: Z12833 for PPOA, GenBank Accession No. Z12836 for PPOD) is the major protein in type VI trichomes of tomato (5). Hence it was expected that the promoter region upstream the PPO gene will direct the expression of foreign genes to the trichome cells. PPO is encoded by closely related, seven members, gene family. A previous publication identified which of the gene family members are preferably expressed in the trichome cells (5).

The genomic sequence of the PPO gene family was published. Still, in most cases, promoter activity was not tested for the sequences upstream of the genes.

Materials, Methods and Results

The promoter sequence of PPOA and PPOD was cloned from wild tomato (*Lycopersicon pennellii*) and cultivated tomato (*Lycopersicon esculentum*), respectively. Cloning of the putative promoter region of PPOA was effected by amplifying the genomic sequence upstream of the coding region, using the primers:
Forward—5'-AAAATTTGGGATCTAGAAGGTGAGG-3' (SEQ ID NO: 40) and Reverse—5'-CTGGATCCTAT-TGCTAGCTTTGGATGAAG-3' (SEQ ID NO: 41). The resultant genomic DNA amplified thereby is set forth in SEQ ID NO: 42 (T8). Primer sequences include additional restriction sites XbaI (Forward primer) and BamHI (Reverse primer), indicated in bold, to facilitate further cloning.

The resultant PCR product was digested with XbaI and BamHI (Roche) and introduced via ligation, using T4 DNA ligase (Roche), into pPI plasmid, digested with the same restriction enzymes.

Cloning of the putative promoter region of PPOD was performed by amplifying the genomic sequence upstream of the coding region, using the primers: Forward—5'-ATG-GAAAAGCTTATGGACAGACTAAAACAC-3' (SEQ ID NO: 43) and Reverse—5'-CTGGATCCTGT-TGCTAGCTTTTGAATGAAA-3' (SEQ ID NO: 44). The resultant genomic DNA amplified thereby is set forth in SEQ ID NO: 45 (T11).

Primer sequences included additional restriction sites HindIII (Forward primer) and BamHI (Reverse primer), indicated in bold, to facilitate further cloning.

PCR product was digested with HindIII and BamHI (Roche) and introduced via ligation, using T4 DNA ligase (Roche), into pPI plasmid, digested with the same restriction enzymes.

Vast accumulation of PPO in trichomes is largely governed by protein import and storage within the thylakoid lumen of plastids, such as chloroplasts and leucoplasts (5, 12, 28). Protein import into the lumen is directed by a signal peptide on the amino terminal of the immature polypeptide of PPO.

The immature polypeptide is imported first into the plastid stroma where the primary part of the signal peptide is cleaved. Later on, the second part of the signal peptide is cleaved, while the polypeptide is crossing the thylakoid membrane and the mature polypeptide is entering into the thylakoid lumen (28).

Hence to facilitate the accumulation of foreign proteins in trichomes, protein import into plastids might be crucial.

To test protein import, the native signal peptide of either PPOA or PPOD was amplified together with the putative promoter of each gene. Amplified products were cloned into pPI and fused, in frame, to the GUS reporter gene. Amplification of PPOA promoter together with only the initial part of the signal peptide, which directs protein to the stroma was done using the following primers: Forward—5'-AAAATTTGGGATCTAGAAGGTGAGG-3'(SEQ ID NO: 46, XbaI restriction site is indicated in bold) and Reverse—5'-ACATGAAACTTTGAATGCTTTG-3' (SEQ ID NO: 47). The genomic amplified sequence of PPOA is set forth in SEQ ID NO: 48.

PCR product was digested with XbaI (Roche) and introduced via ligation, using T4 DNA ligase (Roche), into pPI plasmid, digested with XbaI and SmaI restriction enzymes.

Amplification of PPOD promoter and signal peptide which directs protein to the stroma was effected using the following primers: Forward—5'-ATGGAAAAGCTTATGGACAGAC-TAAAACAC-3' (SEQ ID NO: 49) and Reverse—5'-TTC-CCGGGACATGAAACTTTGAATGCTTTG-3' (SEQ ID NO: 50). Genomic amplified sequence of PPOD is set forth in SEQ ID NO: 51.

Primer sequences included additional restriction sites HindIII (Forward primer) and SmaI (Reverse primer) to facilitate further cloning.

PCR product was digested with HindIII and SmaI (Roche) and introduced via ligation, using T4 DNA ligase (Roche), into pPI plasmid, digested with the same restriction enzymes.

Amplification of PPOD promoter and signal peptide which directs protein to the lumen was done using the following primers: Forward—5'-ATGGAAAAGCTTATGGACAGAC-TAAAACAC-3' (SEQ ID NO: 52) and Reverse—5'-AAC-CCGGGAGCCGATGCAGCTAATGG-3' (SEQ ID NO: 53). The resultant genomic amplified sequence of PPOD is set forth in SEQ ID NO: 54.

Primer sequences included additional restriction sites HindIII (Forward primer) and SmaI (Reverse primer), indicated in bold, to facilitate further cloning.

PCR product was digested with HindIII and SmaI (Roche) and introduced via ligation, using T4 DNA ligase (Roche), into pPI plasmid, digested with the same restriction enzymes.

Example 4

Expression of Therapeutic Proteins in Trichome Cells

Materials and Methods

The potential of trichomes to accumulate human therapeutic proteins can be estimated by expressing human interferon β gene or human growth hormone gene in trichome cells.

Materials and Methods

Cloning of human interferon β into a binary vector—The gene for human interferon β (INFB, GenBank Accession No. NM_002176) was amplified from human genomic DNA using the following primers: Forward: 5'-GGGATGAGCTA-CAACTTGCTTGGAT-3' (SEQ ID NO: 55) and Reverse: 5'-CTAGGAGCTCTTCAGTTTCGGAG-3' (SEQ ID NO: 56, a SacI restriction site on the primer is indicated in bold). The resultant sequence of the INFB gene is set forth in SEQ ID NO: 57.

Analysis of the INFB sequence revealed a codon usage that is similar to the codon usage of the tomato (data not shown).

The PCR product (SEQ ID NO: 57) was digested using SacI restriction endonuclease (Roche) and cloned into pPI binary vector digested with SmaI and SacI, hence replacing the GUS gene. The newly formed binary plasmid was designated pINFB. Sequence analysis of the INFB gene in pINFB revealed that the INFB sequence was cloned in the right orientation. Trichome promoters together or without a plastid transit peptides (summarized in Table 4 below) were further cloned upstream of the INFB gene in pINFB.

Cloning of human growth hormone into a binary vector—The mature polypeptide of the Human-growth hormone gene (HGH, GenBank Accession No: V00519) was produced synthetically using GeneArt service (Hypertext Transfer Protocol://World Wide Web (dot) geneart (dot) de/). The sequence was adjusted according to the tomato codon usage, while avoiding, as much as possible, high GC content and low complexity of DNA sequences. An ATG was added as a first codon to the mature polypeptide enabling sufficient translation. The restriction sites of SmaI and SacI were added to the gene at the 5' prime end and 3' prime end, respectively. The sequence of the HGH gene is set forth in SEQ ID NO: 58.

The gene clone was provided in a PCR script plasmid vector. The gene was digested out of the plasmid using SmaI and SacI restriction endonucleas (Roche) and cloned into pPI binary vector, replacing the GUS gene. The newly formed binary plasmid was named pHGH. Sequence analysis revealed that the inserted HGH gene in pHGH was cloned in the right orientation. Trichome promoters with or without a plastid transit peptides (summarized in Table 4, below) were further cloned upstream of the HGH gene in pHGH.

*Agrobacterium* transformation of binary plasmids expressing heterologous genes—*Agrobacterium tumefaciens* (strains LBA4404) competent cells were transformed with 0.5 μl binary plasmid by electroporation, using a MicroPulser electroporator (Biorad, USA), 0.2 cm cuvettes (Biorad, USA) and EC-2 electroporation program (Biorad, USA). Cells were incubated in LB medium at 28° C. for 3 hours and plated on LB-agar plates supplemented with 50 mg/L kanamycin (Sigma, USA) and 250 mg/L streptomycin. Plates were incubated at 28° C. for 48 hours until *Agrobacterium* colonies grew. These colonies were subsequently used for tobacco or tomato plant transformation.

Plant transformation and cultivation—Table 4, below, summarizes the constructs which were introduced into tomato plants.

TABLE 4

| Promoter | species | Transit peptide | gene | binary |
|---|---|---|---|---|
| 35S | CaMV | No | GUS | pPI |
| TR2 | L. hirsutum | No | GUS | pPI |
| TR4 | L. hirsutum | No | GUS | pPI |
| TR5 | L. hirsutum | No | GUS | pPI |
| TR8 | L. pennellii | No | GUS | pPI |
| TR8 | L. pennellii | Stroma | GUS | pPI |
| TR11 | L. esculentum | No | GUS | pPI |
| TR11 | L. esculentum | Stroma | GUS | pPI |
| TR11 | L. esculentum | Lumen | GUS | pPI |
| TR25-2 | N. tabaccum | No | GUS | pPI |
| TR25-3 | N. tabaccum | No | GUS | pPI |
| TR27-A | G. hirsutum | No | GUS | pPI |
| TR27-P | G. barbadense | No | GUS | pPI |
| TR2 | L. hirsutum | No | INFB | pINFB |

TABLE 4-continued

| Promoter | species | Transit peptide | gene | binary |
|---|---|---|---|---|
| TR4 | L. hirsutum | No | INFB | pINFB |
| TR5 | L. hirsutum | No | INFB | pINFB |
| TR8 | L. pennellii | No | INFB | pINFB |
| TR8 | L. pennellii | Stroma | INFB | pINFB |
| TR11 | L. esculentum | No | INFB | pINFB |
| TR11 | L. esculentum | Stroma | INFB | pINFB |
| TR11 | L. esculentum | Lumen | INFB | pINFB |
| TR25-2 | N. tabaccum | No | INFB | pINFB |
| TR25-3 | N. tabaccum | No | INFB | pINFB |
| TR27-A | G. hirsutum | No | INFB | pINFB |
| TR27-P | G. barbadense | No | INFB | pINFB |
| TR2 | L. hirsutum | No | HGH | pHGH |
| TR4 | L. hirsutum | No | HGH | pHGH |
| TR5 | L. hirsutum | No | HGH | pHGH |
| TR8 | L. pennellii | No | HGH | pHGH |
| TR8 | L. pennellii | Stroma | HGH | pHGH |
| TR11 | L. esculentum | No | HGH | pHGH |
| TR11 | L. esculentum | Stroma | HGH | pHGH |
| TR11 | L. esculentum | Lumen | HGH | pHGH |
| TR25-2 | N. tabaccum | No | HGH | pHGH |
| TR25-3 | N. tabaccum | No | HGH | pHGH |
| TR27-A | G. hirsutum | No | HGH | pHGH |
| TR27-P | G. barbadense | No | HGH | pHGH |

Tomato transformation—Tomato transformation was carried out according to Fillati et al. (19). Briefly, *Lycopersicon esculentum* cv. Micro-Tom cotyledons were used for *Agrobacterium* based plant transformation. The Micro-Tom seeds were surface sterilized for 10 min in a 3% sodium hypochlorite solution. The seeds were washed with DDW three times and soaked for three hours in fresh DDW, then plated into 0.5 L container with Nitsch medium, containing MS salts, 3% sucrose, Nitsch vitamins and 0.8% plant agar (Duchefa, Netherland). The PH was adjusted to 5.8 prior to autoclaving for 20 min at 121° C. 50 seeds where plated on 0.5 L sterilized container containing the germination medium and left at 25° C. in culture room, 16/8 hrs light/dark cycles, under light intensity of $(150\,\mu Em^{-2}S)$. Seedlings where grown for 8 days.

*Agrobacterium tumefaciens* strain LBA4404 carrying an intact vir region which can mediate the introduction of the T-DNA from the bacteria into plants. The binary vector plasmids, originated from pPI, were introduced into the strain LBA 4404 as described above.

For co cultivation, a single colony from freshly streak LB plate supplemented with 300 µg/ml streptomycin and 50 µg/ml kanamycin (Sigma) was used to inoculate 5 ml LB overnight shaking at 28° C. The inoculated 5 ml where added to 45 ml LB supplemented with 300 µg/ml streptomycin and 50 µg/ml kanamycin to additional overnight at the same conditions. The overnight culture where centrifuged for 3060 rpm for 10 minutes and rinsed with 50 ml MS medium.

2.5 ml of fine tobacco suspension culture where plated on petri dishes (100×25 mm) containing 50 ml of KCMS murashige minimal organics medium supplemented with 0.2 µg/ml 2.4D, kinetin 0.1 µg/ml, thiamine hydrochloride 0.8 µg/ml, potassium acid phosphate 200 µg/ml, biotin 0.5 µg/ml, folic acid 0.5 µg/ml, casein hidrolysat 80 µg/ml and plant agar 0.8%, PH 5.8 (Duchefa, Netherland).

Whatmann paper filter no. 1 (Whatmann) was autoclaved and placed on top the of the feeder plates. Any air bubbles and remaining tobacco suspension media were excluded. The plates were incubated for 24 hours under low light conditions $(10\,\mu m^{-2}S)$.

8 days old cotyledons were cut at both ends on MS medium and plated for 24 hours on the tobacco suspension plates in the same conditions.

The cotyledons were immersed in 5 ml of the rinsed *Agrobacterium* cells diluted in 50 ml MS medium in sterile Petri dish. The concentration of the bacteria was $\sim 5\times 10^8$ cfu/ml. Following 10 minutes the cotyledons were blotted carefully to remove any excess of bacterial suspension. 20 cotyledons were placed on the feeder plates for 48 hr for co-incubation with the bacteria under the same conditions.

Cotyledons were then transferred to 2 Zeatin Ribozide (ZR) regeneration medium (Duchefa, Netherland), containing 400 µg/ml carbenicillin or 150 Ticarcillin/potassium clavulanate to inhibit growth of *Agrobacterium* and Kanamycin 100 µg/ml to select for transformed tomato cells.

The cotyledons were transferred to fresh regeneration media after 1 month supplemented with 1 ZR 200 carbenicillin and 100 µg/ml Kanamycin.

Shoots where excised when they were approximately 1 cm long and transferred to 0.5 L containers supplemented with rooting media containing MS medium 50 µg/ml kanamycin, 100 µg/ml carbenicillin disodium, 2 µg/ml IBA (Duchefa, Netherland). After approximately ten days the rooted explants were transferred into soil, under 100% humidity. The humidity was reduced gradually for 24 hours. After 24 hr the plants were transferred to the greenhouse.

Testing Expression of Foreign Proteins in Trichomes:

A. GUS staining—Gus staining of tomato and tobacco plants was effected as previously described (15). Briefly: Leaves were fixed in 90% ice cold acetone for 15-20 minutes (on ice), followed by removal of acetone and a double tissue rinsing with the Working Solution [25 mM Sodium Phosphate (Sigma, USA) buffer pH=7, Ferricyanide (Sigma, USA) 1.25 mM, Ferrocyanide (Sigma, USA) 1.25 mM, Triton X-100 (Sigma, USA) 0.25%, EDTA (BioLab) 0.25 mM] for 15-20 minutes. Rinse solution was removed, replaced with Staining solution [Working solution with 5-bromo-4-chloro-3-indolyl-β-D-glucuronic acid (X-GlcA, Duchefa) solubilized in N,N-Dimethylformamide (BioLab) 1.5 mg/ml and Dithiothreitol (DTT, Bio Lab) 100 mM] and incubated in the dark (tubes wrapped with aluminum foil) over night at 37° C. Distaining was effected by sinking the plant tissue in 70% ethanol and heating at 50° C. for ~2 hours. The distaining step was repeated until the plant tissue became transparent except the blue stained regions. Distained plants were stored in 70% ethanol (BioLab) at room temperature.

ELISA—Human protein detection in plant tissues was effected using Human Interferon β ELISA Kit (R & D Systems) and Ultra-sensitive Human Growth Hormone ELISA Kit (Diagnostic Systems Laboratories, Inc), according to manufacture instructions.

Western Blot—Briefly, proteins extracted from the leaves were resolved on 12% Tris-HCl-Criterion gel (Bio-Rad Laboratories, Inc.) and transferred by electroporation onto PVDF membranes using the Bio-Rad Criterion Precast Gel System (100 V constant voltage at 4° C., 1.5 hours). Pre-stained SDS-PAGE standards (Bio-Rad Laboratories, Inc.) were used as molecular weight markers. Primary antibodies were diluted 1:500 and the secondary antibody-HRP conjugate was diluted 1:15,000. The following anti-recombinant protein polyclonal antibodies were used: goat (Santa Cruz) or sheep (Biosource) polyclonal anti human IFN-β, goat polyclonal anti human GH (Santa Cruz), rabbit polyclonal anti *E. coli*-glucuronidase (Molecular Probes). ECL and related reagents were obtained from Amersham Biosciences.

Bradford protein quantification test—Protein quantification was effected according to Bradford method [Bradford M., Analytical biochemistry, 72: 248 (1976)] using Bio-Rad Laboratories, Inc. reagent.

Results

GUS staining was performed on leaves of T1 tomato and tobacco plants transfected with a binary vector including putative trichome specific promoters upstream of a GUS gene. Control plants included wild-type tomato and tomato transfected with GUS under the constitutive CaMV S35 promoter (FIGS. 1b-c). As is shown in FIGS. 1d-h under the regulation of TR2, TR5, TR11, TR25 and TR27 promoters GUS was expressed in a trichome-gland specific manner (FIGS. 1d-h). A light blue color was also found in the stalk cell immediately attached to the gland and in non glandular tissues. Results for tomato T1 generation are summarized in Table 6, below.

TABLE 6

| Promoter | Signal peptide | No of Independent T1 plants | Avg grade | Range |
| --- | --- | --- | --- | --- |
| 35S | No | 9 | 2.1 | 0-5 |
| TR2 | No | 2 | 1.5 | 0-3 |
| TR5 | No | 6 | 0.2 | 0-1 |
| TR11 | No | 3 | 0 | 0 |
| TR11 | Stroma | 4 | 0 | 0 |
| TR11 | Lumen | 4 | 0.5 | 0-1 |
| TR25-2 | No | 8 | 0 | 0 |
| TR25-3 | No | 18 | 0.1 | 0-1 |
| TR27-P | No | 5 | 0.4 | 0-2 |

The results presented in Table 6 above indicate that TR2 and TR27-P are most effective in facilitating expression of heterologous genes in the tomato trichome. These results are of special significance since TR2 has never been described before as a trichome active promoter. Furthermore, the addition of a luman directing signal peptide seems to have facilitated expression in the trichome.

Example 5

Novel Methods for Mechanical Harvesting of Proteins from Trichomes

Materials and Methods

Harvesting of Trichome proteins:

Four harvesting protocols were attempted to optimize protein purification.

Protocol 1—Total trichome protein harvesting was performed by wiping fully expanded leaves with cotton swabs moistened with a solution of 200 mM Dithiothreitol (DTT, BioLab). Approximately 5-7 leaves were wiped per swab, with a total of about 1500 leaves. The crude trichome extract was squeezed from the swab using a syringe, and centrifuged (15000×g for 15 minutes at 4° C.). To adsorb phenolic compounds, the supernatant (approximately 70 ml) was treated with Polyvinylpolypyrrolidone (PVPP; Sigma, USA) for 10 minutes on a gentle stirrer followed by centrifugation (15000 g for 20 minutes) to remove the PVPP. Prior to application, PVPP was boiled in 10% HCl for 10 minutes, washed extensively with DDW, air-dried for storage and soaked for at least 3 hours in 200 mM DTT solution at 4° C. (ratios were 8-12 g PVPP/250 ml of 200 mM DTT, 1-1.5 g/60-85 ml extract). Extracts were concentrated in two steps of ammonium sulfate precipitation (20%, 75% of saturation). Solid ammonium sulfate (0%→20%: 114 g/1 L, 20%→75%: 382 g/1 L) was added to the extract until the desired concentration was reached while constant stirring. Thereafter the solution was held on ice for about 1 hour with occasional stirring. The precipitate was collected by centrifugation (15000×g for 20 minutes at 4° C.) and dissolved in 50 mM Tris-HCl, pH 7 and 30 mM NaCl.

Protocol 2—Trichome cells and exudates were harvested directly into DDW which contained chemicals with antioxidant activity (i.e., citric acid, ascorbic acid or sodium bisulfite). Tomato leaves and shoots were soaked in a container. Gentle shaking of the tissue in the liquid medium caused the explosion of the glandular trichome cells, type VI and VII (see FIG. 1a) and released the trichome exudates into the media. To eliminate the loss of significant amounts of liquid, tissues were lifted out of the medium and partially dried by shaking it vigorously, letting drops fall back to the container. Trichome yield was measured by inspecting the treated leaves. Trichome harvesting efficiency was calculated as the percentage of broken and exploded trichomes, out of total trichomes on a given leaf area.

Protocol 3—Trichome cells and exudates were harvested directly into a liquid media. Tomato leaves or shoots were put in a container, filled with tap water. The container was closed and centrifuged at 20 rpm for 5 minutes. To eliminate the loss of significant amounts of liquid, tissues were lifted out of the medium and partially dried by shaking it vigorously, letting drops fall back to the container. Trichome yield was measured by inspecting the treated leaves. Trichome harvesting efficiency was calculated by percentage of broken and exploded trichomes, out of total trichomes on a given leaf area.

Protocol 4—Trichome cells and exudates were harvested directly into a liquid media. Tomato leaves or shoots were put in a container, filled with tap water. The container was closed and water was poured on top of the leaves using pump which circulated the water in the container. Trichome yield was measured by inspecting the treated leaves. Trichome harvesting efficiency was calculated by percentage of broken and exploded trichomes, out of total trichomes on a given leaf area.

Results

Protein harvest, purification, yield—Protocol 1 was effected on a commercial tomato variety, grown in a commercial greenhouse, which was designed and used for tomato fruit harvest. Tomato (L. esculentum var 591) plants were grown for 3 months. Plant architecture was designed by leaving two main shoots for each plant. Using Bradford analysis it was possible to calculate total protein yield. Harvesting about 1,100 leaves yielded 16 mg total protein (0.1 mg/ml). Total protein yield was resolved on Nu-PAGE Novex Bis-Tris gel, 12% (Invitrogen) and protein bands were visualized by coomassie staining (FIG. 2). A band harboring of an estimated size of 60 kDa was predicted to be the mature PPO protein according to previous reports (12, 29). PPO is estimated to count for 60% of total proteins in the trichome.

It will be appreciated that although protocol 1 for protein harvesting is highly effective in collecting most of the trichome exudates, it is labor intensive and slow. The other described methods (2, 3, and 4) were tested to replace the mechanical harvesting step in method 1.

Tomato shoots (1 m long) were dipped in a container and were subjected to trichome mechanical harvesting using method 2, 3 or 4.

Results, showing the efficiency of each method are presented in the Table 7, below.

TABLE 7

| Method | Number of Shoots | Average Efficiency | Range Efficiency |
|---|---|---|---|
| 2 | 3 | 98 | 96-100 |
| 3 | 3 | 11.3 | 8-14 |
| 4 | 3 | 42 | 38-46 |

These results suggest that protocol 2 is the most effective for protein harvesting from trichomes.

High activity of PPO in trichome may affect protein harvesting and purification from trichomes. Thus, identification of chemicals which are strong antioxidants, non toxic, cheap and not affecting protein stability is mostly desired.

Three compounds were tested: citric acid, ascorbic acid and sodium bisulfite. Different concentrations of chemicals were used to identify the chemical with the highest antioxidant activity. Tomato (*L. esculentum*) young leaves (about 100 mg) were grinded at 4° C. in 200 µl of 10 mM Tris-HCl pH=8 buffer containing appropriate concentration of antioxidant (0.01-2.0% w/v), incubated for about 2 hrs at 4° C. and centrifuged at 14,000 rpm for 3 min in order to separate leaves-debris and liquid fraction. Decreasing of PPO activity was inspected by eliminating the production of brown color of the supernatant as a result of the oxidation of polyphenols. Table 8 below summarizes the minimal concentration that enables a decrease of 95% of PPO activity.

TABLE 8

| chemical | Efficient concentration |
|---|---|
| Citric acid | 1.0% |
| Ascorbic acid | 1.0%* |
| Sodium bisulfite | 0.05% |

*After overnight incubation at 4° C. all the samples undergone browning regardless of the ascorbic acid concentration.

FIG. 3 shows browning of medium as a result of PPO activity, under different concentrations of Sodium bisulfite.

A buffer without any antioxidant was used as a negative control. DDT was used as a positive control at the concentration of 200 mM, which is known to eliminate PPO activity when harvested from trichome cells (12, 29).

Example 6

An Automated Machine for Trichome Cells and Trichome Exudate Harvesting

A machine was designed, to enable the automation and up-scaling of protein harvesting according to protocol 2. The purpose of the machine is to harvest trichome cells and exudates from full-grown, 3 month old tomato plants (about 1 meter long and 80 cm in diameter). The machine is built of 2 main parts, (i) 2 m high and 1 m in diameter of cylinder shaped container (either made from stainless-steel, glass or a plastic); and (ii) a 2.5 m arm which operates using a 2 speed engine.

The machine has four steps of operation:
1. The plant is tight to the arm manually. The arm is introducing the plant into the container, half full with the liquid medium.
2. The arm is slowly moving up and down (engine is operating on a slow speed) the plant in the liquid medium such that trichome cells and exudates are released into the medium, without damaging other tissues of the plant.
3. The arm is moving the plant just above of the liquid medium.
4. The arm is vigorously shaking the plant up and down (engine is operating on a high speed). Doing that most of the liquid, which remained attached to the plant tissues, is released and drops falls back to the container. The semi-dried plant is removed and a new plant is tight to the arm.

Example 7

Determining Plant Architecture for Optimizing Trichome Production

Typically, the architecture of cultivated tomato plants is designed via breeding to provide the highest fruit yields, in a given space, in a given time. Moreover hand labor is routinely being practiced to optimize plant architecture for that purpose. For trichome optimized expression, plant architecture needs re-design to optimize trichome production, in a given greenhouse space in a given time. Two approaches for increasing protein yield were employed essentially, increasing the number of trichomes in leaves; and increasing the number of leaves on the plant.

Materials Methods and Results

Increasing number of trichomes on leaves—Over 300 tomato cultivars were screened for trichome density. Leaves of 4 weeks old plants were inspected, and average trichome density was measured. Best performing cultivars were grown and trichome density was tested again on mature, 14 week old plants. Trichome density was compared to previously measured density of several tomato lines (1). The seven best performing cultivars were grown in the next season and trichome density was measured again, to check the heredity of trichome density of two generations. Table 9, below summarizes trichome density of the best performing cultivars.

TABLE 9

| Var | No. of Plants 1st generation | Avg. trichome number of 1st generation | No of Plants 2nd generation | Avg. trichome number of 2nd generation |
|---|---|---|---|---|
| 309_2 | 3 | 6 | 3 | 5.3 |
| 305 | 3 | 4.7 | 3 | 5.3 |
| 249_1 | 3 | 4.3 | 3 | 5.3 |
| 247 | 3 | 3.7 | 3 | 6 |
| 273_1 | 3 | 5.4 | 3 | 4.7 |
| 294 | 3 | 4.5 | 3 | 3.2 |
| 289 | 3 | 4.2 | 3 | 3 |

(Note - the number in the above table represent only the best performing cultivars, out of 300 tested).

Folding a single leaflet and inspecting the edge of the folded leaflet was performed in order to count trichome cells. Trichome number is all trichomes found on the edge of the leaflet under ×120 magnification using binocular microscope (Optika, Italy). Previous publication has calculated for *Lycopersicon hirsutum*, var *Glabratum* (Cultivar No 273_1 in this experiment) over 100,000 trichomes per 1 gram of leaf. Assuming trichome density in this experiment remains the same, best performing *L. esculentum* cultivars (No 309_2, 305, 249_1, 247, 294, 289), identified here, have the trichome number in the same order. Each leaflet was inspected 3-5 times and an average number was calculated for the leaflet. Three different leaflet from three different plants were inspected for each cultivar in each generation.

Four cultivars were identified with the highest density of type VI (FIG. 1a) glandular trichomes on the upper part of the leaves. Among the five best performing cultivars, one belongs to *Lycopersicon hirsutum*, var *Glabratum*. (273_1) and the rest for cultivated tomato (No 309_2, 305, 249_1, 247). Interestingly, the *Lycopersicon esculentum* species cultivars exhibited up to 20 fold more coverage of type VI trichomes compared to other cultivars within this species (not shown). Overall best cultivated cultivars possessed the same density of type VI trichomes, compared to the wild species *Lycopersicon hirsutum*, var *glabratum*, which is recognized as the highest trichome density in all *Lycopersicon* genus (1, 16).

Approach B—Increasing number of leaves in a plant—Tomato plant architecture was designed manually. 35 days old plants were planted in a greenhouse. Different mechanical treatments were applied to shape plant architecture during plant growth. To avoid the collapse of the plant bush, shoots were hanged from the greenhouse ceiling using plastic strings. The three best performing treatments for plant architecture, aiming to increase trichome yield by increasing the number of leaves produced are presented hereinbelow:

1. Plant shoot number is not limited, plant height is limited to 1 m, flowers were cut-off before fruit set.
2. Plant shoot number is not limited, plant height is limited to 2 m, flowers were cut-off before fruit set.
3. Plant shoot number is not limited, leading apical meristem was cut (i.e. breaking apical dominance) when reached 0.5 m, flowers were cut-off before fruit set.
4. Plant shoot number was limited to two. Flowers and fruits remained untouched (A control treatment, usually applied for greenhouse tomatoes, grown for fruit set).

Three different indeterminant (i.e. the greenhouse type) tomato cultivars (namely 678, 1312, and 2545) previously identified as having high trichome density, were grown in the greenhouse for two months. The four above treatments were applied to five plants from each cultivar. Leaf number of each plant was calculated. Table 10, below summarizes the leaf number of tomato plants growing under different mechanical plant design.

TABLE 10

| Var | treat | N Rows | Mean (No) | Std Err (No) |
| --- | --- | --- | --- | --- |
| 678 | 1 | 5 | 94.2 | 7.61 |
| 678 | 2 | 5 | 87.4 | 5.22 |
| 678 | 3 | 5 | 71 | 5.03 |
| 678 | 4 | 5 | 27.8 | 2.75 |
| 1312 | 1 | 5 | 125 | 24.56 |
| 1312 | 2 | 5 | 148.4 | 13.12 |
| 1312 | 3 | 5 | 123 | 10.22 |
| 1312 | 4 | 5 | 54.6 | 2.84 |
| 2545 | 1 | 5 | 95.6 | 23.89 |
| 2545 | 2 | 5 | 81.4 | 3.91 |
| 2545 | 3 | 5 | 81.8 | 12.92 |
| 2545 | 4 | 5 | 34.4 | 4.48 |

As is evident from Table 10, above and FIGS. 5a-c, a significant increase [at 0.05 level for cultivar 2545 (FIG. 5c) and 0.01 level for cultivars 678 and 1312 (FIGS. 5a-b, respectively)] was observed in response to treatments number 1, 2, 3 compared to control (treatment No 4). Overall a 50% increase in leaf number (2.25 to 3.39) was observed over the control. Trichome density and PPO enzyme activity in trichomes were measured in each plant to verify that the increase in leaf number is not correlated with a decrease in trichome or protein production. No significant change (at 0.05 level) was observed for either trichome number or protein accumulation, following growth in leaf number (data not shown).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED

Additional References are Cited in the Text

1. Antonious G F. 2001. Production and quantification of methyl ketones in wild tomato accessions. J Environ Sci Health B.; 36(6):835-48.
2. Phillips M A, Croteau R B. 1999. Resin-based defenses in conifers. Trends Plant Sci. 4(5):184-190.
3. Wagner G J. 1991. Secreting glandular trichomes: more than just hairs. Plant Physiol. 96, 675-679.
4. Kennedy G G. 2003. Tomato, pests, parasitoids, and predators: tritrophic interactions involving the genus *Lycopersicon*. Annu Rev Entomol. 48:51-72.
5. Thipyapong P, Joel D M, Steffens J C. 1997. Differential Expression and Turnover of the Tomato Polyphenol Oxidase Gene Family during Vegetative and Reproductive Development. Plant Physiol. 113(3):707-718.
6. Wang E, Wang R, DeParasis J, Loughrin J H, Gan S, Wagner G J. 2001. Suppression of a P450 hydroxylase gene in plant trichome glands enhances natural-product-based aphid resistance. Nat Biotechnol. 19(4):371-4.
7. Liu H C, Creech R G, Jenkins J N, Ma D P. 2000. Cloning and promoter analysis of the cotton lipid transfer protein gene Ltp3(1). Biochim Biophys Acta. 24; 1487(1):106-11.
8. Wang E, Gan S, Wagner G J. 2002. Isolation and characterization of the CYP71D16 trichome-specific promoter from *Nicotiana tabacum* L. J Exp Bot. 53(376):1891-7.
9. Hsu C Y, Creech R G, Jenkins J N, Ma D P. 1999. Analysis of promoter activity of cotton lipid transfer protein gene LTP6 in transgenic tobacco plants. Plant Sci 143, 63-70.
10. Wagner G J. 1999. Tobacco surface chemistry. In Tobacco production chemistry and technology. (eds Davis, D. L. & Nielsen, M. T.) 292-303 (Blackwell Science, Maiden, Mass.; 1999).
11. Kowalsky S P. 1989. Insect resistance in potato: purification and characterization of a polyphenol oxidase from the type A glandular trichomes of *Solanum berthaultii* Hawkes. PhD thesis Cornell University, Ithaca, N.Y.
12. Kowalsky S P, Eannetta N T, Hirzel A T, Steffens J C. 1992. Purification and characterization of a polyphenol oxidase from the type A glandular trichomes of *Solanum berthaultii*. Plant Physiol. 100, 677-684.
13. Duke S O et al. 1999. Sequestration of phytotoxins by plants: Implications for biosynthetic production. In *Bio-*

*logically active natural products: agrochemicals* (eds Cutler H G & Cutler S J) 127-136 (CRC press Boca Raton, Fla.; 1999).

14. Kesley R G, Reynolds G W, Rodriguez E. 1984. The chemistry of biologically active constituents secreted and stored in plant glandular trichomes. In *Biologically and chemistry of plant trichomes* (eds Rodriguez E, Healey P L, Mehta I) 187-241 (Plenum press New York; 1984).
15. Jefferson R A, Kavanagh T A, Bevan M W. 1987. GUS fusions: beta-glucuronidase as a sensitive and versatile gene fusion marker in higher plants. EMBO J. 6(13): 3901-7.
16. Weston P A, Johnson D A, Burton H T, Snyder J C. 1989. Trichome secretion composition, trichome densities, and spider mite resistance to ten accessions of *Lycopersicon hirsutum*. J. Amer. Soc. Hort. Sci. 114(3): 492-498.
17. Clough S J, Bent A F. 1998. Floral dip: a simplified method for *Agrobacterium*-mediated transformation of *Arabidopsis thaliana*. Plant J. 16(6): 735-43.
18. Desfeux C, Clough S J, Bent A F. 2000. Female reproductive tissues are the primary target of *Agrobacterium*-mediated transformation by the *Arabidopsis* floral-dip method. Plant Physiol. 123(3): 895-904.
19. Fillatti (1987) Efficient transfer of a glyphosate tolerance gene into tomato using a binary *Agrobacterium tumefaciens* vector. Bio/Technology 5 726-730.
20. Dominguez O., C. Lopez-Larrea. 1994. Gene walking by unpredictably primed PCR. Nucleic Acids Research. 22:3247-3248.
21. Hareven D, Guffinger T, Parnis A, Eshed Y, Lifschitz E. 1996. The making of a compound leaf: genetic manipulation of leaf architecture in tomato. Cell. 84:735-44.
22. Hu Y, Xie Q, Chua N H. 2003. The *Arabidopsis* auxin-inducible gene ARGOS controls lateral organ size. Plant Cell. 15:1951-61.
23. Kim J H, Choi D, Kende H. 2003. The AtGRF family of putative transcription factors is involved in leaf and cotyledon growth in *Arabidopsis*. Plant J. 36:94-104.
24. Smith H M, Hake S. 2003. The interaction of two homeobox genes, BREVIPEDICELLUS and PENNYWISE, regulates internode patterning in the *Arabidopsis* inflorescence. Plant Cell. Aug. 15:1717-27.
25. Sorefan K, Booker J, Haurogne K, Goussot M, Bainbridge K, Foo E, Chatfield S, Ward S, Beveridge C, Rameau C, Leyser O. 2003. MAX4 and RMS1 are orthologous dioxygenase-like genes that regulate shoot branching in *Arabidopsis* and pea. Genes Dev. 17:1469-74.
26. Rose A B, Last R L. 1997. Introns act post-transcriptionally to increase expression of the *Arabidopsis thaliana* tryptophan pathway gene PAT1. Plant J. 11:455-64.
27. Morello L, Bardini M, Sala F, Breviario D. 2002. A long leader intron of the Ostub16 rice beta-tubulin gene is required for high-level gene expression and can autonomously promote transcription both in vivo and in vitro. Plant J. 29:33-44.
28. Sommer A, Ne'eman E, Steffens J. C, Mayer A. M, Harel E. 1994. Import, targeting and processing of a plant Polyphenol oxidase. Plant Physiol. 105:1301-1311.
29. Yu H, Kowalsky S. P, and Steffens J. C. 1992. Comparison of Polyphenol Oxidase expression in glandular trichomes of *Solanum* and *Lycopersicon* species. Plant Physiol. 100, 1885-1890.
30. Pérez-Estrada L. B, Cano-Santana Z and Oyama K. 2000. Variation in leaf trichomes of *Wigandia urens*: environmental factors and physiological consequences. *Tree Physiol,* 20:629-632

What is claimed is:

1. An isolated polynucleotide comprising the nucleic acid sequence set forth in SEQ ID NO:26.

2. A nucleic acid construct comprising the isolated polynucleotide of claim 1 and at least one heterologous polynucleotide operably linked to the isolated polynucleotide.

3. The nucleic acid construct of claim 2, wherein the nucleic acid construct further comprises; a nucleic acid sequence encoding a peptide capable of directing transport of a polypeptide fused thereto into a subcellular compartment of a trichome.

4. The nucleic acid construct of claim 3, wherein said nucleic acid sequence encoding said peptide capable of directing transport of the polypeptide is selected from the group consisting of SEQ ID NOs: 59, 61, 63, 65 and 75.

5. The nucleic acid construct of claim 3, wherein said subcellular compartment of a trichome is a leucoplast.

6. A transgenic plant cell transformed with the nucleic acid construct of claim 2.

7. A transgenic plant transformed with the nucleic acid construct of claim 2.

8. The nucleic acid construct of claim 2, further comprising an isolated polynucleotide comprising a nucleic acid sequence encoding a peptide capable of directing transport of a polypeptide fused thereto into a subcellular compartment of a trichome, wherein said peptide is encoded by the polynucleotide sequence set forth in SEQ ID NO:59, 61, 63, 65 or 75.

9. A nucleic acid construct comprising the isolated polynucleotide of claim 8.

10. The nucleic acid construct of claim 9, further comprising an expressible polynucleotide sequence translationally fused to said nucleic acid sequence encoding said peptide.

\* \* \* \* \*